United States Patent [19]
Schulze et al.

[11] Patent Number: 5,680,982
[45] Date of Patent: Oct. 28, 1997

[54] SURGICAL INSTRUMENT

[75] Inventors: Dale R. Schulze, Lebanon; Joseph Paraschac, Cincinnati; William D. Fox, New Richmond, all of Ohio; Michael E. Setser, Burlington, Ky.; Kenneth S. Wales, Mason; Mark S. Zeiner, Milford, both of Ohio

[73] Assignee: Ethicon ENdo-Surgery, Inc., Cincinnati, Ohio

[21] Appl. No.: 725,684

[22] Filed: Oct. 2, 1996

Related U.S. Application Data

[62] Division of Ser. No. 359,107, Dec. 19, 1994.

[51] Int. Cl.⁶ .................................................. A61B 17/068
[52] U.S. Cl. .................. 227/175.1; 227/19; 227/176.1; 227/179.1; 600/139; 600/141
[58] Field of Search ........................... 227/175.1, 19, 227/176.1, 178.1, 179.1; 600/139, 141, 142

[56] References Cited

U.S. PATENT DOCUMENTS

| | | |
|---|---|---|
| 944,830 | 12/1909 | Sussmann . |
| 2,476,249 | 7/1949 | Payne ........................... 74/388 |
| 2,737,822 | 3/1956 | Morse .......................... 74/222 |
| 2,885,686 | 5/1959 | Giaimo ........................... 3/1.1 |
| 2,975,785 | 3/1961 | Sheldon ....................... 128/6 |
| 3,060,972 | 10/1962 | Sheldon ...................... 138/120 |
| 3,071,161 | 1/1963 | Ulrich ......................... 138/120 |
| 3,090,378 | 5/1963 | Sheldon et al. .................. 128/4 |
| 3,162,214 | 12/1964 | Bazinet ....................... 138/120 |
| 3,190,286 | 6/1965 | Stokes ........................ 128/4 |
| 3,256,875 | 6/1966 | Tsepelve et al. ................ 128/8 |
| 3,270,641 | 9/1966 | Gosselin ...................... 95/11 |
| 3,335,620 | 8/1967 | Vertut ......................... 74/501 |
| 3,557,780 | 1/1971 | Sato .......................... 128/4 |
| 3,572,325 | 3/1971 | Bazell et al. ................... 128/6 |
| 3,583,393 | 6/1971 | Tahakashi ...................... 128/4 |
| 3,587,872 | 6/1971 | Pauly ......................... 214/1 BC |
| 3,788,303 | 1/1974 | Hall .......................... 128/4 |
| 3,799,151 | 3/1974 | Fukaumi et al. .................. 128/6 |
| 3,892,228 | 7/1975 | Mitsui ........................ 128/4 |
| 3,998,216 | 12/1976 | Hosono ........................ 128/6 |
| 4,054,128 | 10/1977 | Seufert et al. .................. 128/4 |
| 4,078,555 | 3/1978 | Takahaski ..................... 128/4 |
| 4,108,211 | 8/1978 | Tanaka ........................ 138/120 |
| 4,203,430 | 5/1980 | Takahashi ..................... 128/4 |
| 4,259,876 | 4/1981 | Belyanin et al. ................ 74/469 |
| 4,273,111 | 6/1981 | Tsukaya ....................... 128/6 |
| 4,283,165 | 8/1981 | Vertut ........................ 414/733 |
| 4,290,421 | 9/1981 | Siegmund ..................... 128/6 |
| 4,347,837 | 9/1982 | Hosono ........................ 128/6 |
| 4,351,323 | 9/1982 | Ouchi et al. ................... 128/4 |
| 4,432,349 | 2/1984 | Oshiro ........................ 128/4 |
| 4,473,077 | 9/1984 | Noiles et al. .................. 128/305 |
| 4,483,326 | 11/1984 | Yamaka et al. .................. 128/4 |
| 4,494,417 | 1/1985 | Larson et al. .................. 74/469 |
| 4,503,842 | 3/1985 | Takayama ...................... 128/4 |
| 4,557,254 | 12/1985 | Yamaguchi ..................... 128/4 |
| 4,593,679 | 6/1986 | Collins ....................... 128/4 |
| 4,606,343 | 8/1986 | Conta et al. ................... 128/305 |
| 4,688,555 | 8/1987 | Wardle ........................ 128/4 |
| 4,700,693 | 10/1987 | Lia et al. ..................... 128/4 |
| 4,718,407 | 1/1988 | Chikama ....................... 128/4 |
| 4,721,099 | 1/1988 | Chikama ....................... 128/4 |
| 4,726,355 | 2/1988 | Okada ......................... 128/4 |
| 4,753,223 | 6/1988 | Bremer ........................ 128/4 |

(List continued on next page.)

*Primary Examiner*—Scott A. Smith
*Attorney, Agent, or Firm*—Paul A. Coletti

[57] ABSTRACT

A surgical instrument for performing endoscopic surgical procedures. In one embodiment, the instrument includes a knife that remains unexposed until initiation of a cutting sequence, and returns to an unexposed position at the conclusion of the cutting sequence, minimizing the risk of injury to the person handling the instrument. In another embodiment, the instrument includes a flexible neck for articulating a surgical head assembly with respect to the shaft of the instrument. In another embodiment, a device for locking the articulated head at an angle of articulation is provided. In yet another embodiment, a mechanism for opening and closing an anvil assembly is disclosed.

6 Claims, 43 Drawing Sheets

U.S. PATENT DOCUMENTS

| | | | |
|---|---|---|---|
| 4,754,909 | 7/1988 | Barker et al. | 227/19 |
| 4,762,118 | 8/1988 | Lia et al. | 128/4 |
| 4,762,119 | 8/1988 | Allred, III et al. | 128/4 |
| 4,770,185 | 9/1988 | Silverstein et al. | 128/661.08 |
| 4,773,395 | 9/1988 | Suzuki et al. | 128/4 |
| 4,779,612 | 10/1988 | Kishi | 128/6 |
| 4,787,369 | 11/1988 | Allred, III et al. | 128/4 |
| 4,790,294 | 12/1988 | Allred, III et al. | 128/4 |
| 4,794,912 | 1/1989 | Lia | 128/4 |
| 4,796,607 | 1/1989 | Allred, III et al. | 128/4 |
| 4,805,596 | 2/1989 | Hatori | 128/4 |
| 4,815,911 | 3/1989 | Bengtson et al. | 414/7 |
| 4,834,069 | 5/1989 | Umeda | 128/4 |
| 4,873,965 | 10/1989 | Danieli | 128/6 |
| 4,905,666 | 3/1990 | Fukuda | 128/4 |
| 4,911,148 | 3/1990 | Sosonowski et al. | 128/6 |
| 4,919,112 | 4/1990 | Siegmund | 128/4 |
| 4,947,827 | 8/1990 | Opie et al. | 128/4 |
| 4,977,790 | 12/1990 | Nishi et al. | 74/479 |
| 4,996,974 | 3/1991 | Ciarlei | 128/4 |
| 5,002,041 | 3/1991 | Chikama | 128/4 |
| 5,005,558 | 4/1991 | Aomori | 128/4 |
| 5,007,406 | 4/1991 | Takahashi et al. | 128/4 |
| 5,014,515 | 5/1991 | Krauter | 60/581 |
| 5,014,685 | 5/1991 | Takahashi | 128/4 |
| 5,025,804 | 6/1991 | Kondo | 128/4 |
| 5,042,707 | 8/1991 | Taheri | 606/213 |
| 5,108,819 | 4/1992 | Wollschlager et al. | 128/662.06 |
| 5,125,395 | 6/1992 | Adair | 128/4 |
| 5,143,475 | 9/1992 | Chikama | 403/291 |
| 5,158,086 | 10/1992 | Brown et al. | 128/662.03 |
| 5,167,221 | 12/1992 | Chikama | 128/4 |
| 5,168,864 | 12/1992 | Shockey | 128/4 |
| 5,174,276 | 12/1992 | Crockard | 128/4 |
| 5,174,277 | 12/1992 | Matsumaru | 128/4 |
| 5,176,126 | 1/1993 | Chikama | 128/4 |
| 5,178,129 | 1/1993 | Chikama et al. | 128/4 |
| 5,179,935 | 1/1993 | Miyagi | 128/4 |
| 5,195,968 | 3/1993 | Lundquist et al. | 604/95 |
| 5,391,180 | 2/1995 | Tovey et al. | 606/205 |
| 5,394,864 | 3/1995 | Kobayashi et al. | 128/4 |
| 5,411,519 | 5/1995 | Tovey et al. | 606/207 |
| 5,417,203 | 5/1995 | Tovey et al. | 128/4 |

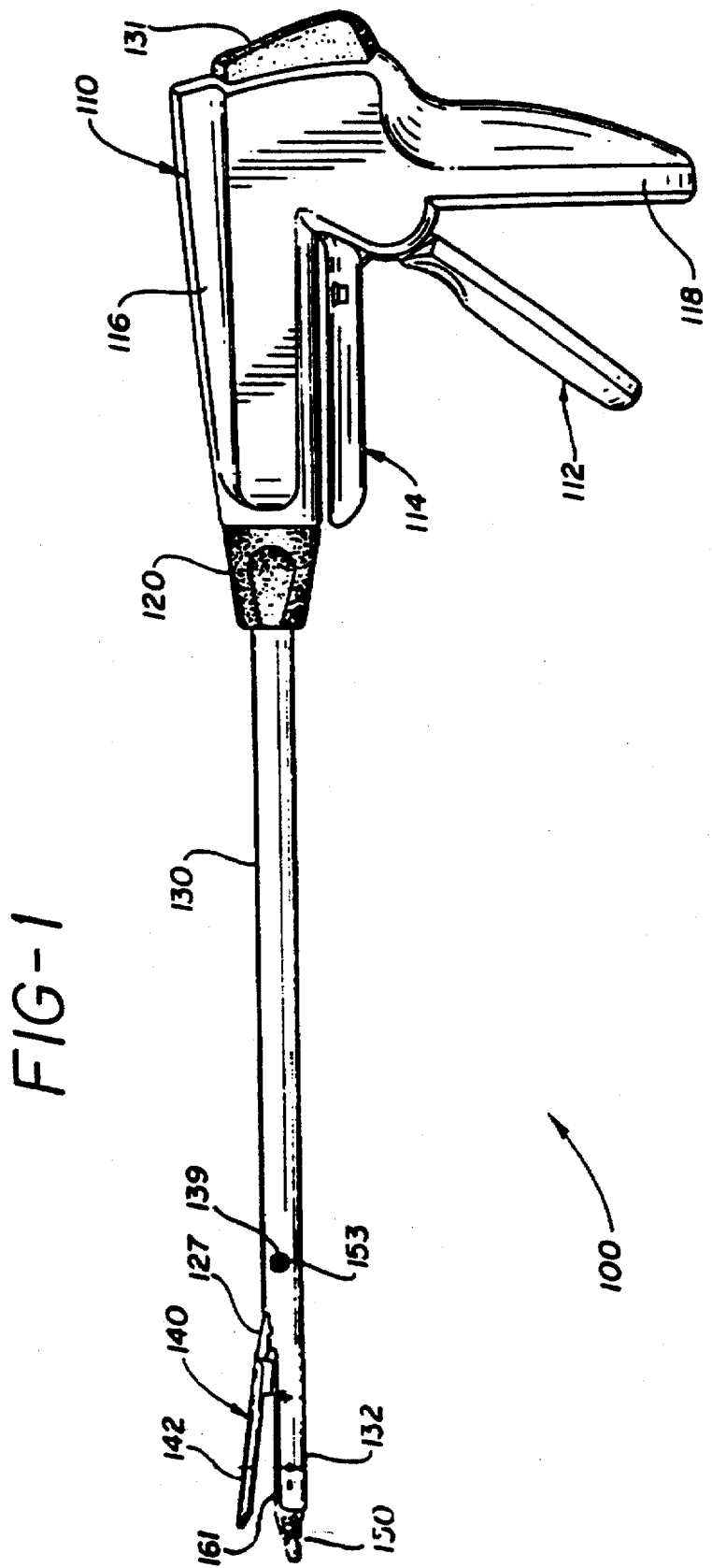

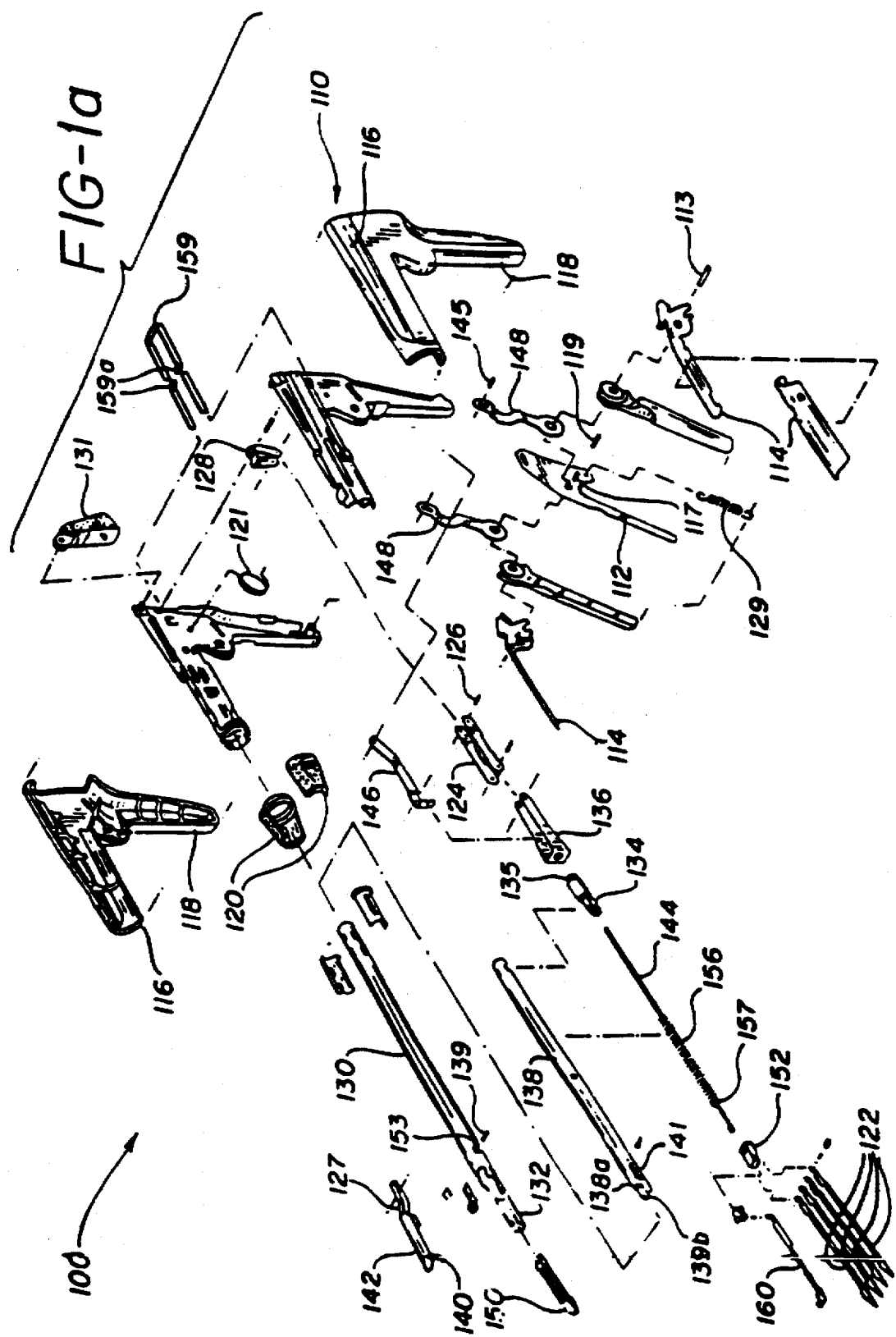

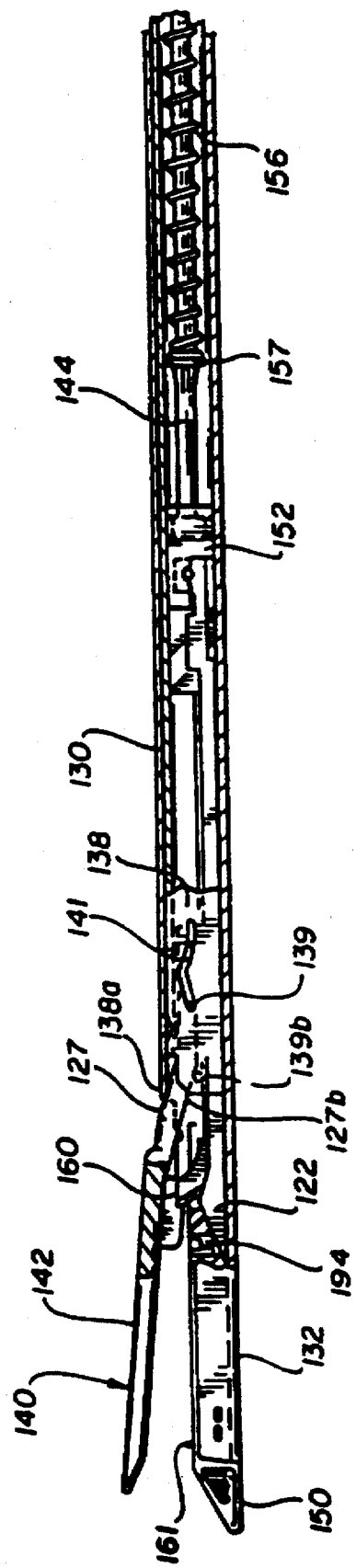

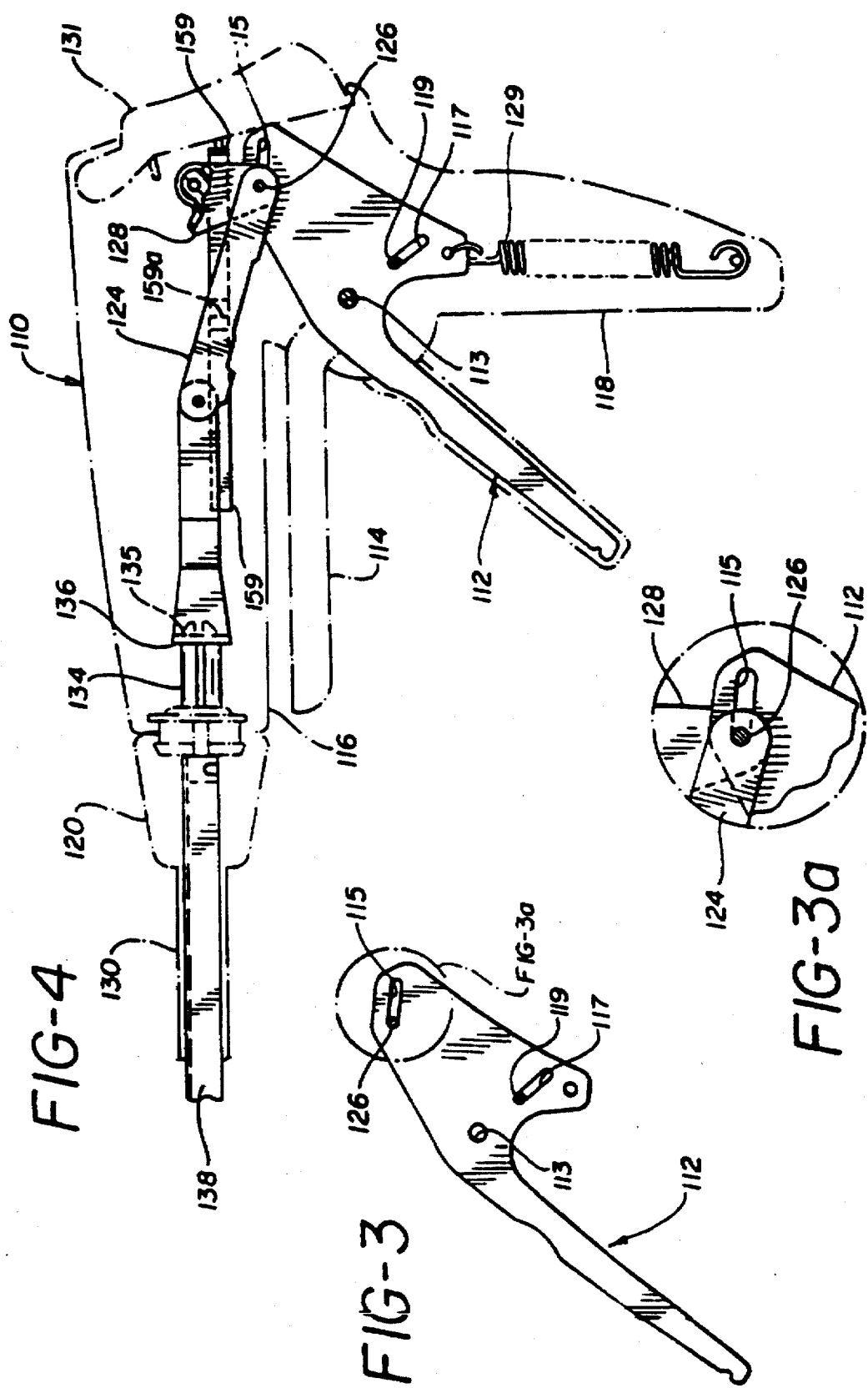

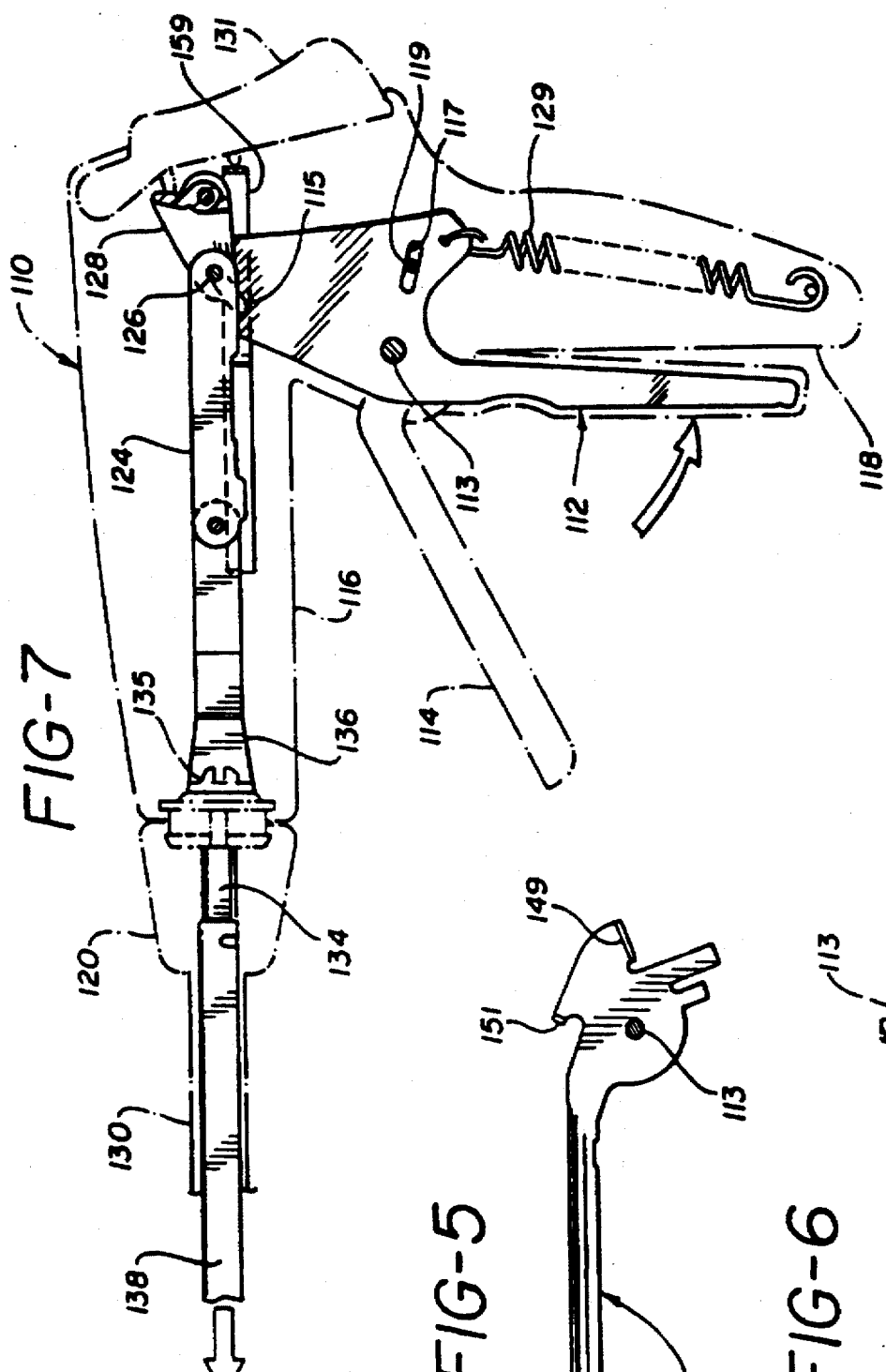

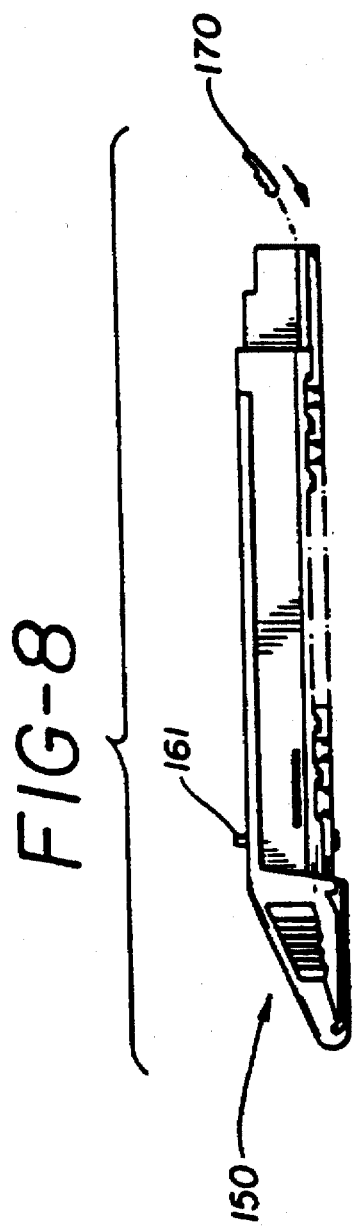
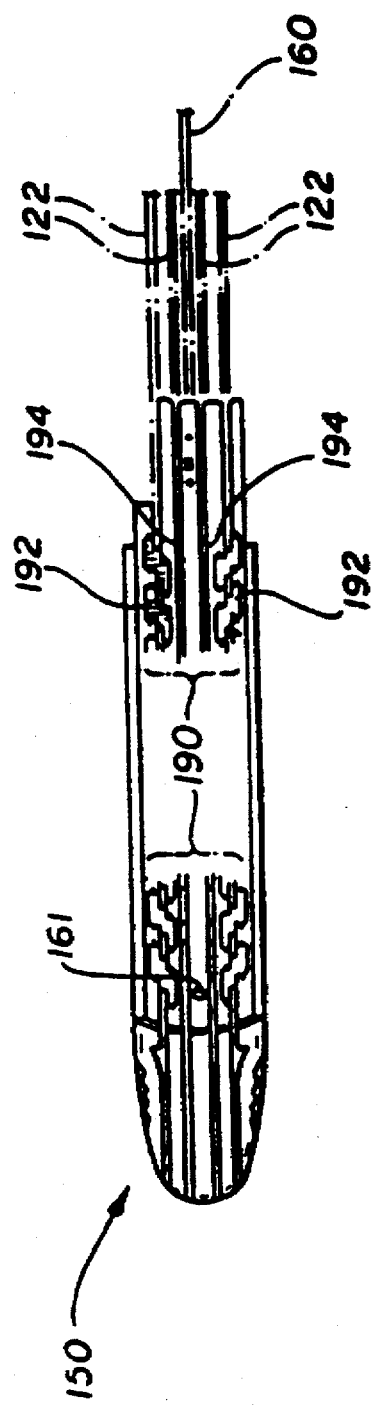

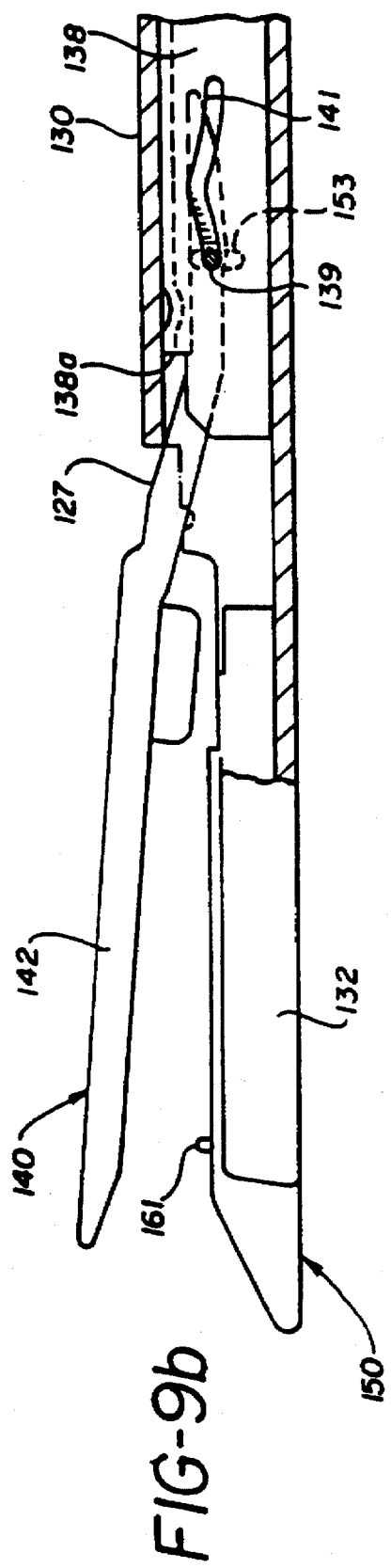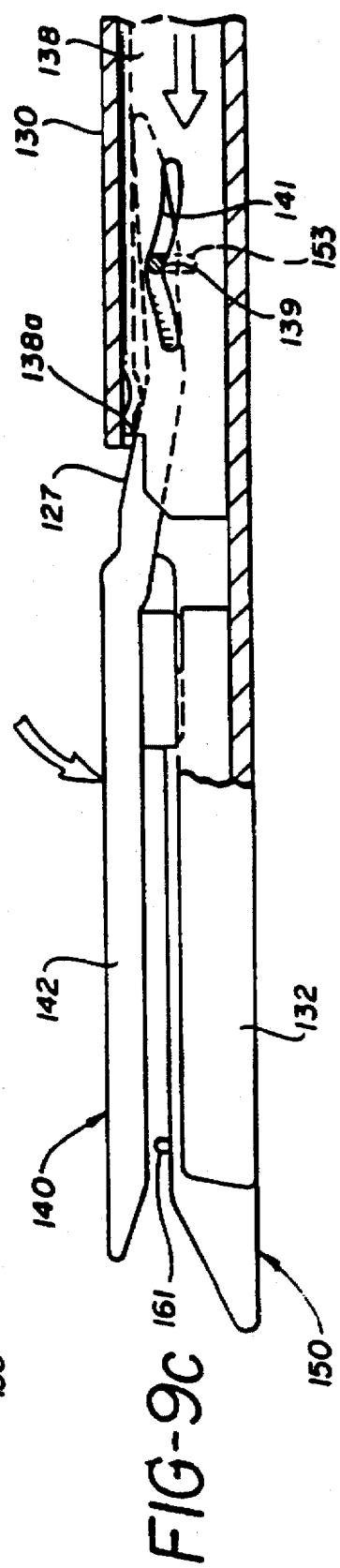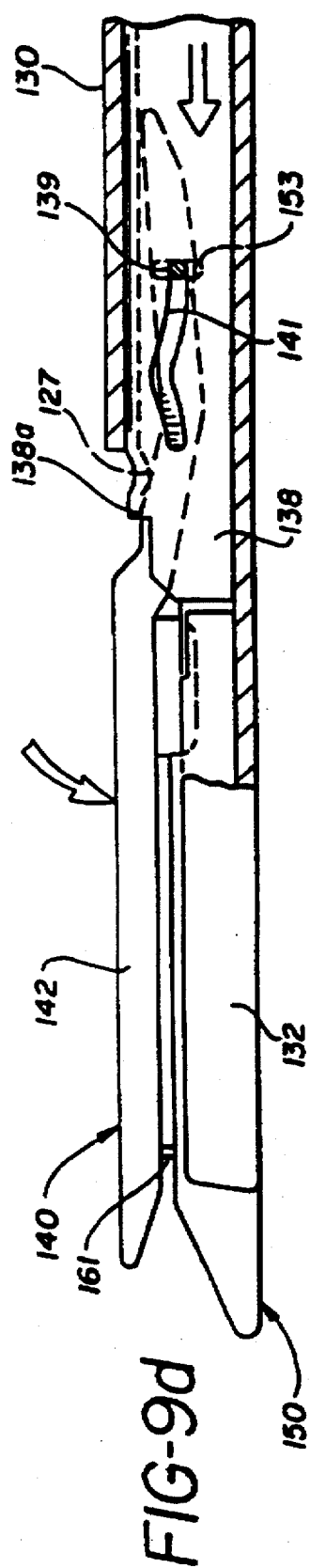

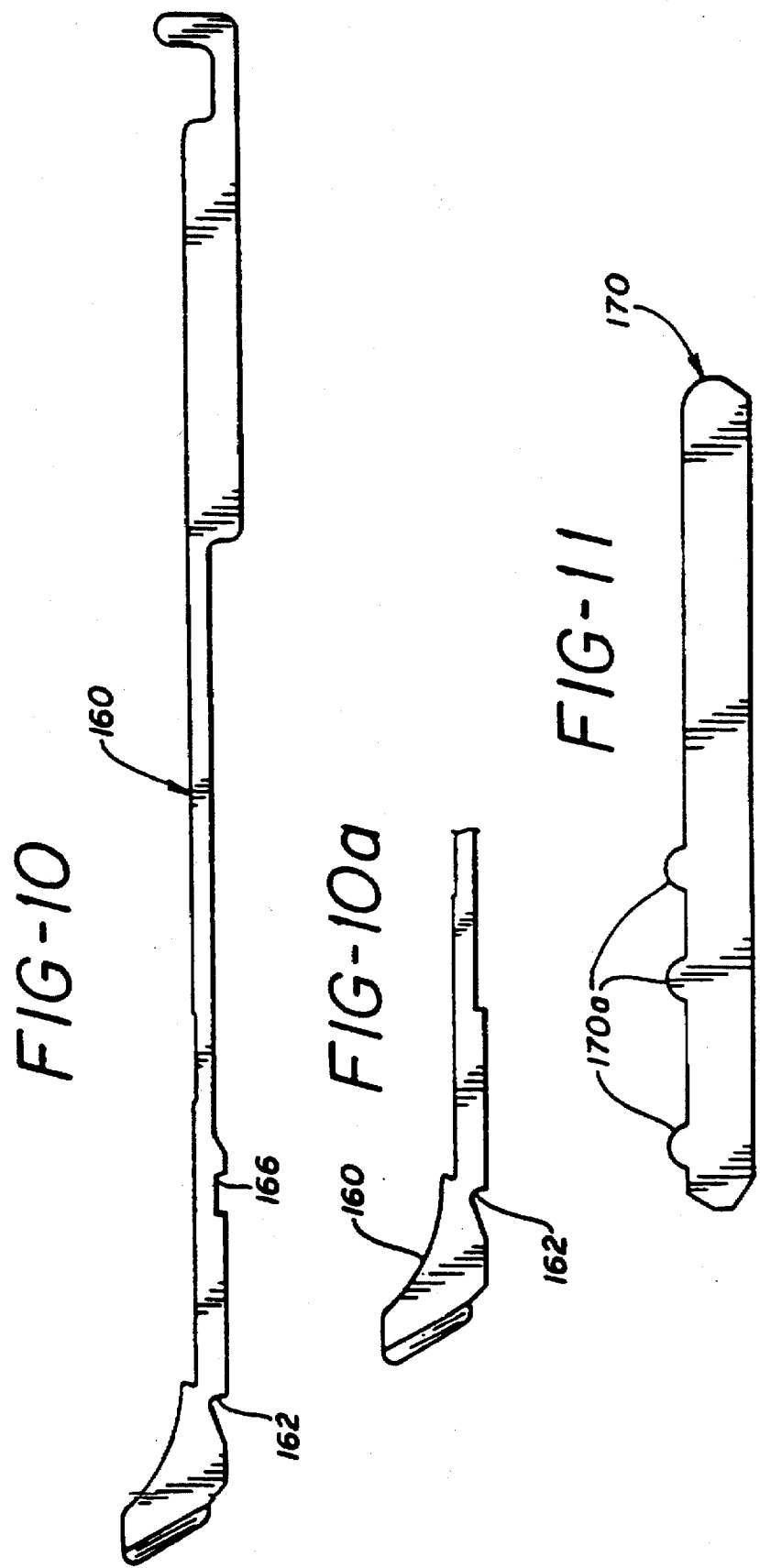

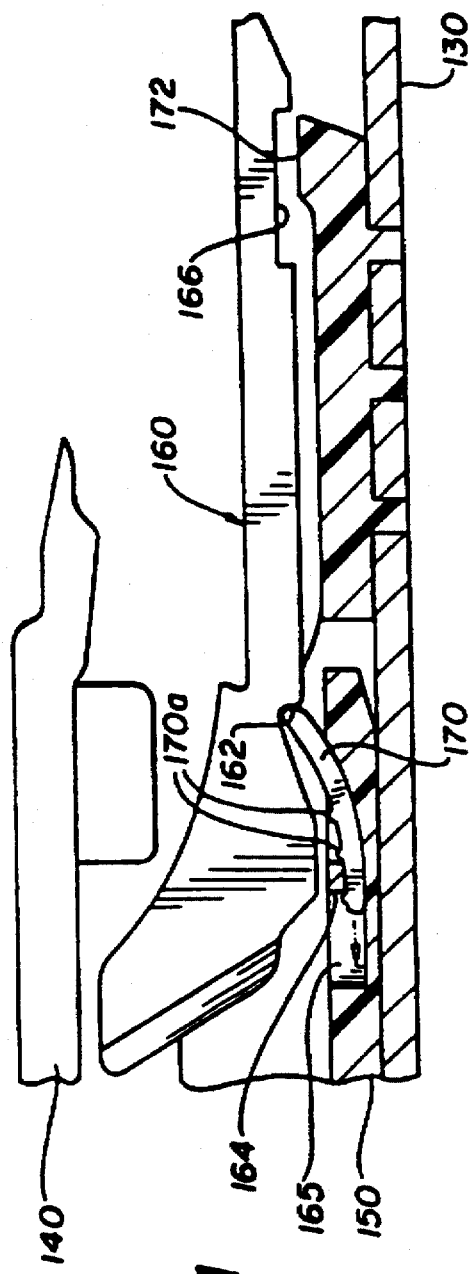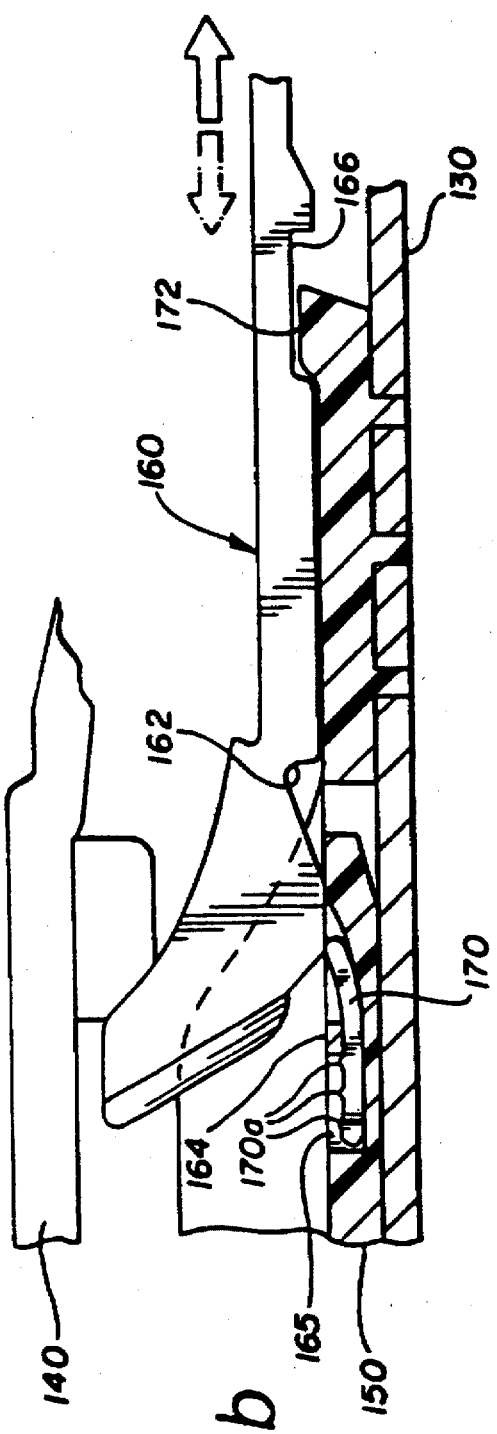

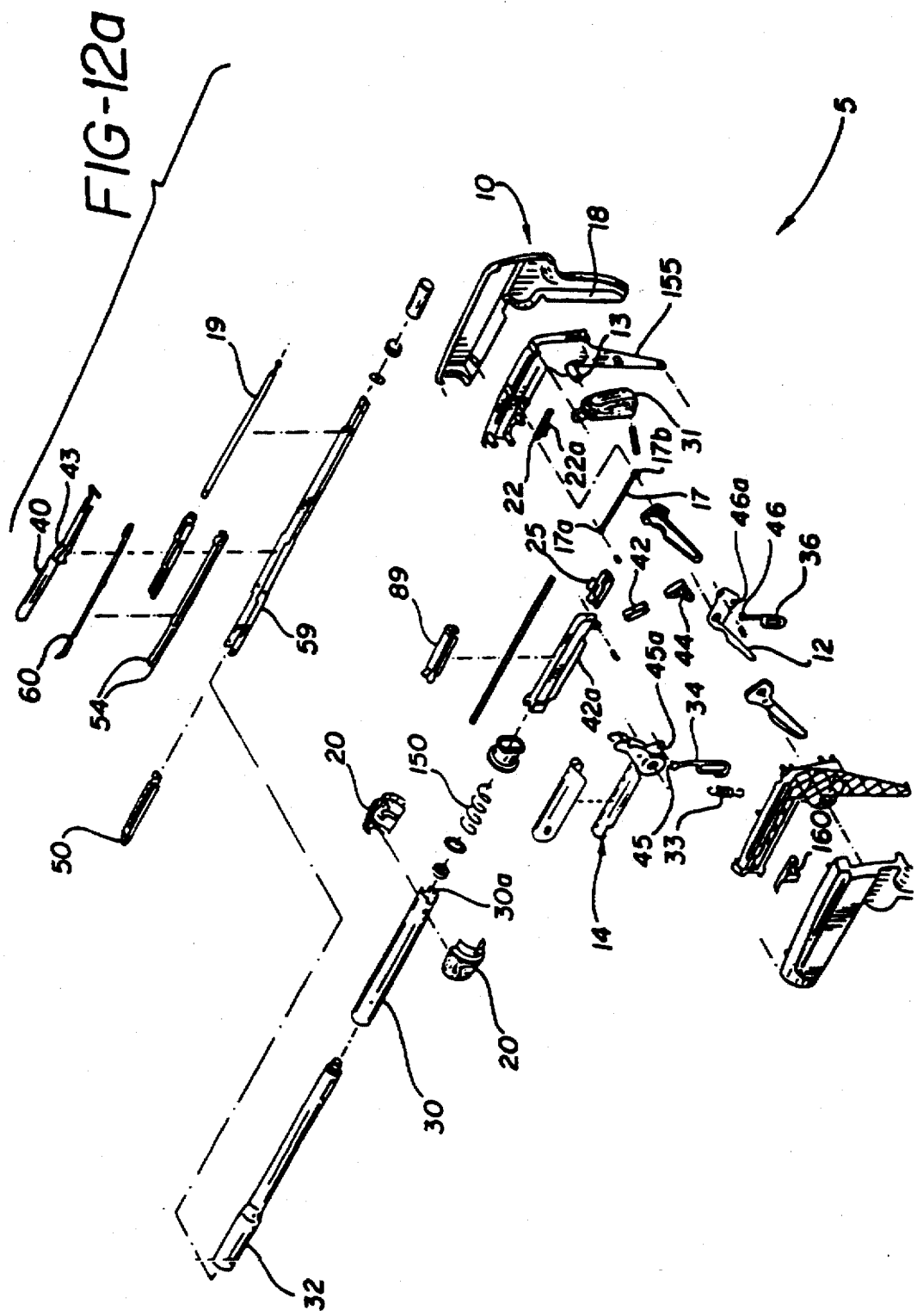

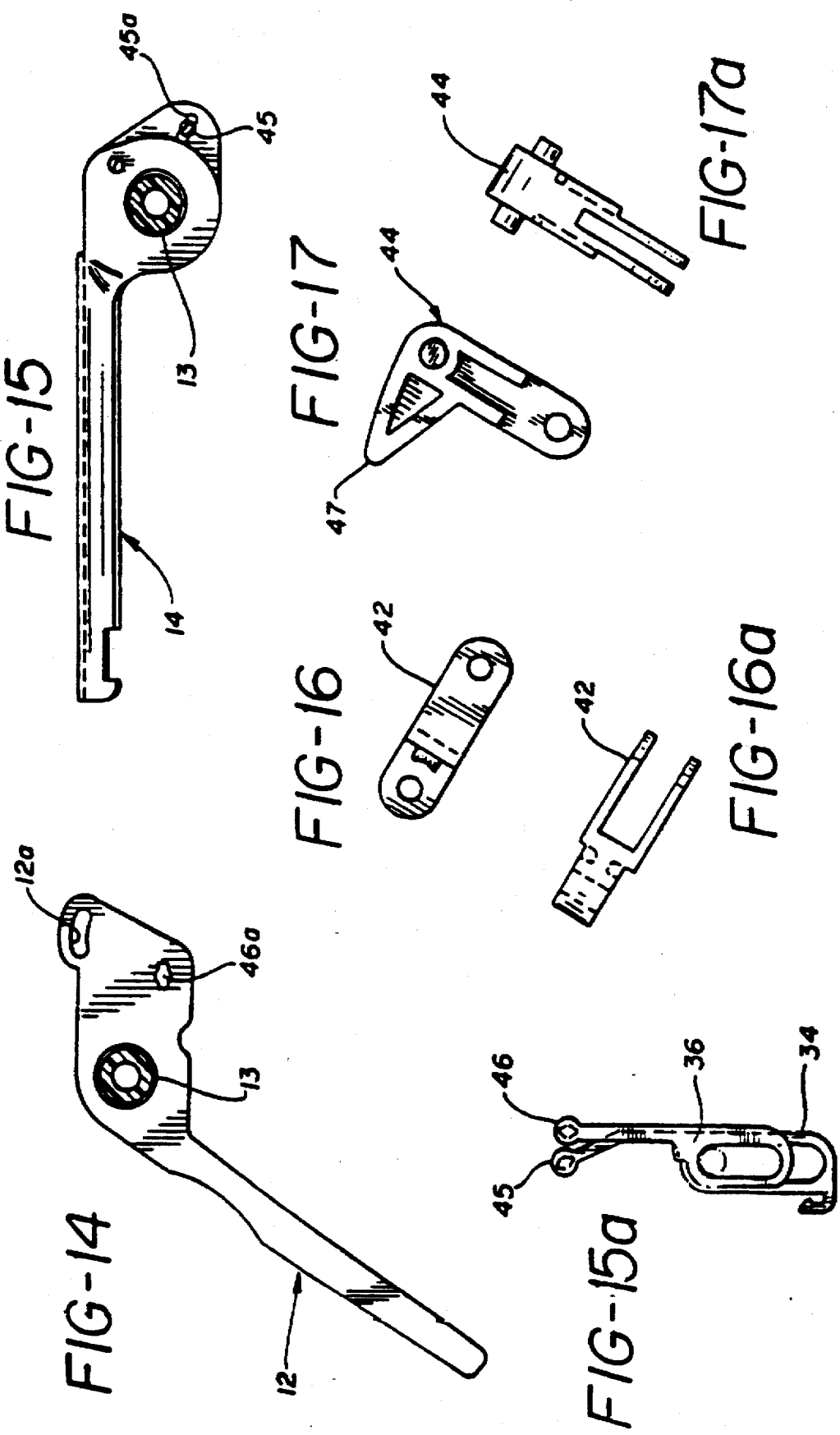

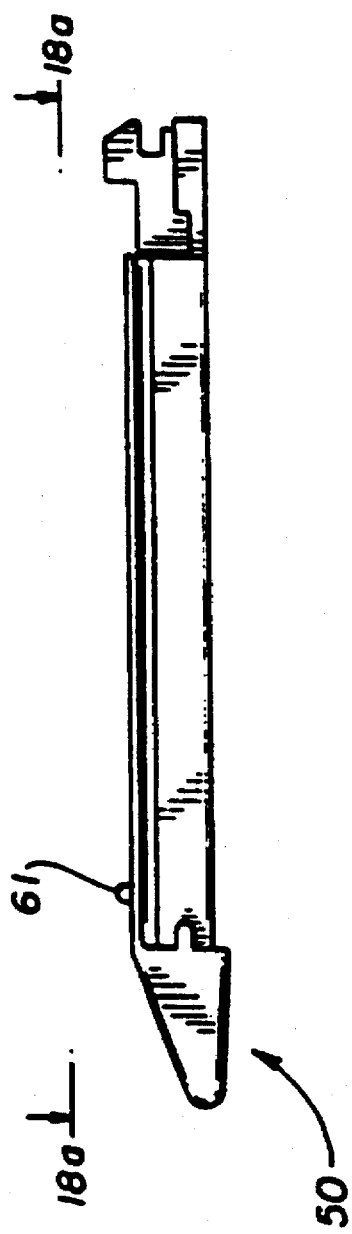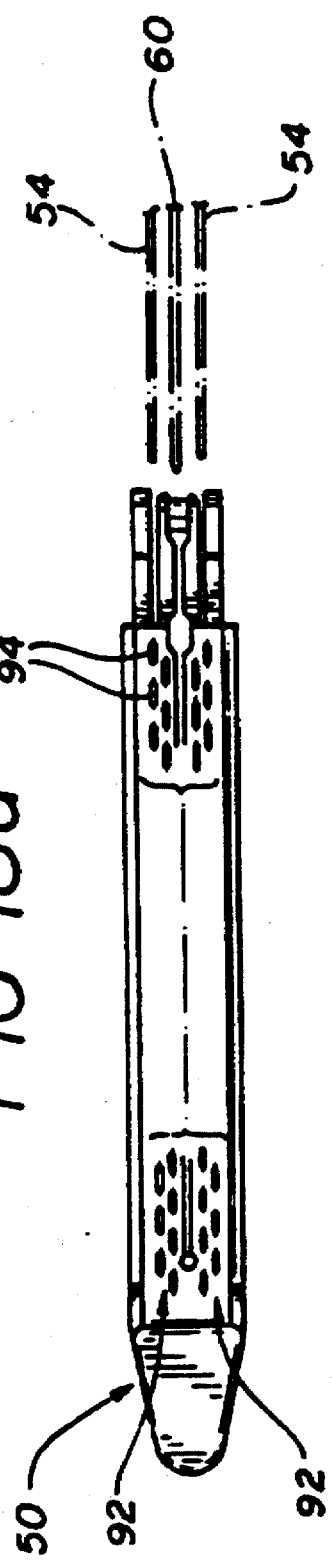

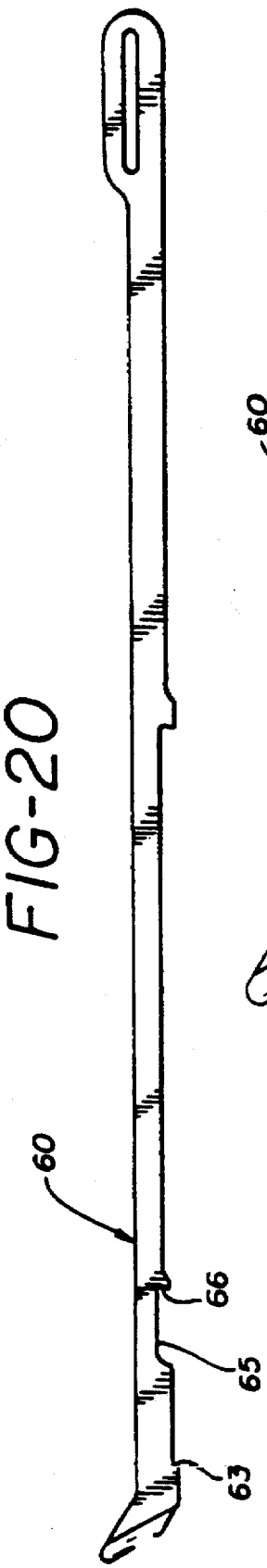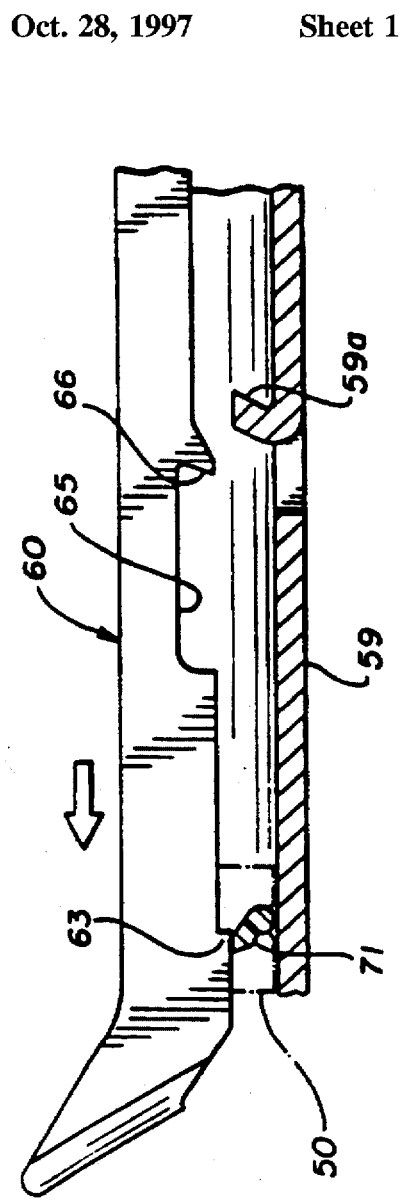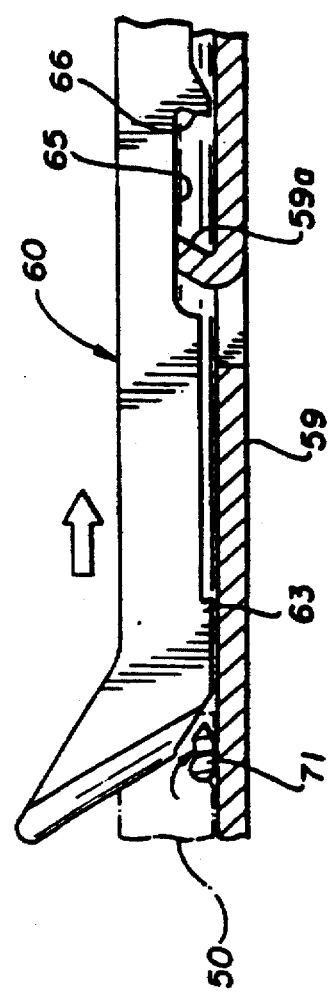

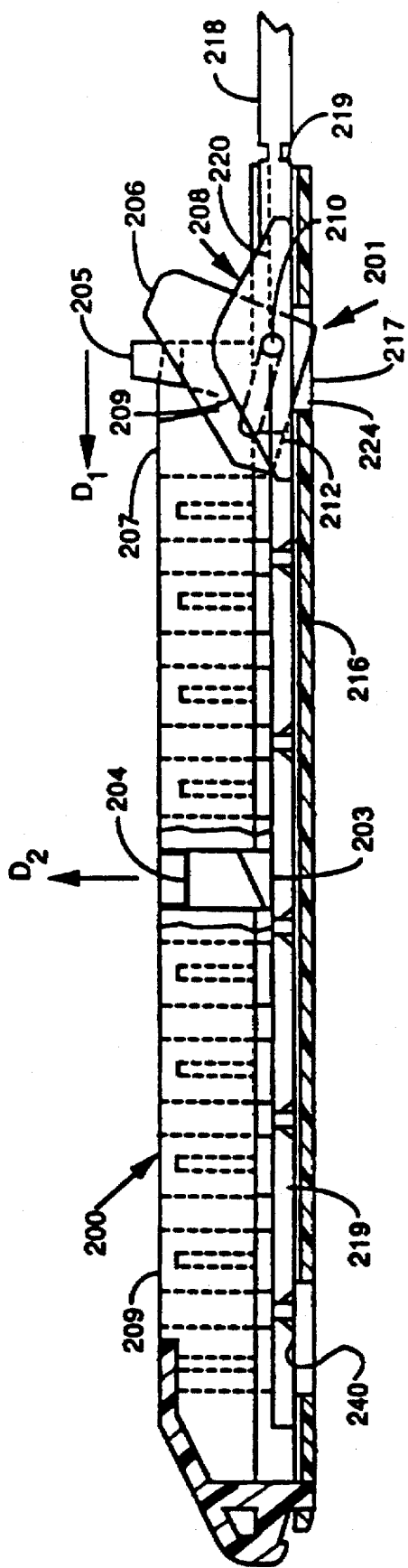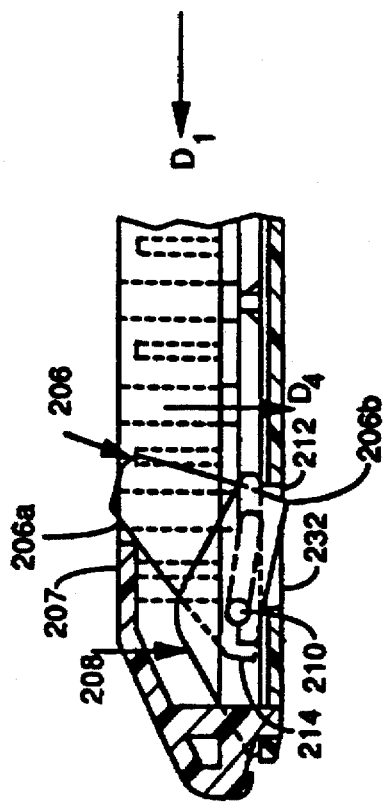
FIG. 21a
FIG. 21b

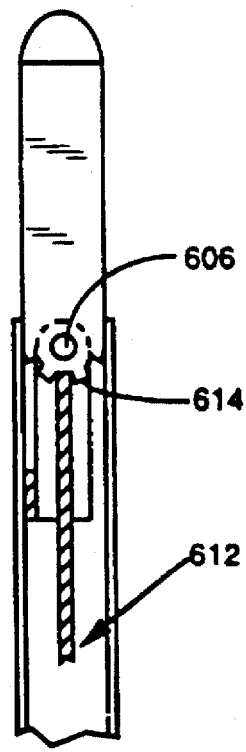
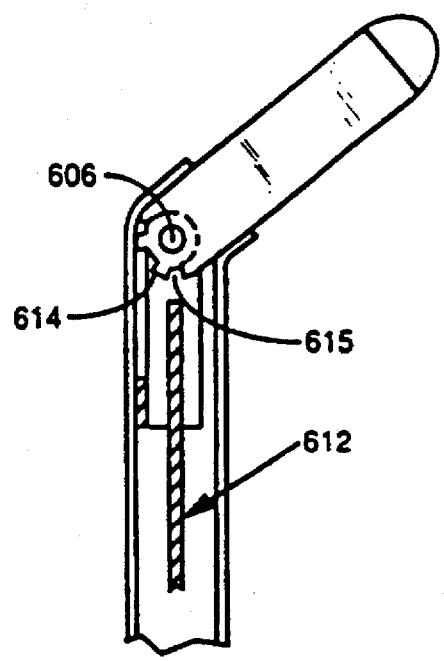
FIG. 29A  FIG. 29B
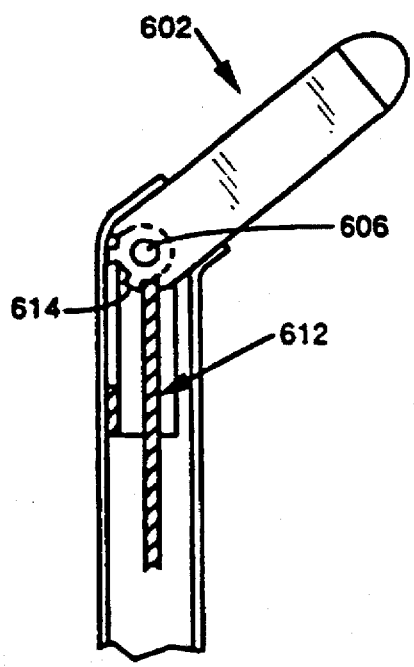
FIG. 29C

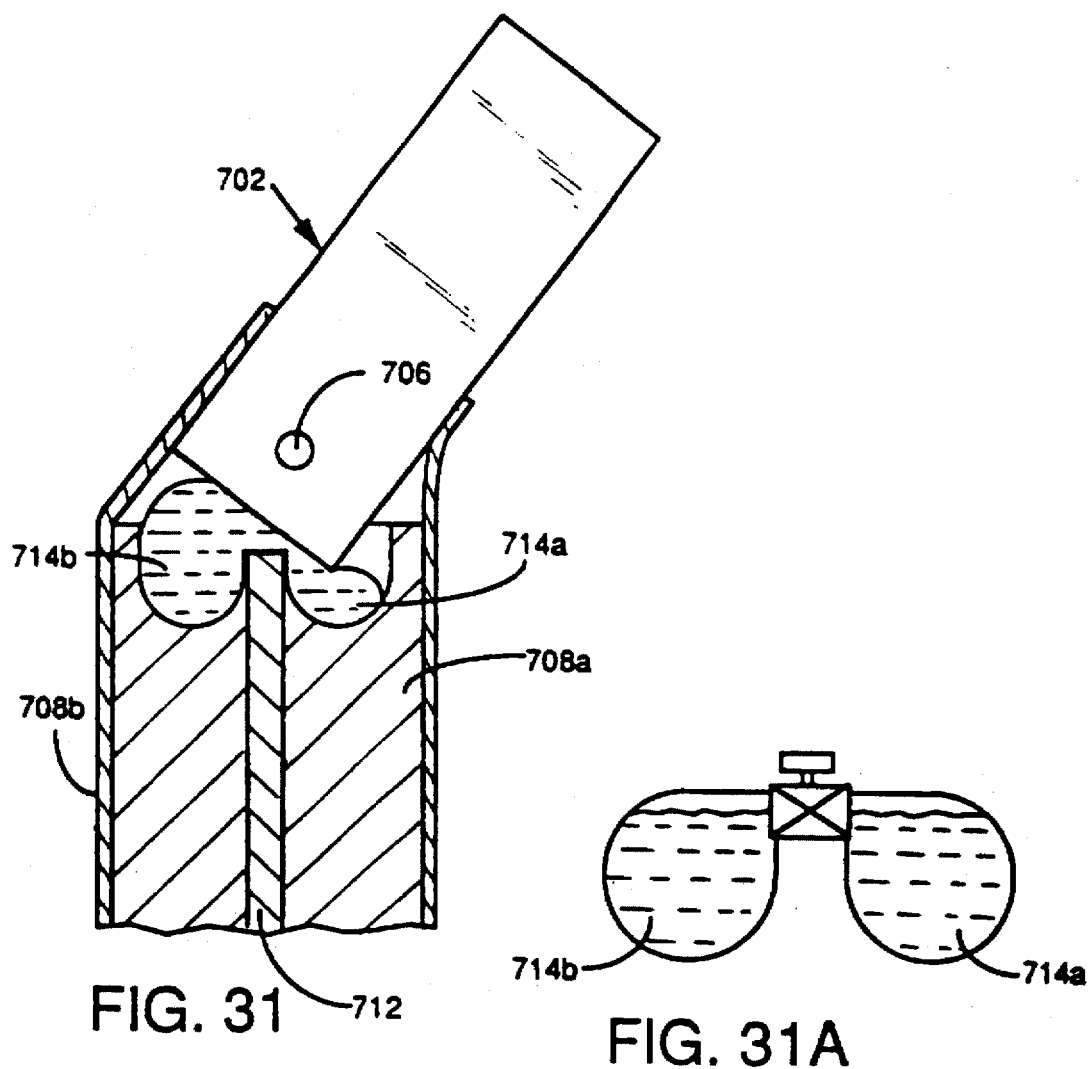
FIG. 31
FIG. 31A
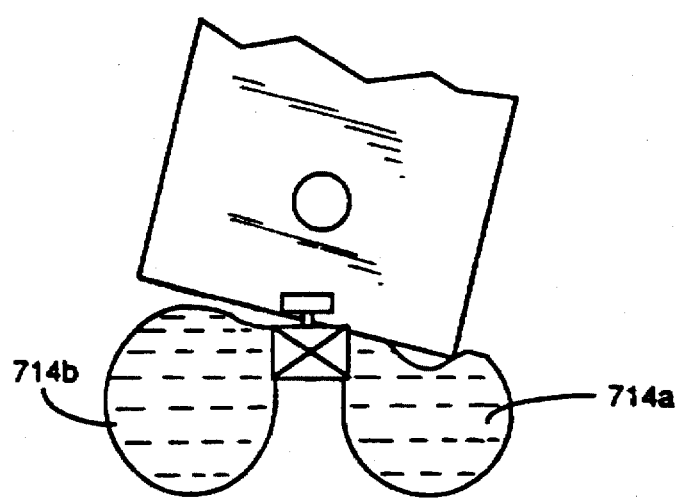
FIG. 31B

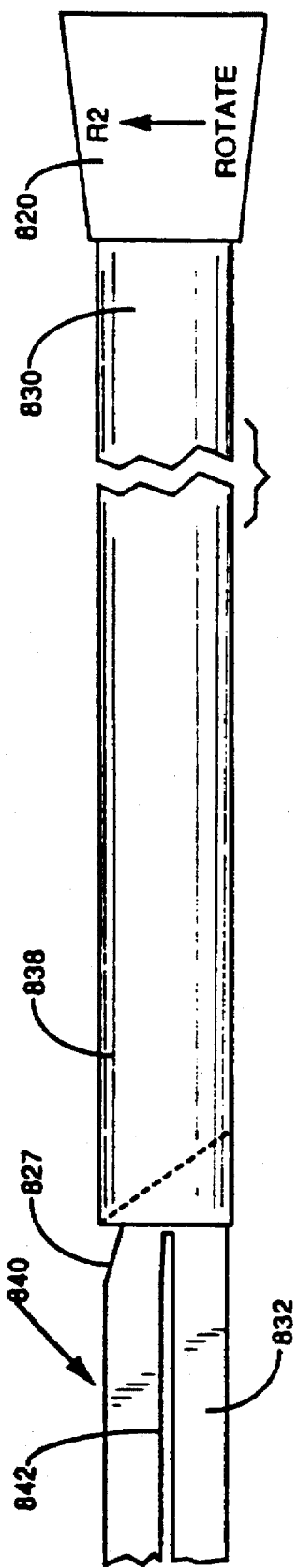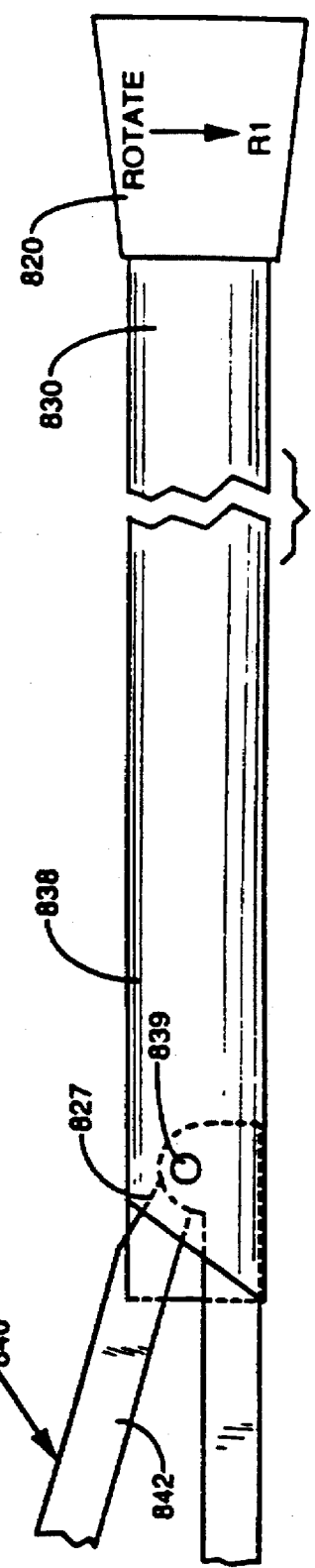

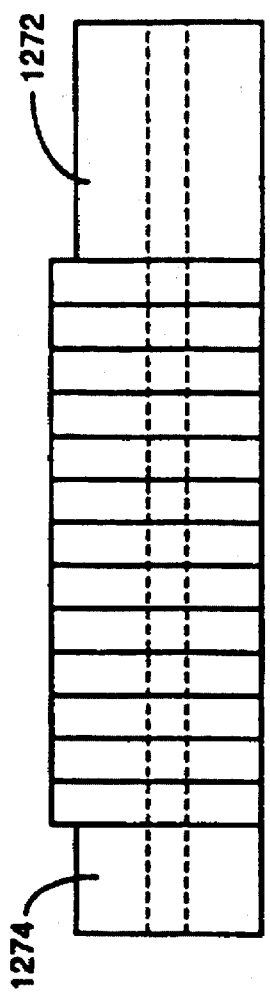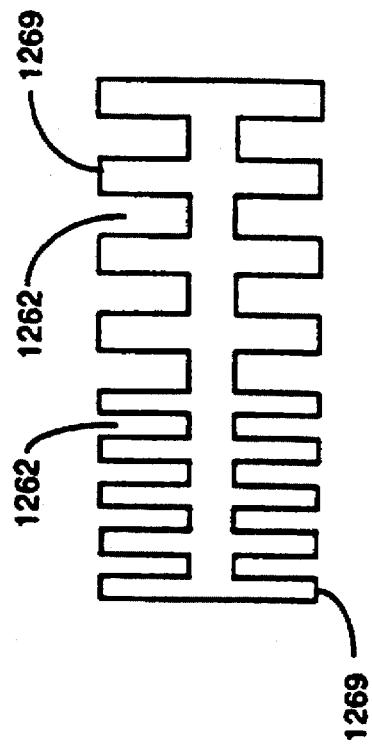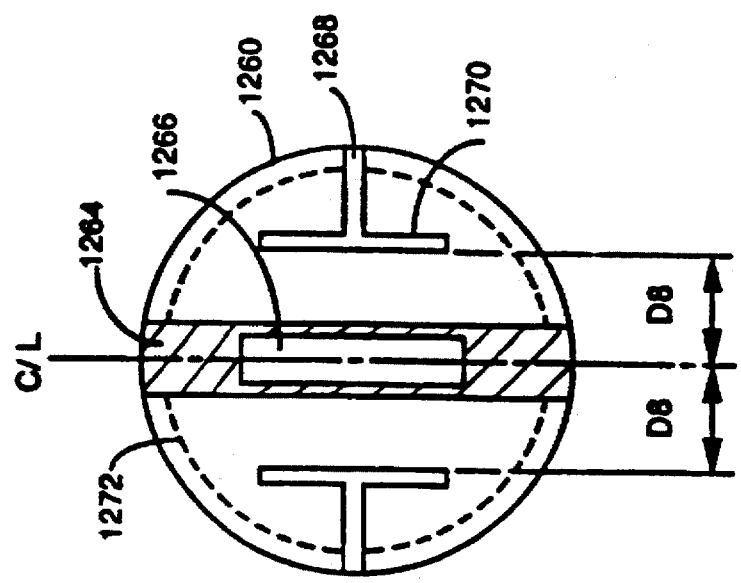

3
SURGICAL INSTRUMENT

This is a division of application Ser. No. 08/359,107, filed Dec. 19, 1994, pending which is hereby incorporated by reference.

FIELD OF THE INVENTION

This invention relates generally to medical engineering, and more specifically it relates to laparoscopic or endoscopic surgery. Most specifically, it relates to a surgical instrument which may be articulating, having improved articulation capability, including an articulation lock and improved articulation connections, may be capable of performing clamping, closures and cutting of lumen and tissue, and may include a safety wedge/sled that provides a safety for knife protection once a cutting sequence is completed. This is accomplished in a mechanism which can be used endoscopically, that is through a trocar cannula or alone, through an incision.

BACKGROUND OF THE INVENTION

In recent years surgery has markedly advanced through the performance of laparoscopic and endoscopic surgical procedures such as cholecystectomies, gastrostomies, appendectomies, and hernia repair. Also, the application of endoscopic surgical stapling and suturing instruments has been provided in cardiovascular and pulmonary surgery, as well as operative inventions in the gastrointestinal tract. Such endoscopic instruments are capable of providing hemostasis and also of cutting tissue. This reduces operating and recuperation time. These stapling procedures are accomplished through a trocar assembly, which is a surgical instrument used to puncture a body cavity. The trocar contains a sharpened obturator tip and a trocar tube or cannula. The trocar cannula is inserted into the skin to access the body cavity, by using the obturator tip to penetrate the skin. After penetration, the obturator is removed and the trocar cannula remains in the body. It is through this cannula that surgical instruments are placed. Specifically, it is through this trocar cannula that surgical stapling instruments with cutting mechanisms are placed. One such trocar is the Endopath® trocar manufactured by ETHICON ENDO-SURGERY Cincinnati, Ohio.

Nonetheless, certain deficiencies in current concepts for endosurgical stapling, cutting, clip applying, and grasping mechanisms have been recognized. One perceived deficiency in current surgical articulating instruments is that when loaded, the articulating head on the instrument tends to move. This movement is usually a combination of piece part reflection and slop (or backlash) in the articulation mechanism. High loads on the distal tip of the instrument (e.g., tissue clamping and staple firing) are reflected through the articulation device into the articulation control near the handle and can move (or rotate) the articulation control mechanism. In the past, articulation joints were designed with the articulation device performing double duty as the means for both positioning and locking the articulated head of the instrument.

An examination of the force application points for the load (tip of the instrument) and the articulation device (near the articulation joint) reveals a mechanical disadvantage for the articulating device. This disadvantage manifests itself as a magnification of tolerances or clearances an the articulating device, resulting in significant head movements.

In existing articulating surgical instruments, the rigid shaft of the instrument is sometimes pivotally connected to the surgical head of the instrument with a pivot mount, such as a pin, hinge, or other joint mechanism. While such mechanisms offer the advantage of a precise, tight bend, this same advantage creates a perceived disadvantage, in that increased transmission force may be required in order to drive a surgical tool, such as a knife, around a tight bend, which force is magnified as the angle of articulation increases.

Wedge sled and knife assemblies are generally known in the art. In general, however, such assemblies are not self-contained within the staple cartridge, rely on more expensive metal, as opposed to plastic wedges, present problems of cutting and stapling in an axis which is not colinear with the shaft, present technical difficulty associated with incorporating a spent cartridge lockout in an articulating joint, do not provide a new knife for each firing, and may not completely contain the sharp edge, of the knife within the cartridge at the initial and final positions of the linear cutting procedure, creating the potential for injury to the user.

A design criteria in creating a system containing two separate mechanisms for clamping and firing tissue is the limitation of the human hand. Therefore, it is difficult to properly and conveniently position a pair of triggers or a pushbutton mechanism coupled with a trigger mechanism. Thus, there has been little focus or incentive to create stapling mechanisms whereby the user is capable of operating a stapler with two strokes, unless both can be accomplished in a one-handed operation without moving that hand from the handle of the instrument.

Naturally, it would be desirable to be able to perform these functions in a fully rotational system. This simply allows the user to obtain virtually any angle of approach to the surgical site without having to contort the arm of wrist in order to adequately approach the subject.

Furthermore, it would be advantageous to provide the capability to remotely articulate the surgical, e.g., clamping and stapling end of the instrument, such that the angular orientation of the end of the instrument may be adjusted even after the instrument has been inserted through the cannula.

It is also desirable to have distal contact of the stapling jaws, and then proximal clamping. "Distal contact" means that the distal or far end of the anvil seats first on-the gap spacing pin or cartridge. Without such distal contact, the surgeon may still be uncertain about the amount of tissue clamped, and therefore the firing force necessary to fire the mechanism. In this way, once distal contact is effectuated, the surgeon realizes and can actually visualize, through an endoscopically placed camera, the amount of tissue clamped between the jaws. Also, distal contact helps prevent tissue from slipping out of the jaws during a clamping sequence.

Additionally, it would be advantageous to provide a knife assembly that included a safety feature, whereby following a cutting sequence, the knife retracts or otherwise is shielded from the operator of the instrument, reducing the likelihood of an inadvertent cutting of the patient or the operator.

Also, it would be highly desireable to provide a device for locking the head of an articulating surgical instrument in an articulated position.

Finally, it would be useful to provide an articulation connection having a flexible neck connecting the rigid shaft of the surgical instrument to a surgical head assembly, providing for a smoothly radiused bend, allowing smoother transmission of force around the bend than is possible with sharper bends achieved through an articulation joint.

SUMMARY OF THE INVENTION

It is an object of the invention to provide a stapling mechanism which is able to be used endoscopically, and may also be used in non-endoscopic procedures, and provides both stapling and cutting to the surgical site. It is desired to have tissue clamped between the jaws of the stapling mechanism, and it is also desired that the stapling mechanism accomplish this clamping and then firing in a two-part, sequenced operation.

It is further an object to provide a stapling and clamping mechanism whereby the clamping mechanism causes the stapling mechanism to be put into position for firing.

This novel concept also necessarily requires that one is prevented from actuating the firing mechanism before clamping is accomplished. Therefore, it is further an object to prevent firing of the stapling mechanism before the entire clamping procedure is completed or if a cartridge is missing or has been previously fired.

It is further an object to provide a rotational mechanism which accommodates stapling and cutting endoscopically.

It is further an object to provide a closure mechanism so that the closure mechanism is not able to inadvertently spring open before the firing mechanism has been fully actuated. It is yet another object to provide a mechanism which allows forward and reverse motion of a clamping trigger such that forward motion causes clamping, and then permits stapling, and reverse motion permits the jaws of the mechanism to be opened, by reversing the functions of the clamping mechanism.

Yet another object is to provide a mechanism for remotely articulating the clamping and stapling portion of the instrument, before, during, and/or after completion of the surgical procedure.

It is an object to provide a closure mechanism in a surgical stapler which accomplishes clamping of the tissue to be stapled in a direction opposite that of stapling, that is, from the distal toward the proximal end of the stapler. In this way, proper amounts of tissue may be adequately clamped, and then stapled.

It is yet another object of the invention to provide a safety feature for retracting or otherwise shielding the knife of the instrument from the patient and operator prior to and/or following the cutting sequence. It is a further object of the invention to provide an instrument which can cut and staple in an axis which is not colinear with the shaft, to provide a self-contained cartridge/wedge assembly to be used in conjunction with the handle, to provide lower cost materials of construction, such as plastic, for use in wedges for only one firing, and to keep the head length of the cartridge to a minimum.

It is a further object of the invention to provide a disposable cartridge assembly which completely encases the firing wedges and knife, such that the knife and wedges do not return to their start positions at the end of a firing sequence.

It is another object of the invention to provide an improved device for locking the head of an articulating surgical instrument.

Finally, it is an object of the invention to provide an improved articulation connection comprising a flexible neck, allowing for a relatively large bend radius and consequent smooth transmission of forces around the bend.

These and other objects of the invention are described in an improved surgical instrument, such as an endoscopic stapling mechanism which is capable of clamping, stapling and cutting tissue. The stapling mechanism utilizes a surgical stapling cartridge which contains at least two double rows of staples. The stapling cartridge also provides for knife means to divide the two double rows of staples during the stapling function. The stapling mechanism contains a trigger mechanism which contains a double trigger feature. One of the triggers causes clamping of tissue. The other trigger causes firing of the staples and actuation of the knife. Thus, clamping and firing are accomplished separately. Because the system contains a safety mechanism, there cannot be firing of staples before there is full clamping of tissue. In this mechanism, stapling is accomplished in any rotatable position, as soon as tissue has been clamped. Yet, the clamping trigger locks in position so that it will not inadvertently spring open during use of the firing trigger.

In one of the embodiments described herein, there is contained in the endoscopic stapling mechanism a double clutch mechanism which allows the user to derive benefits from both forward and reverse motion of the clamping and firing triggers. During forward motion of the triggers, there is clamping and then firing. During reverse motion, there is the capability of overriding any jams encountered by the stapling mechanism, and then allowing the stapled tissue to be removed from the stapling site.

Furthermore, in this invention there is the capability of having distal clamping of tissue, wherein relatively larger tissue is held within a larger size device. After this clamping, there is then proximal contact of the stapling and closure means and thereafter, similar proximal contact of the knife mechanism. Thus, while it is easily ascertainable how much tissue is clamped between the clamping mechanisms, it is also easy to determine whether clamping and stapling have been properly accomplished.

In a highly preferred embodiment of the invention, a mechanism for remotely articulating the stapling and clamping portion of the surgical instrument is provided, including an articulating coupling device, which may be, for example, a ball-in-socket type coupling, a knuckle joint, a flexible neck, a flexible band or strap, a hinge and pin coupling, a rack and pinion, or other coupling device. In a most highly preferred embodiment, a joy stick mounted proximately to the handle allows rotational motion of the joy stick to be translated into articulational motion of the stapling and clamping portion about the aforementioned articulating coupling.

In another highly preferred embodiment of the invention, the knife mechanism retracts within the staple cartridge at the completion of the cutting sequence, and in a most highly preferred embodiment, separates from the knife/wedge driver and is retained, retracted, in the staple cartridge, which is removed and disposed of, to be replaced by a new staple cartridge having a new knife, which may be driven by the same knife/wedge that remains in the instrument.

In yet another highly preferred embodiment of the invention, an improved locking mechanism for redirecting or eliminating deflection in the head of articulating surgical instruments is provided. The locking mechanism may be independently controlled with respect to the articulating mechanism, or operationally connected to the articulating mechanism. The locking mechanism locks the head of the assembly in an articulated position whenever the articulation control is not being used. That is, the articulation lock is generally engaged, disengages when the articulation control is being used, thereby allowing articulation of the head, and relocks the head in its new articulated position when the articulation step is completed.

Finally, in yet another, highly preferred embodiment of the invention, a flexible neck connection is provided for articulating a surgical head assembly with respect to a rigid shaft to which the head assembly is mounted. The flexible neck may be a flexible material with a plurality of ribs therein, which may be articulated with push/pull techniques, or may comprise a pre-articulated neck that assumes a curve as it is advanced through a linear shaft.

These and other objects of the invention will be better understood from the following attached Detailed Description of the Drawings, when taken in conjunction with the Detailed Description of the Invention.

DETAILED DESCRIPTION OF THE DRAWINGS

FIG. 1 is a side elevational view of an endoscopic linear stapling and cutting mechanism of the present invention;

FIG. 1a is an exploded perspective view of the instrument of FIG. 1;

FIGS. 2a and 2b are cross-sectional views of the view of FIG. 1;

FIGS. 3 and 3a are individual and closeup views of the closure trigger of the present invention;

FIGS. 4 and 7 are operational views of the closure trigger and toggle linkage of the invention;

FIGS. 5 and 6 are isolated side and top views of the firing trigger of the invention;

FIGS. 8 and 8a are side and bottom isolated views of a typical cartridge of the invention;

FIGS. 9b, 9c and 9d are side operational views of the interaction between the stapler shaft, the cartridge, and the anvil closing mechanism;

FIG. 10 is a side isolated view of the knife means with a lockout notch;

FIG. 10a is a side view of an alternate knife means with no lockout notch;

FIG. 11 is a side isolated view of the lockout member contained in the cartridge of FIGS. 8 and 8a.

FIGS. 11a and 11b show the motion of the lockout member of FIG. 11 when moved by the knife means of FIG. 10 in the cartridge of FIG. 8;

FIG. 12a is an exploded perspective view of the instrument of FIG. 12

FIG. 14 is a side view of the closing trigger plate of the embodiment as described in FIGS. 12 and 13;

FIG. 15 is a side view of the firing trigger as seen in FIG. 13 of the present invention;

FIG. 15a is a side view of the trigger return linkage of the alternate embodiment of this invention;

FIGS. 16 and 16a are isolated views of the front toggle link as seen in FIG. 13 of the present invention;

FIGS. 17 and 17a are isolated plan views of the rear toggle link as also described in FIG. 13 of the present invention;

FIGS. 18 and 18a are isolated side and top views of another typical cartridge, as used in the stapler of FIG. 12;

Figure 12:
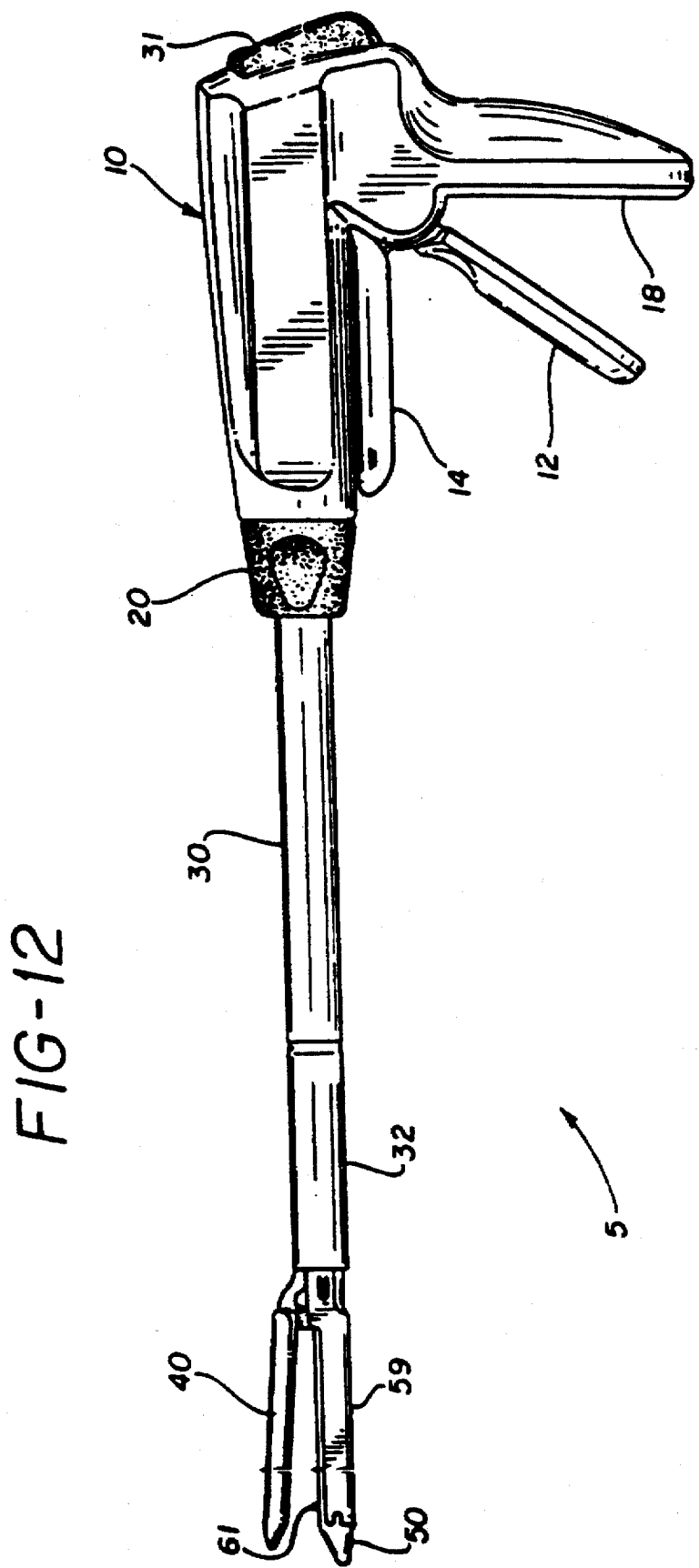
FIG. 12 is a side elevational view of an alternate preferred embodiment of the stapler of the present invention.
Figure 13:
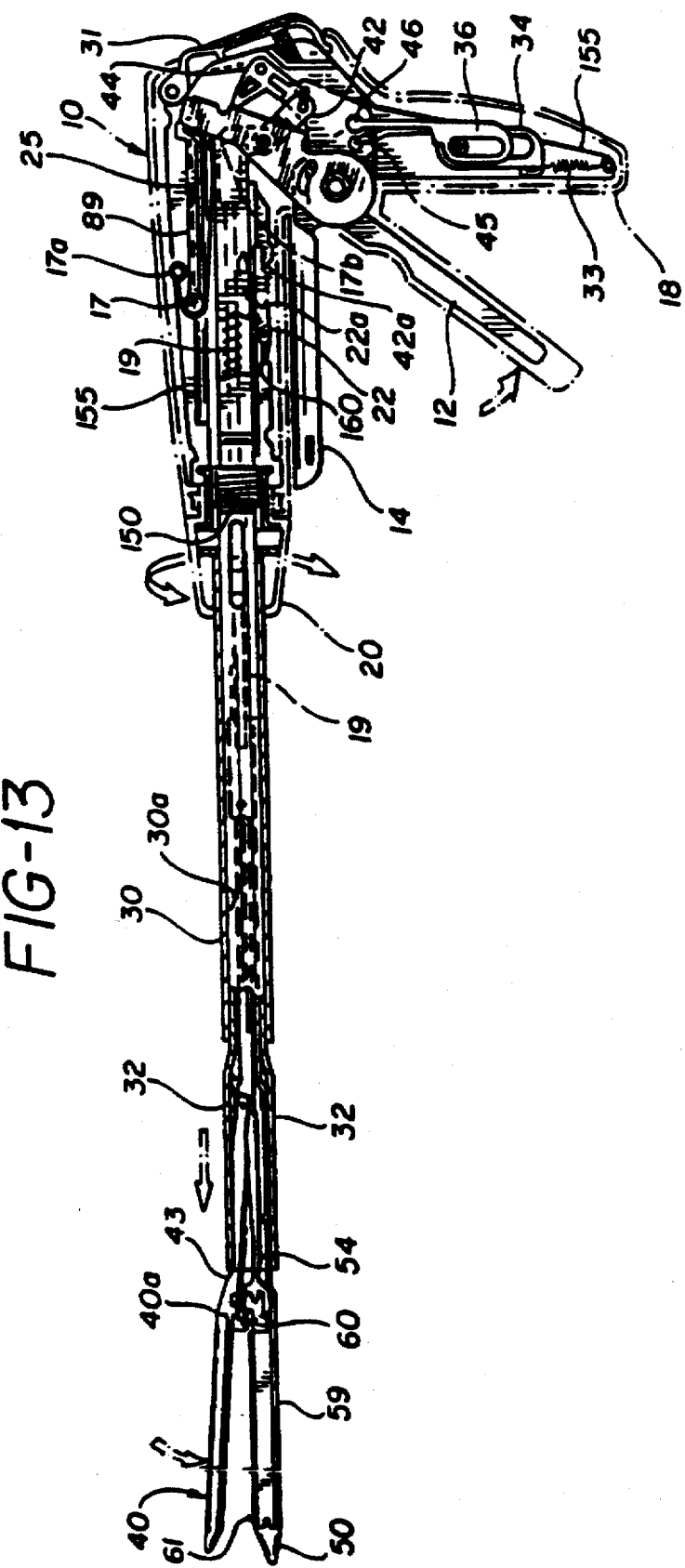
FIG. 13 is a cross-sectional view of the stapler of FIG. 12.
Figure 19:
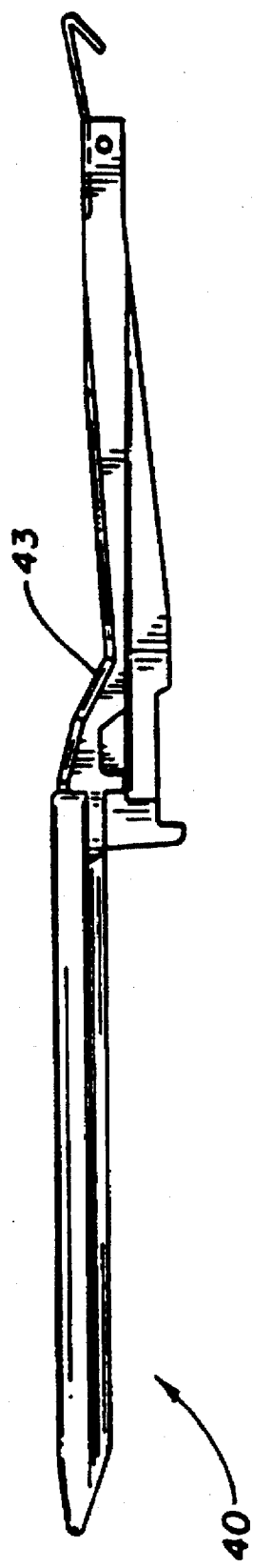
FIGS. 19 and 19a are isolated side and bottom views of the anvil member used in the stapler of FIG. 12.
Figure 19A:
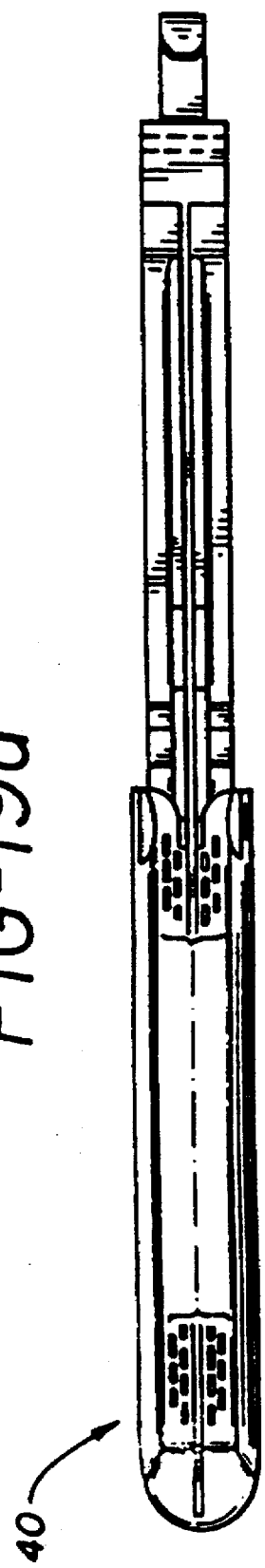

FIG. 20 is a detailed view of the knife mechanism and lockout notch as used in the cartridge of FIG. 18, as seen in the views of FIGS. 12 and 13 describing the 15 alternate embodiment of the present invention; and FIGS. 20a and 20b are views of the lockout mechanism before and after motion of the knife means of FIG. 19 as in the stapler of FIGS. 12 and 13.

FIGS. 21a and 21b are sectional views of a preferred staple cartridge of the invention, showing the retractable knife in its retracted "start" position in FIG. 21a, and its retracted end position in FIG. 21b.

Figure 22:
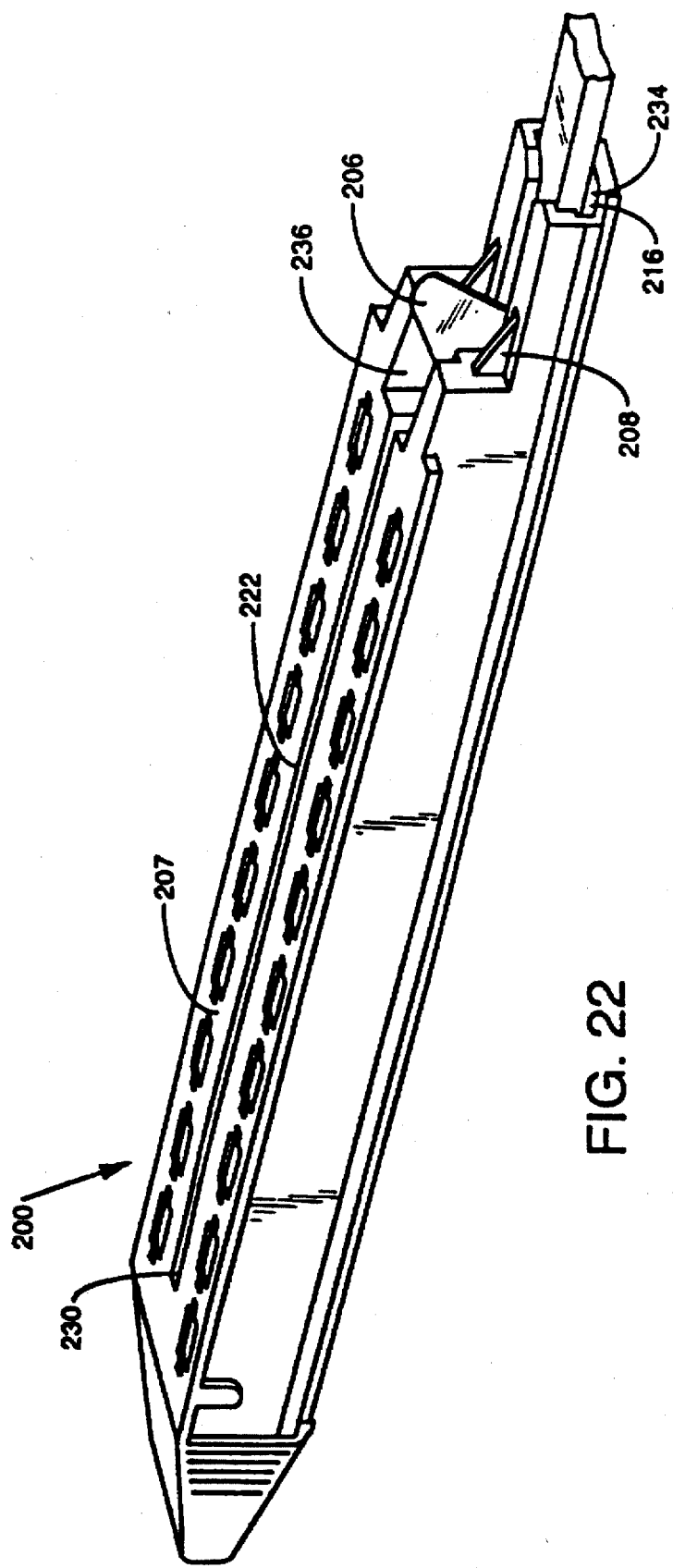

FIG. 22 is an isometric view of a preferred cartridge of the present invention.

Figure 23:
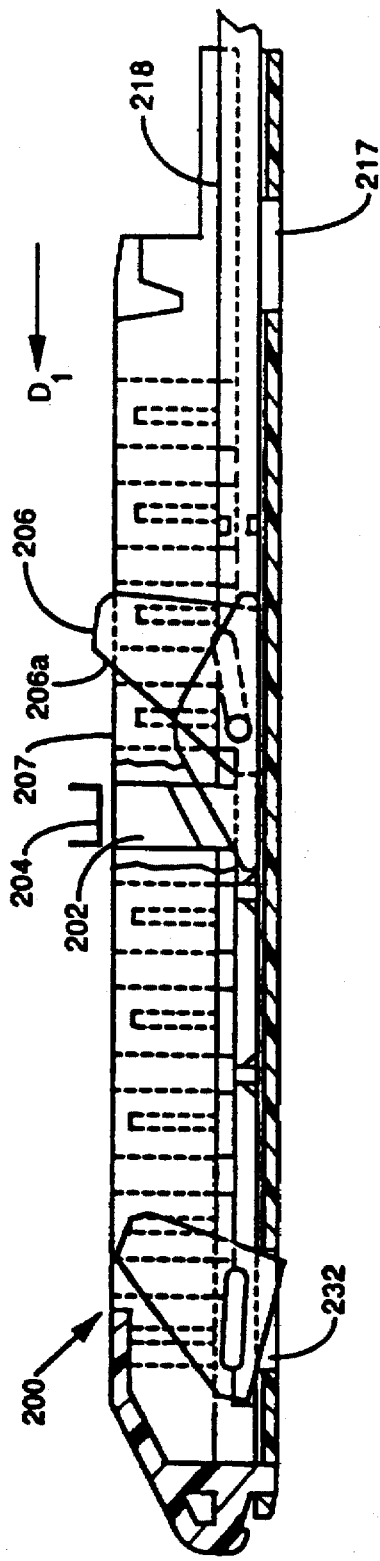

FIG. 23 is a cross-sectional view of a preferred staple cartridge of the invention, showing the retractable knife in its cutting position.

Figure 24:
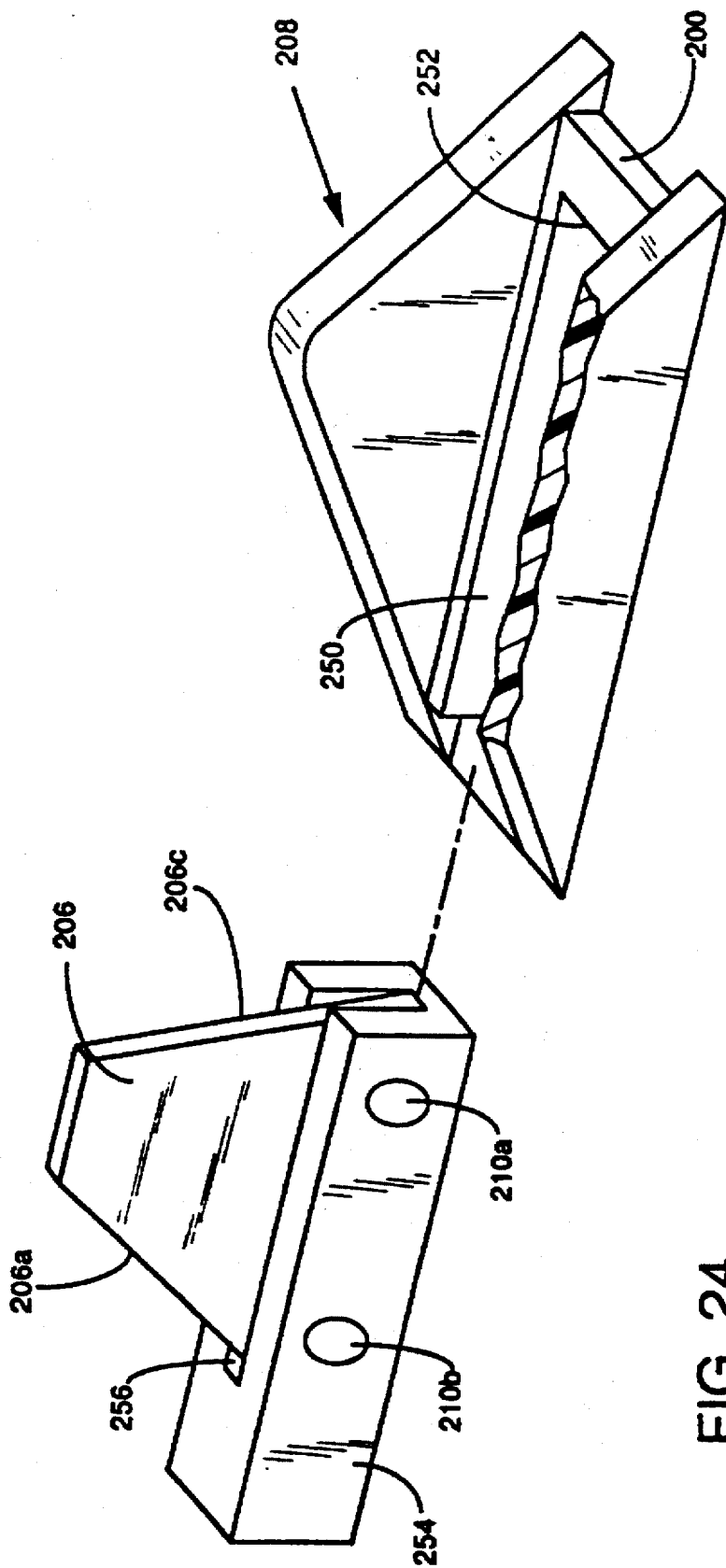

FIG. 24 is an isometric view of a knife/wedge decoupling assembly for use in a preferred embodiment of the invention.

Figure 25:
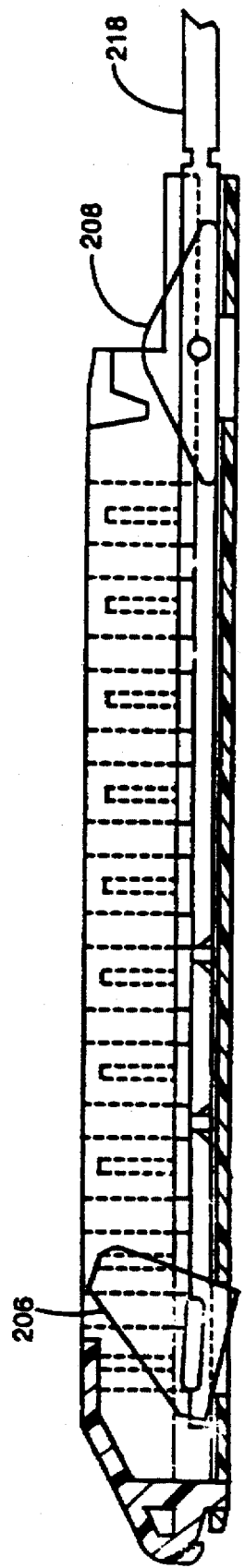

FIG. 25 is a cross sectional view illustrating a knife decoupled from a wedge in a preferred embodiment of the invention.

Figure 26:
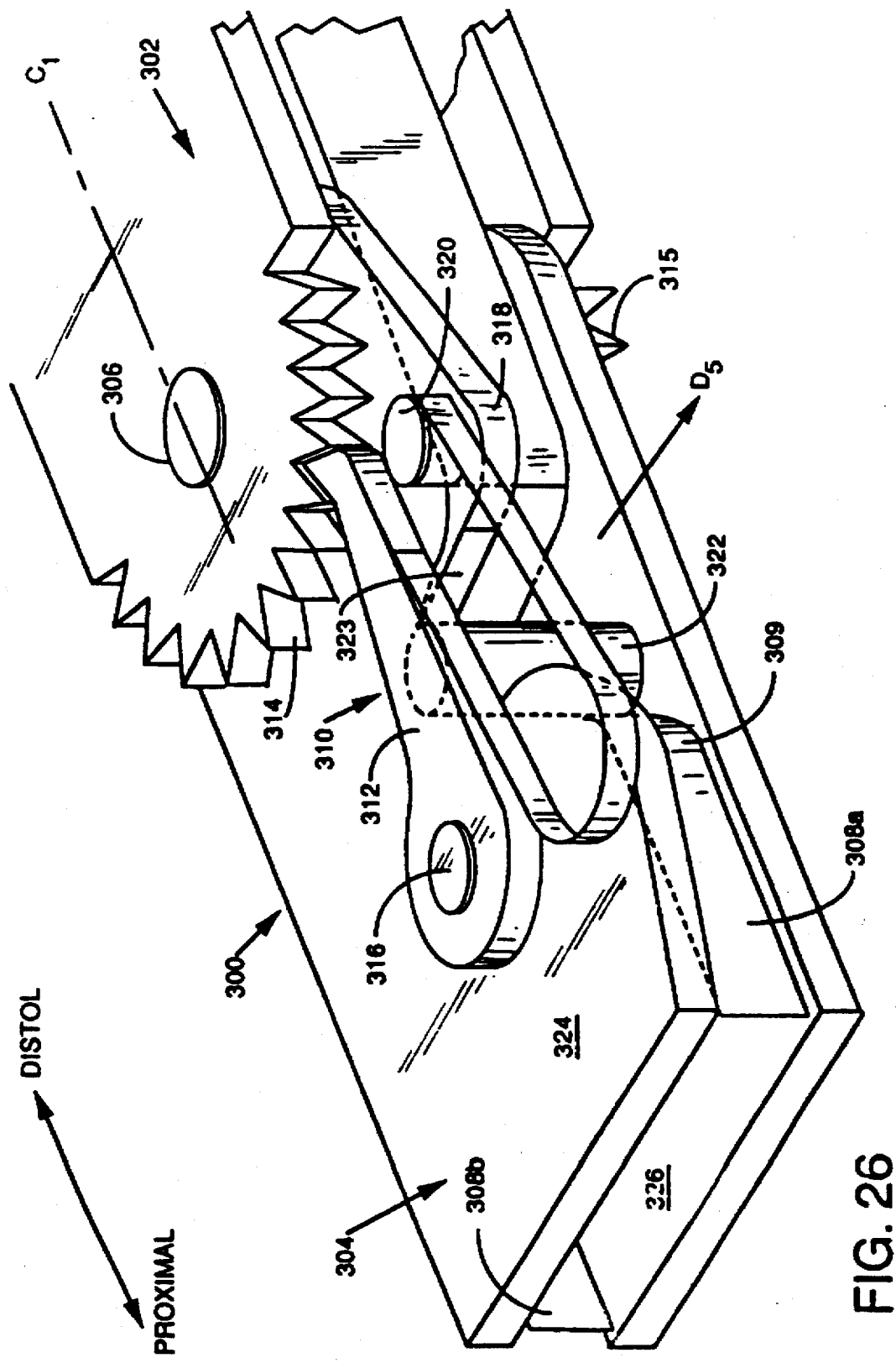

FIG. 26 is an isometric view, partially broken away, of a preferred articulation locking device of the present invention.

Figure 27:
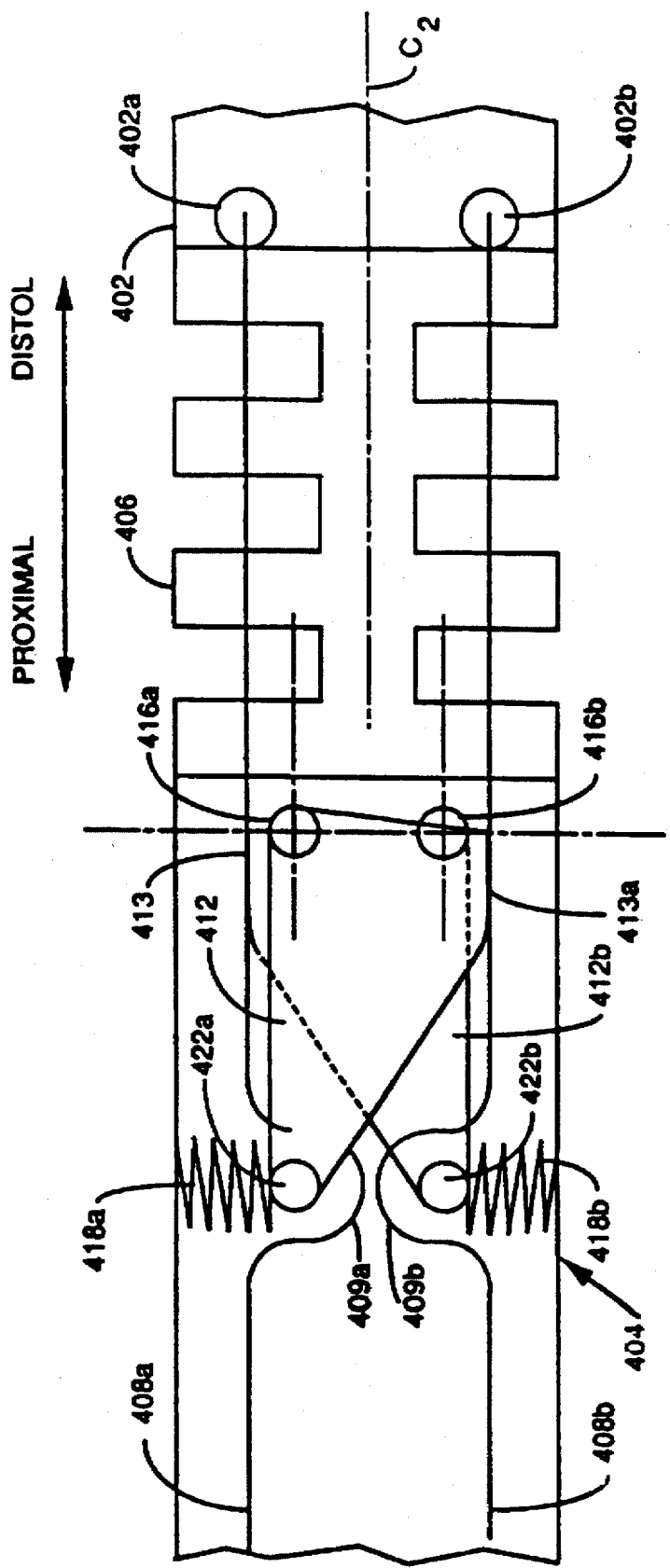

FIG. 27 is an overhead view of another preferred articulation locking device of the present invention.

Figure 28A:
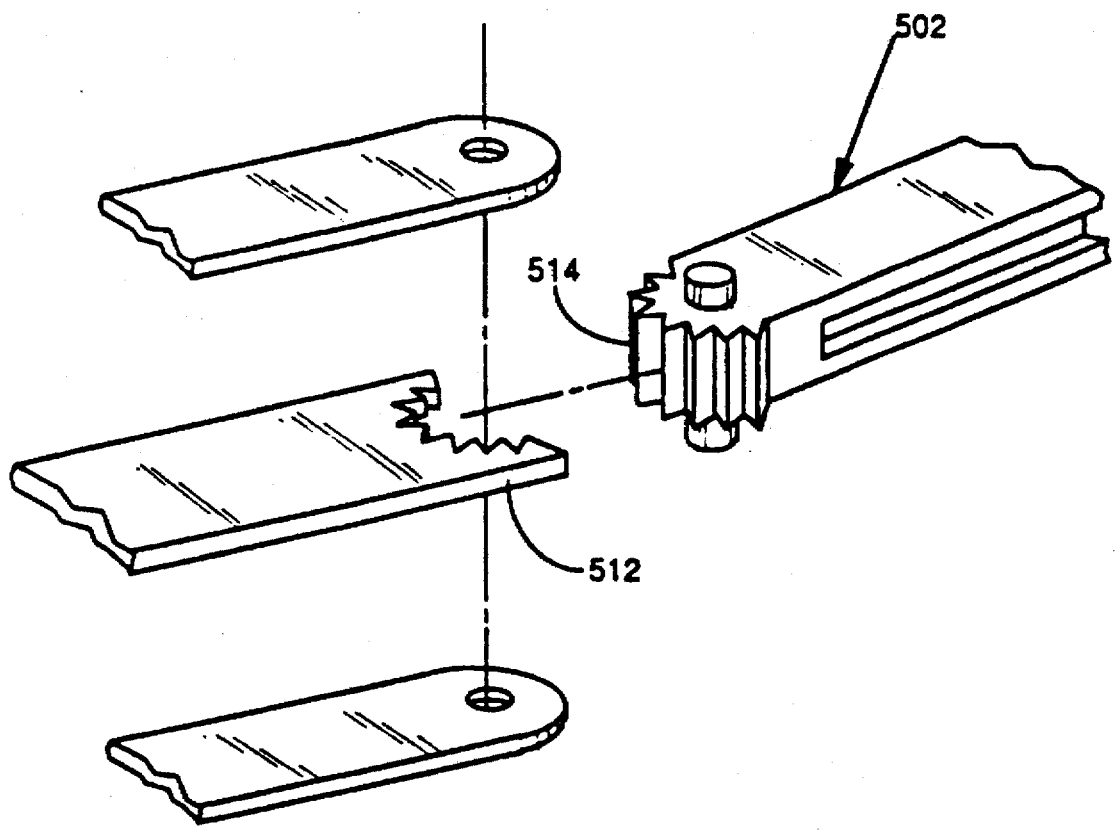
Figure 28B:
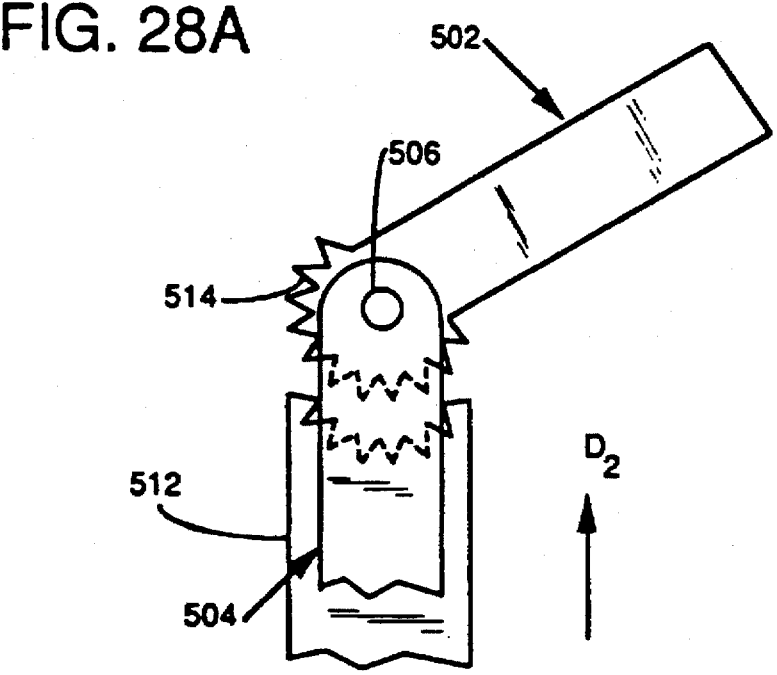

FIG. 28A is an isometric view of another preferred articulation locking device of the present invention FIG. 28B is a top plan view of the device of FIG. 28A.

Figure 29:
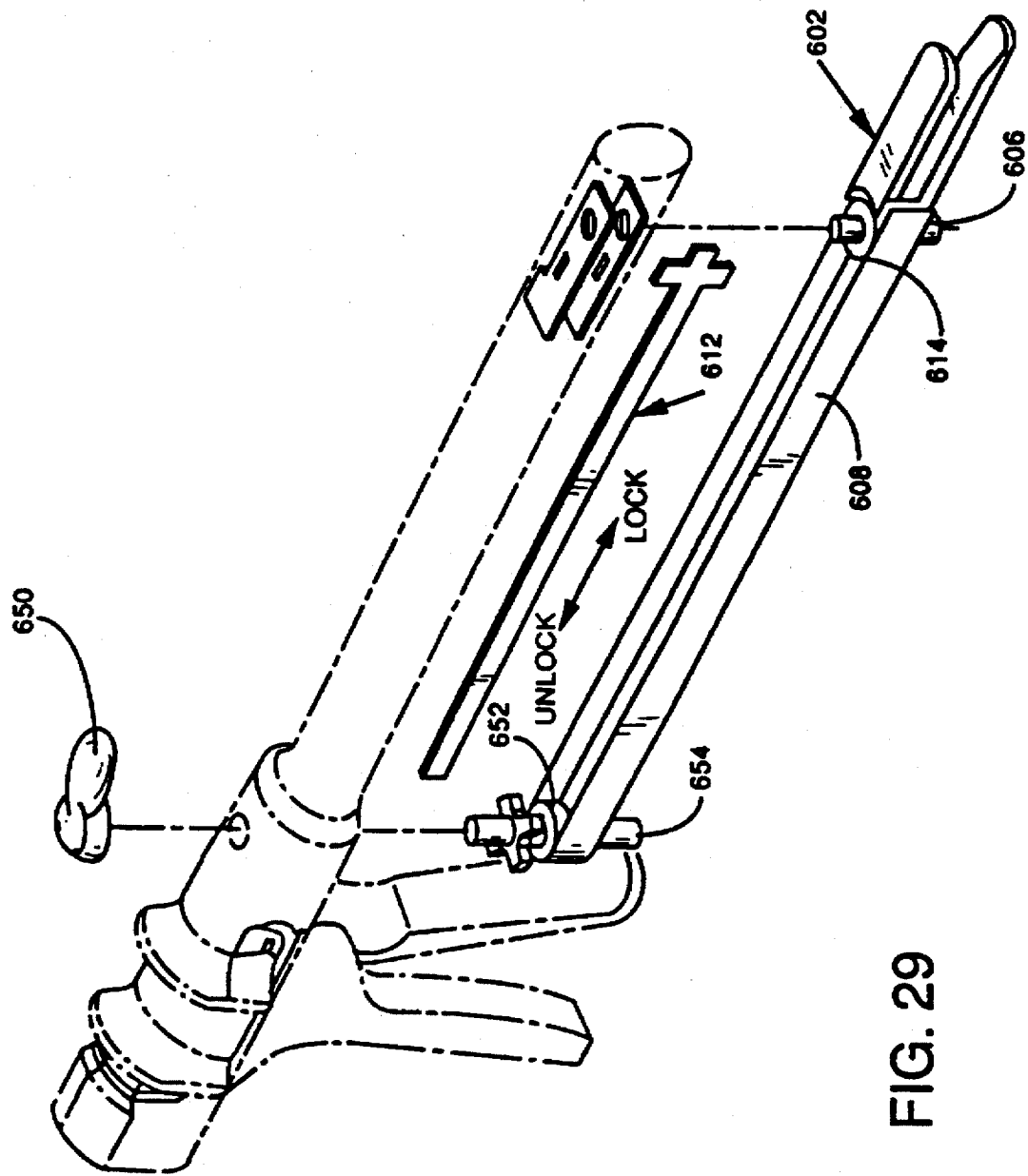

FIG. 29 is an isometric, exploded view of another preferred articulation locking device of the present invention.

FIG. 29A is a top plan view of the distal end of the device of FIG. 29, showing the head in a locked unarticulated position.

FIG. 29B is a top plan view of the distal end of the device of FIG. 29, showing the head in an articulated position, and the locking device in an unlocked position.

FIG. 29C is a top plan view of the distal end of the devices of FIG. 29, showing the head in a locked articulated position.

Figure 30:
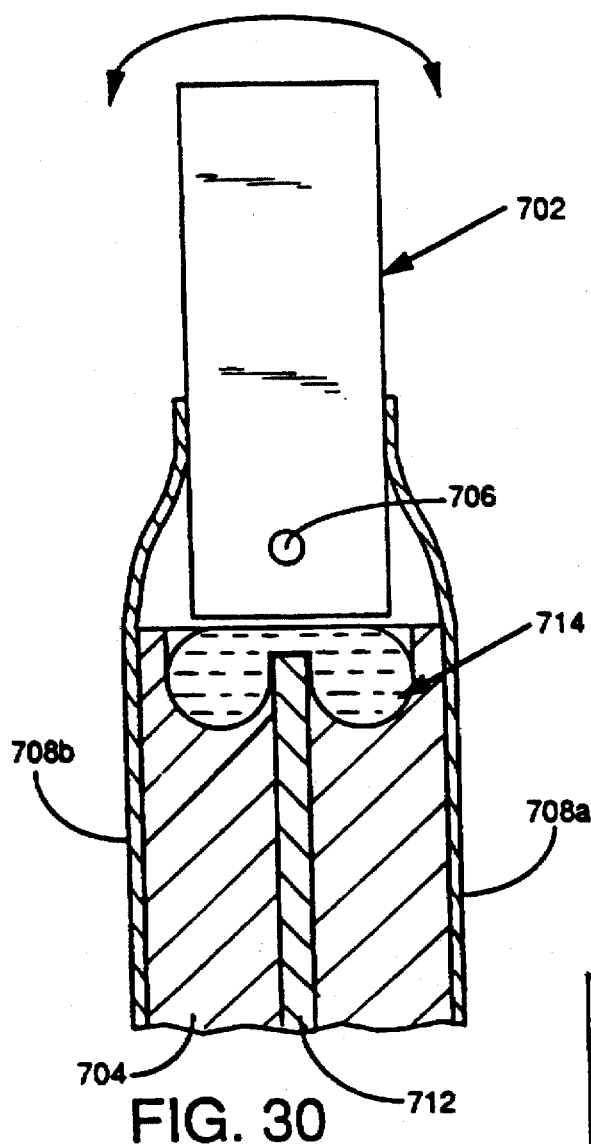

FIG. 30 is a top plan view, partially broken away, of another preferred articulation locking device of the present invention, illustrated in an unarticulated mode.

Figure 30A:
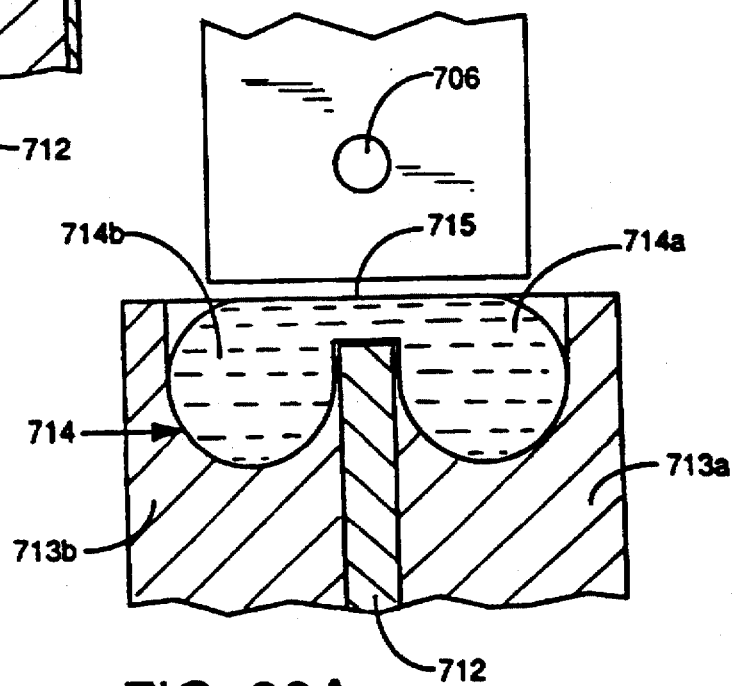

FIG. 30A is a close up view of a portion of the device of FIG. 30, showing the locking device in greater detail.

FIG. 31 is a top plan view of the device of FIG. 30, illustrating the locking device in an articulated mode.

FIGS. 31A and 31B are schematic representations of the "valving" function performed by the locking device of FIGS. 30 and 31.

FIGS. 32A and 32B are schematic illustrations of a preferred anvil closure mechanism of the present invention having a closure tube.

Figure 33:
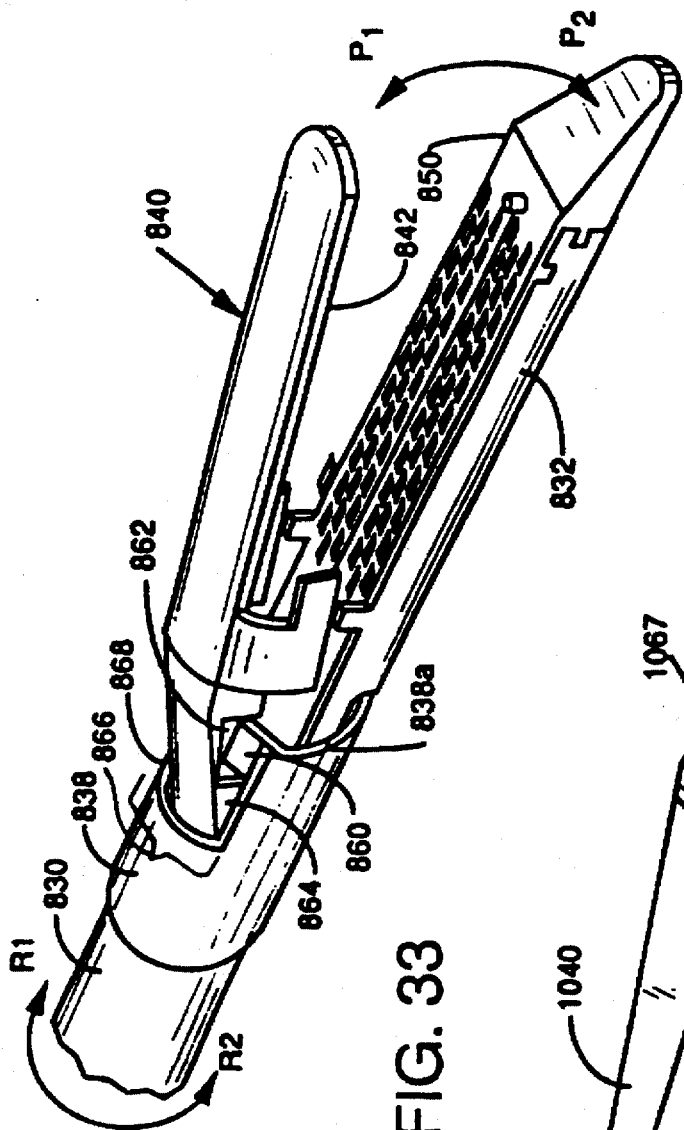

FIG. 33 is an isomeric view of a preferred anvil closure mechanism of the invention having a closure tube.

Figure 34C:
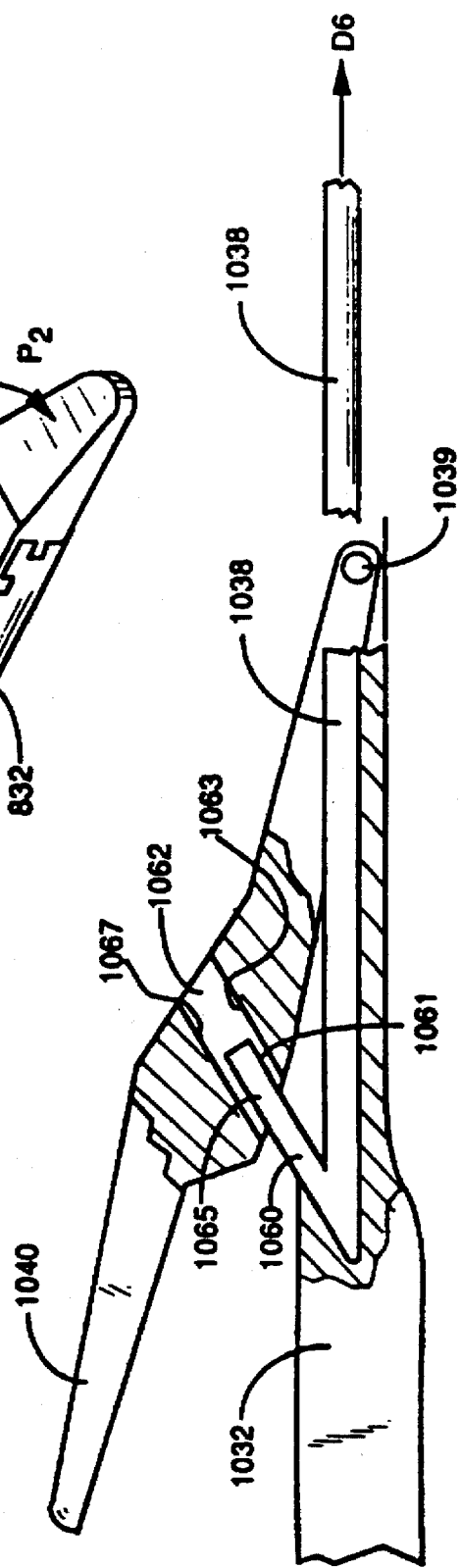
Figure 34A:
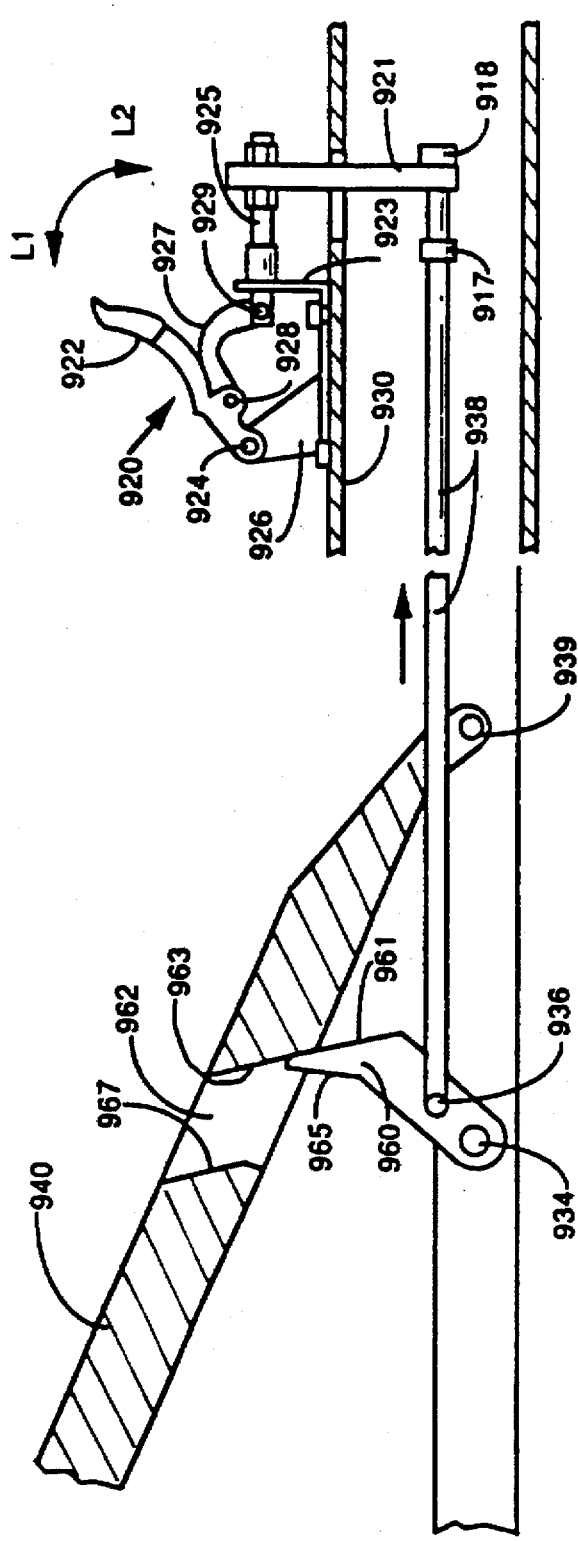
Figure 34B:
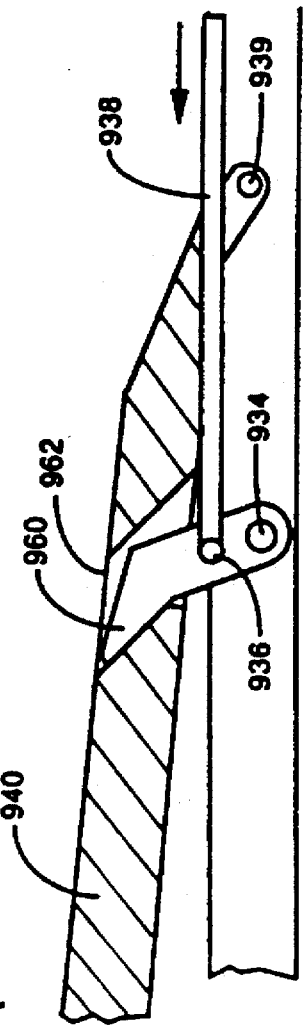

FIGS. 34A and 34B are schematic illustrations of a wedge anvil closure mechanism of the present invention in the open and closed position, respectively.

FIG. 34C is a schematic illustration of another wedge anvil closure mechanism of the present invention.

Figure 35:
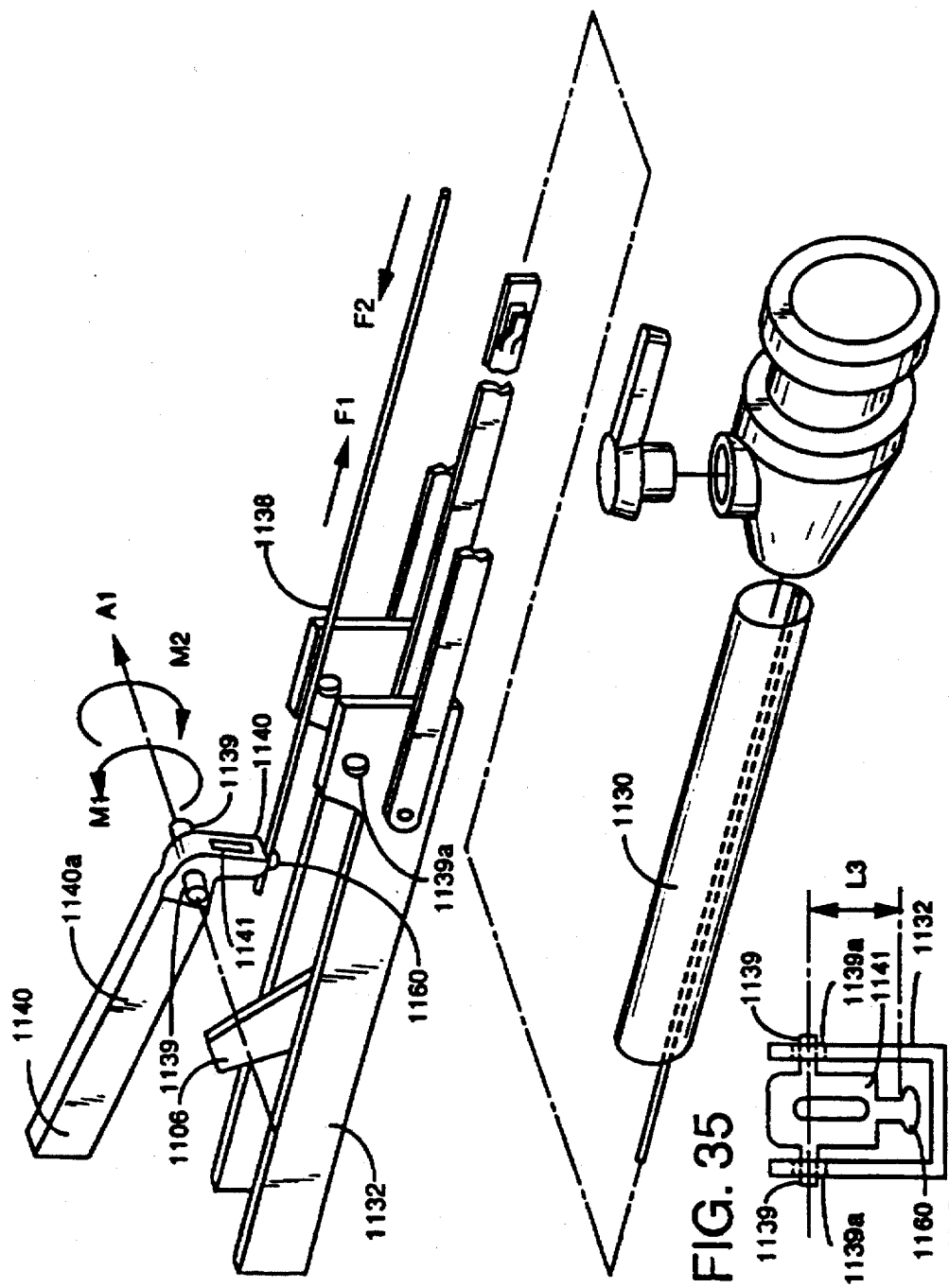

FIG. 35 is an exploded isometric view of another anvil closure mechanism of the present invention.

Figure 35A:
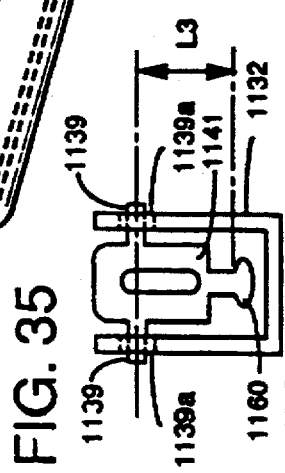

FIG. 35A is an end elevation view of the anvil of FIG. 35.

Figure 36:
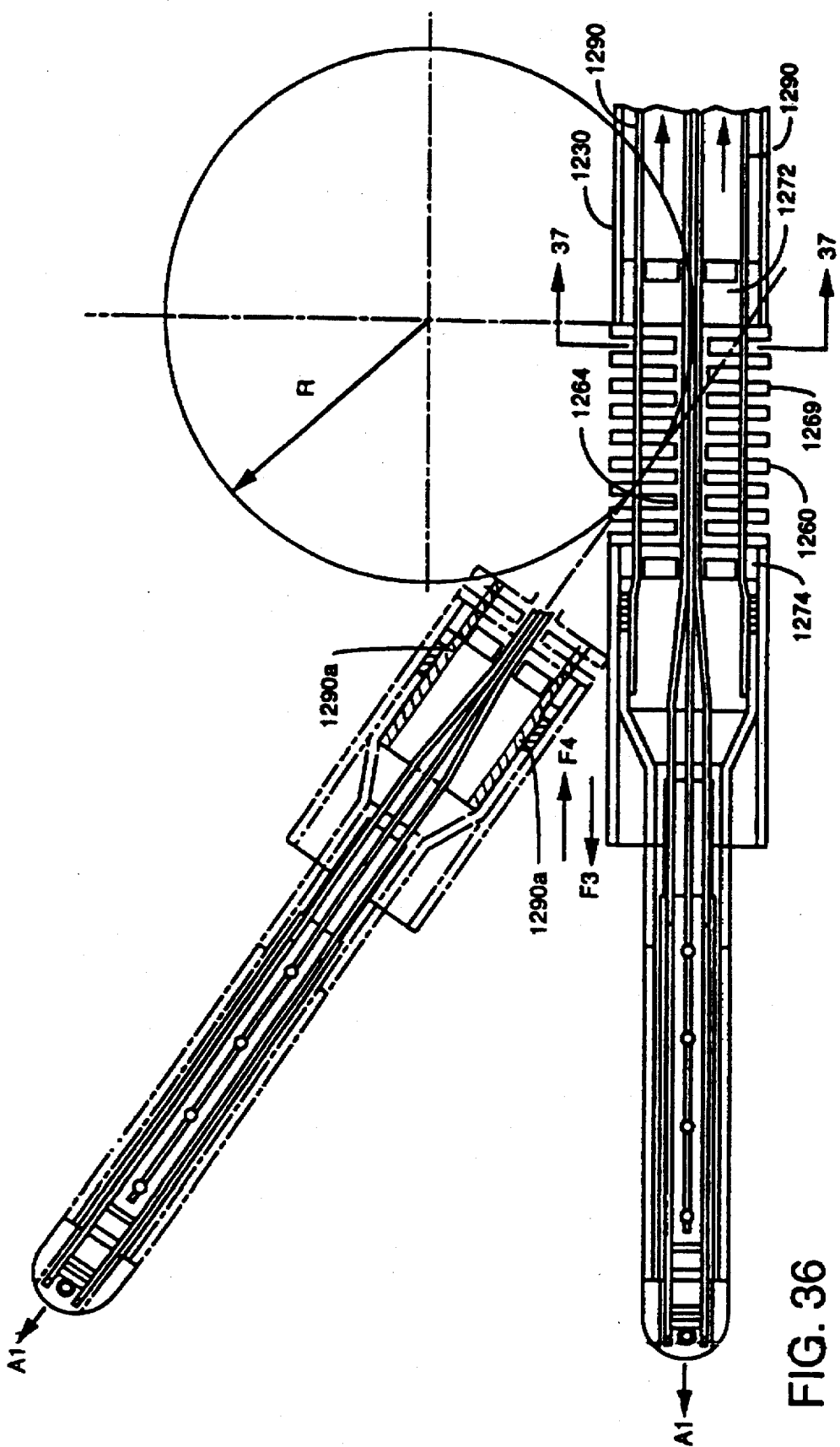

FIG. 36 is a cross-sectional top plan view of a preferred embodiment of a flexible neck of the present invention.

FIG. 36a is a schematic illustration of a variable bend radius flexible neck of the present invention.

FIG. 37 is a cross-sectional view, taken along lines 37—37 of FIG. 36, rotated 90°, of a preferred flexible neck of the invention.

FIG. 38 is a side elevational view of the top half of the flexible neck of FIG. 37.

Figure 39:
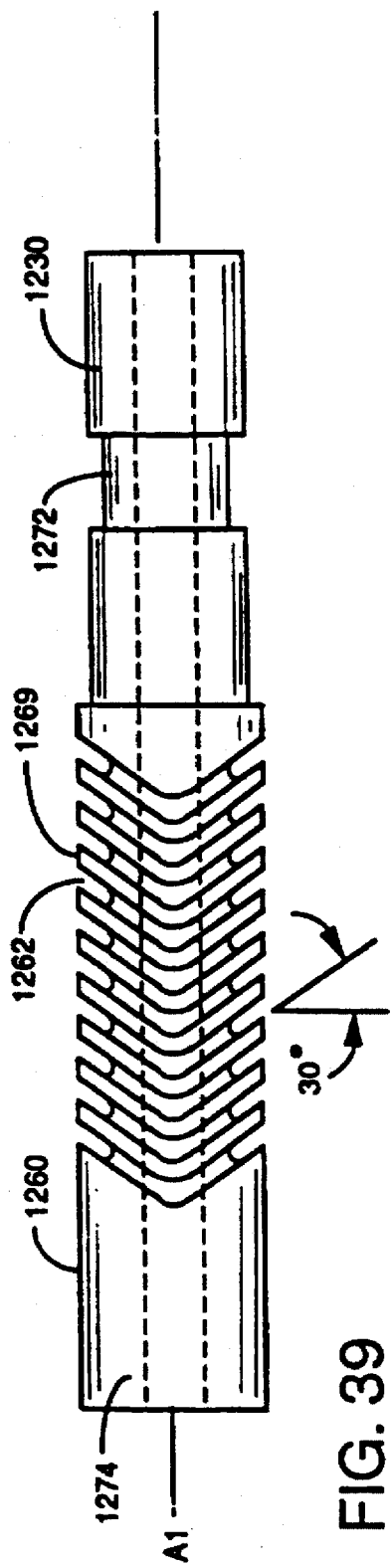

FIG. 39 is a bottom plan view of another preferred embodiment of a flexible neck of the present invention having a "herringbone" shaped series of kerfs.

Figure 40:
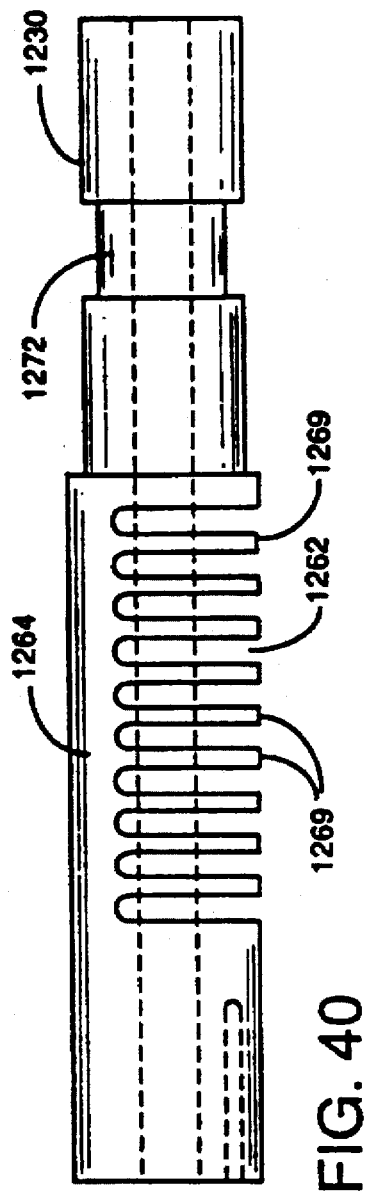

FIG. 40 is a side elevation of the flexible neck of FIG. 39.

Figure 41:
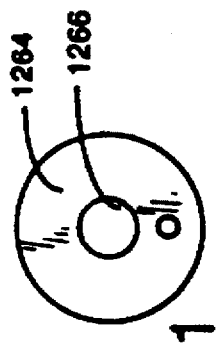

FIG. 41 is a left side view along lines 41—41 of FIG. 40.

Figure 42:
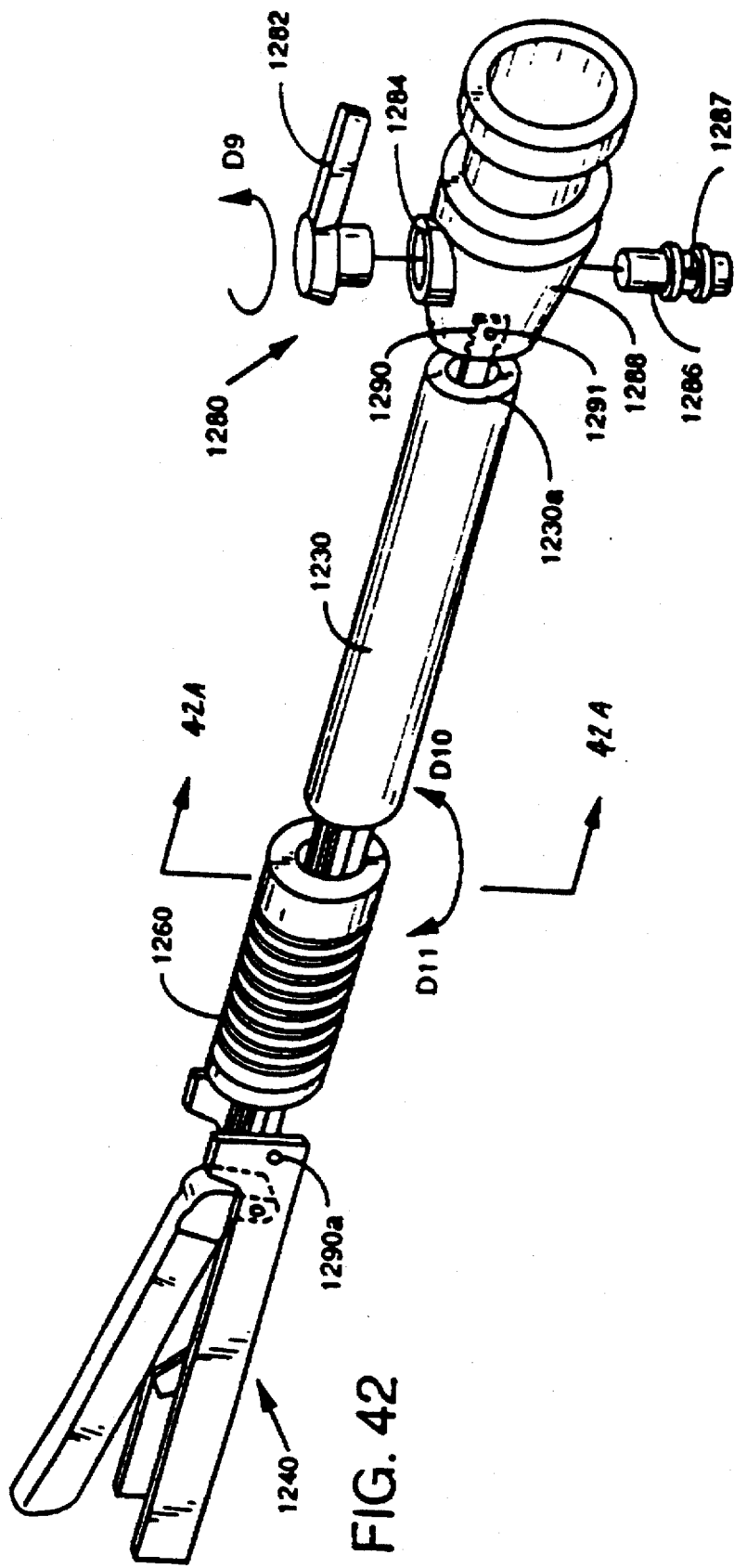

FIG. 42 is an isometric view of the distal portion of a preferred surgical instrument of the invention.

Figure 43A:
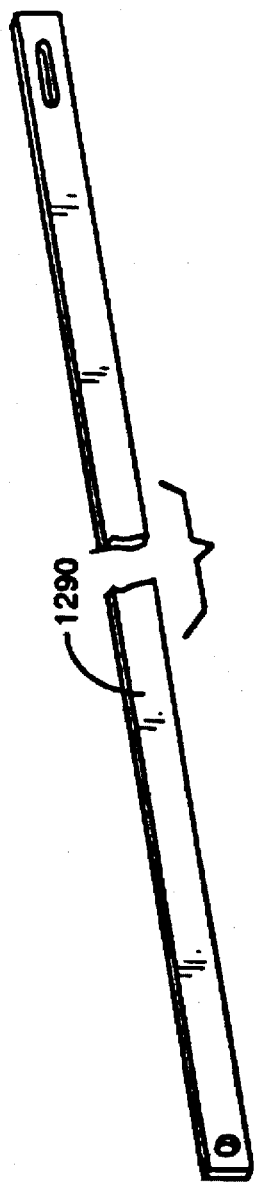
Figure 43B:
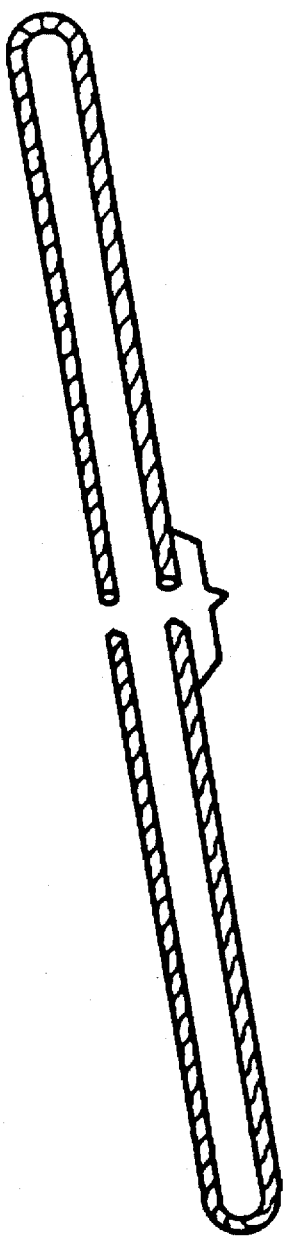
Figure 43C:
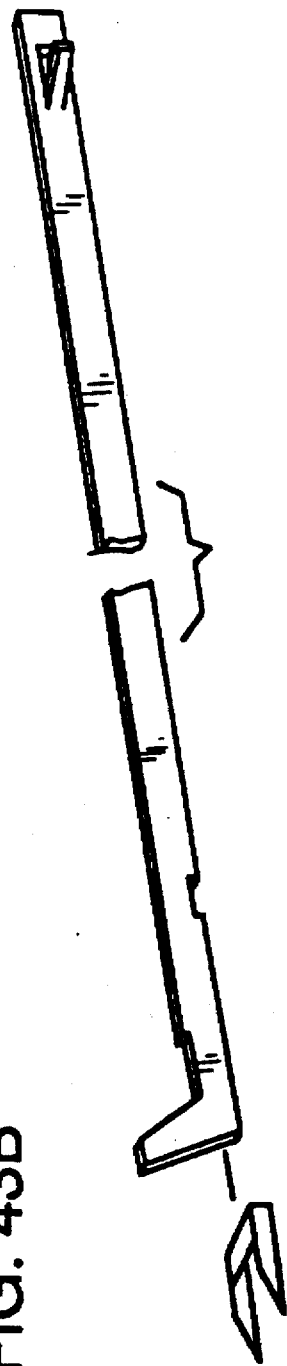

FIGS. 43A–43C are a series of tools and mechanisms that may be slidably received by the flexible member of the instrument of FIG. 42.

Figure 44:
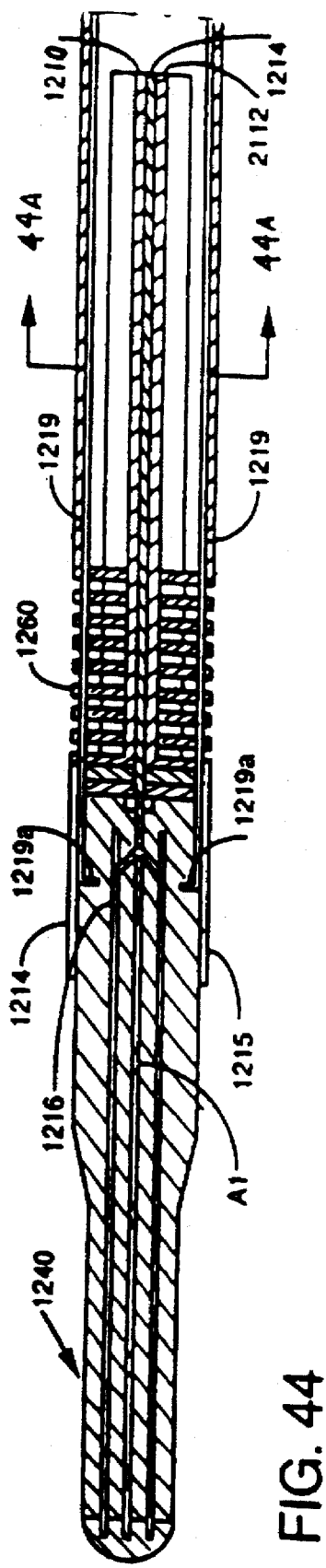

FIG. 44 is a cross-sectional view of another preferred flexible member of the present invention.

Figure 44A:
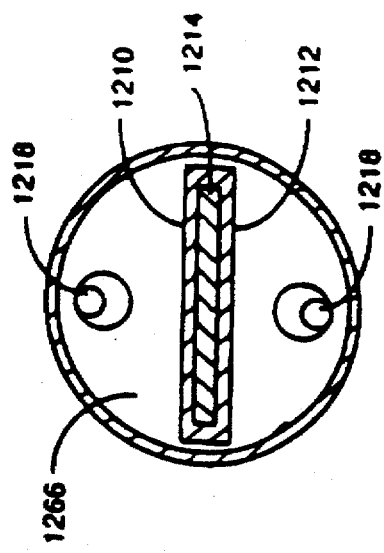

FIG. 44A is a cross-sectional view of the flexible member of FIG. 44 taken along lines A—A.

Figure 45:
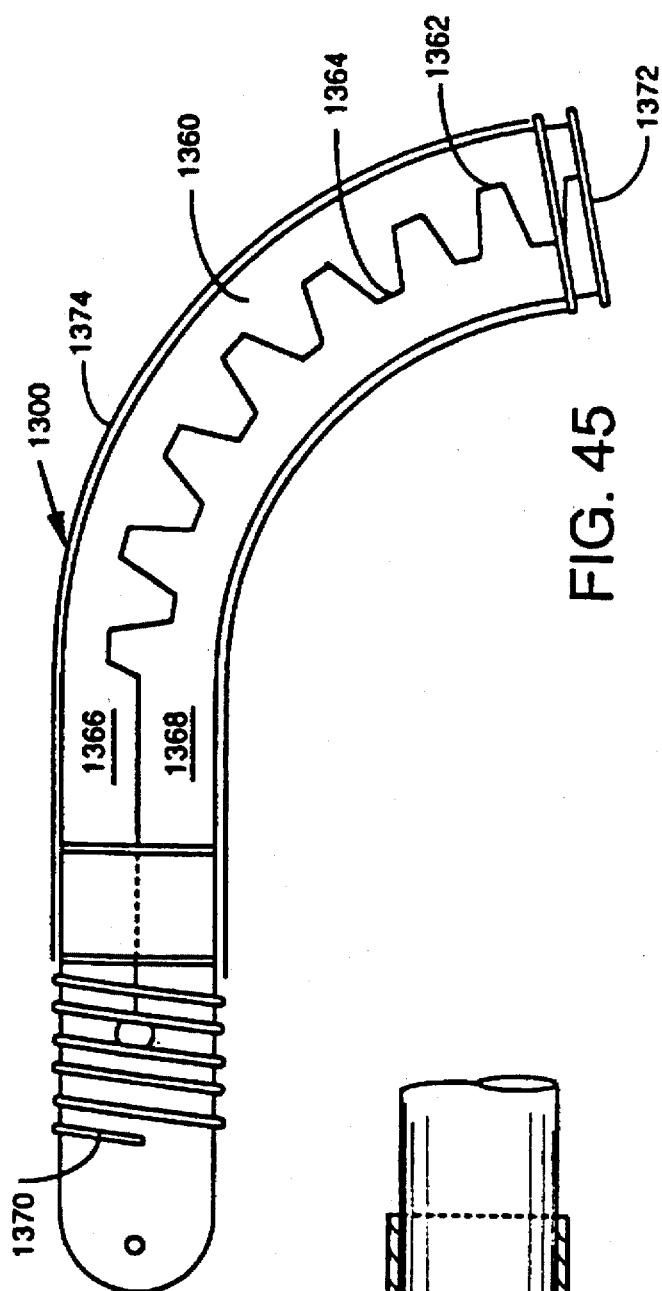

FIG. 45 is an elevational view of another flexible member of the present invention, shown in a flexed orientation.

Figure 46:
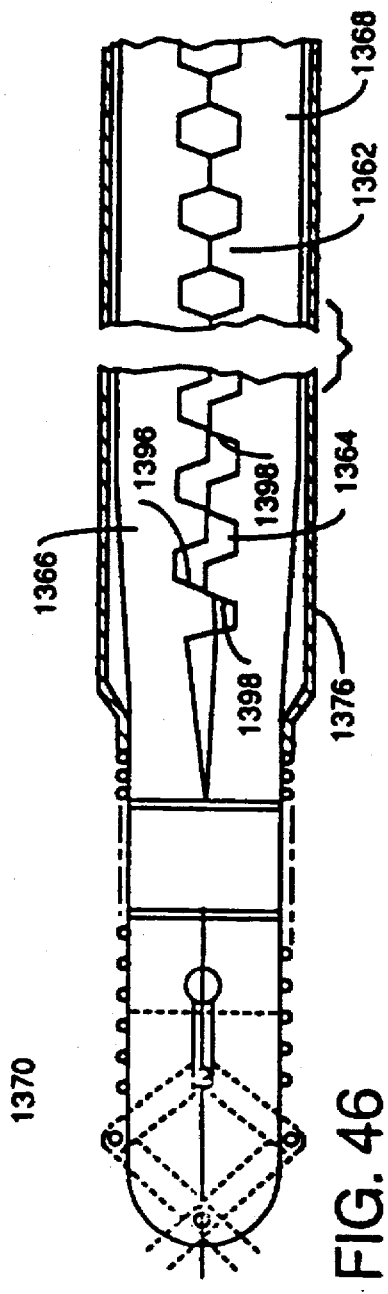

FIG. 46 is an elevational view of a flexible member of the present invention shown in a straight orientation.

Figure 47:
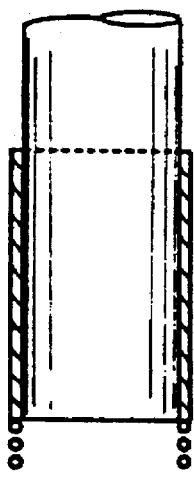

FIG. 47 is an elevational view of an outer tube used to straighten and/or cause the curvature of the flexible members of FIGS. 45 and 46.

Figure 48:
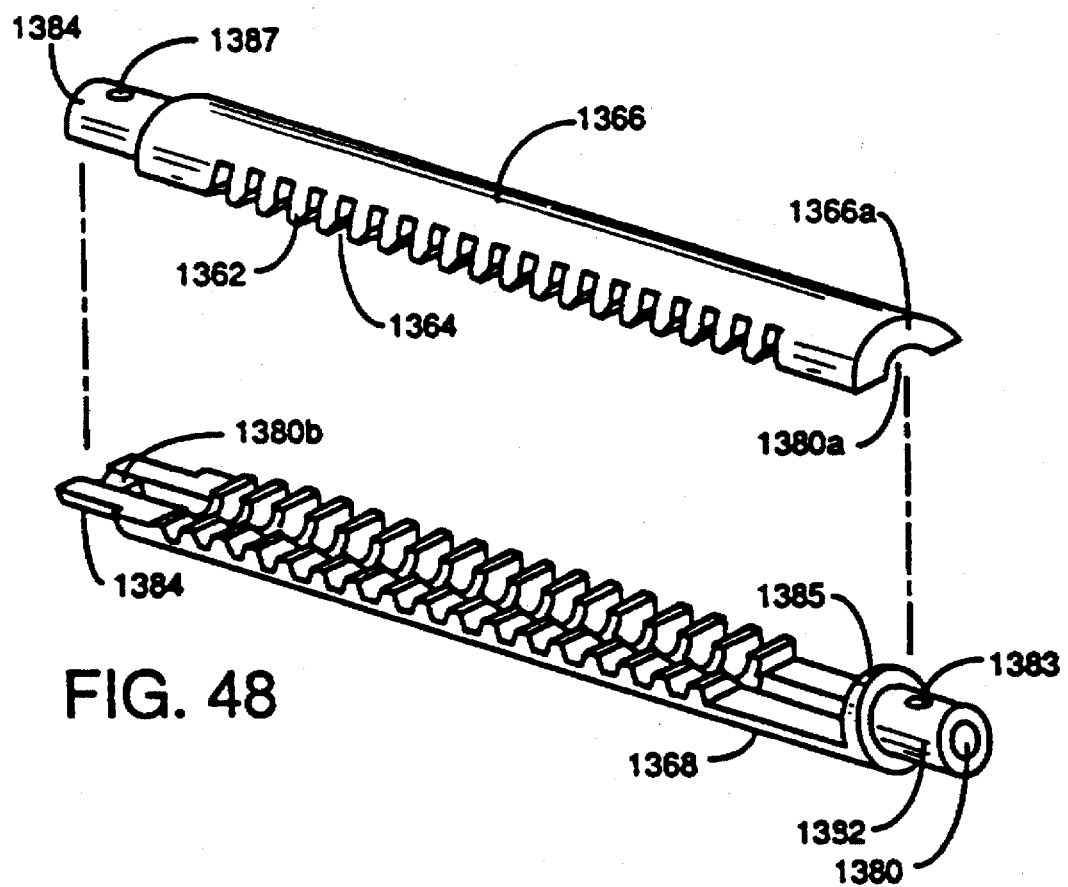

FIG. 48 is an isometric exploded view of the flexible member of FIG. 46.

Figure 49:
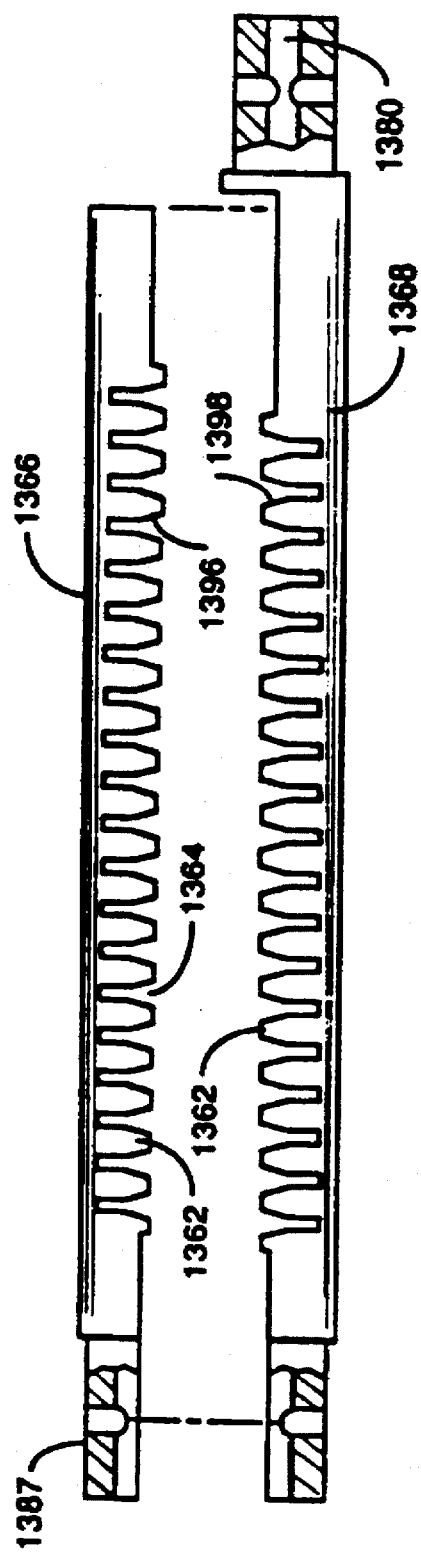

FIG. 49 is an elevational, cross sectional view of the flexible member of FIG. 48.

Figure 49B:
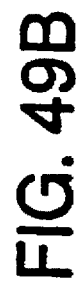
Figure 49A:

FIG. 49A is a cross sectional view taken along lines A—A of the embodiment illustrated in FIG. 49.

FIG. 49B is a cross sectional view taken along lines B—B of the embodiment of FIG. 49.

Figure 50:
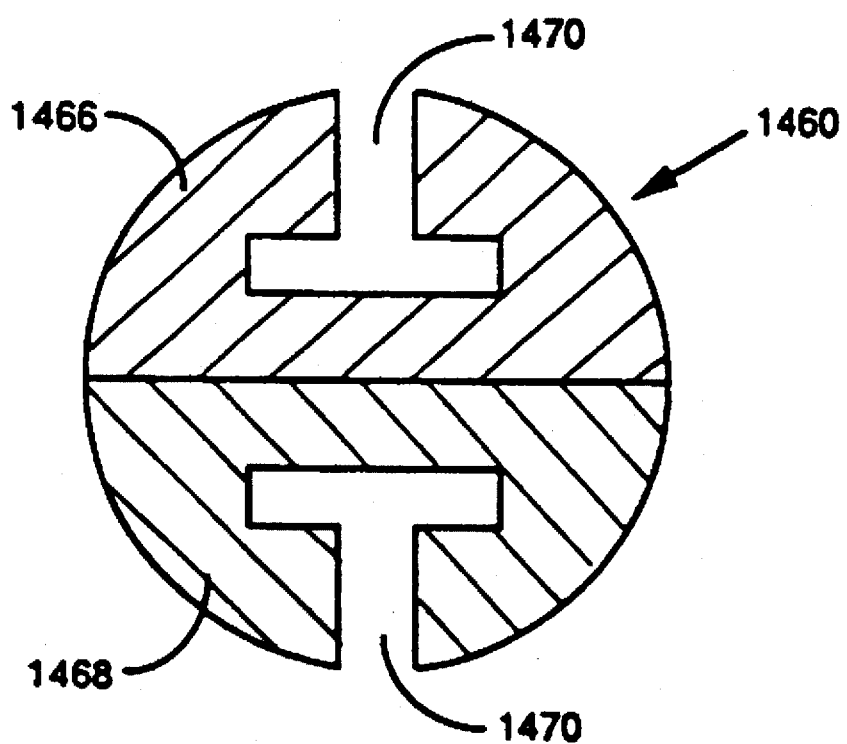

FIG. 50 is a cross sectional view of another preferred flexible member of the present invention.

DETAILED DESCRIPTION OF THE INVENTION

As can be seen from FIGS. 1, 1a, and 2, in one embodiment of the surgical stapler of this invention, there is described a stapler 100 which contains a handle portion 110, rotating means 120, a shaft portion 130, anvil portion 140, and cartridge assembly 150. A knife means 160 is slidable within the cartridge assembly 150 to cut tissue. In the handle portion 110 there is a first or closure trigger (also called a clamping trigger) 112, and second or firing trigger 114. The clamping trigger 112 causes the anvil portion 140 to come into proximity of the cartridge assembly 150. The firing trigger 114 causes the wedges 122 located in the shaft 130 to move through the cartridge assembly 150, and also causes the knife means 160, also located in the shaft 130 to move through the cartridge assembly 150, in order to cut tissue.

As can be seen in more detail in FIGS. 1a, 12a, 2b, 3, 4, 5, 6 and 7 the endoscopic linear stapling mechanism 100 contains a double trigger mechanism. The first or clamping trigger 112 is for closing the jaws 132, 142 of the instrument onto tissue, and the second or firing trigger 114 is used for firing the stapler 100. The intent of the double trigger design is to combine one-handed use within a stapling mechanism, and to make such one-handed use so that it is impossible to form staples unless the instrument is fully closed.

When the instrument is initially loaded, with cartridge assembly 150 held within shaft portion 130 on jaw 132, the firing trigger 114 is flush with the body 116 of the instrument, so that it is parallel with the shaft portion 130, and is for all practical purposes inaccessible to the user. During actuation of the clamping trigger 112, the firing trigger 114 swings into a "ready" position preparatory to actuation. This position is 35° to 45° spaced apart from the closure trigger 112, which has now moved into position against base 118. As will be later described, a multiplier mechanism causes the firing trigger 114 to move through a greater arc than closure trigger 112.

The closure trigger is spring-loaded, so that an incomplete closure results in the closure trigger swinging open to its position as seen in FIGS. 1 and 2, once again spacing the staple firing trigger 114 away from the reach of the hand operating the mechanism. A closure sequence must therefore be completed, with the clamping trigger 112 locking proximal to the base 118, before the firing trigger 114 can be grasped or is, operational by the user.

As can be seen from the FIGS. 1a, 2, 3, 3a, 4 and 7, the closure trigger 112 is attached to a front closure link 124, at pivot pin 126. Closure trigger 112 is also attached to a rear closure link 128 which pivots inside the handle 110 of the stapler 100. The closure trigger 112 therefore is capable of pivoting around the handle portion at pivot 113, so that it moves roughly 25°–50°, in this instance, preferably 35°. The closure trigger 112 is spring-loaded at spring 129 so that unless the closure trigger 112 is fully rotated toward the base 118, the spring 129 causes the closure trigger 112 to reopen to its initial position. As will be later explained, it is the motion of this closure trigger 112 which causes the anvil portion 140 to clamp into proximity of cartridge assembly 150.

Furthermore, the closure trigger 112 is connected by means of a pin to the firing trigger 114. Thus, as can be best seen in FIGS. 2b, 3, 5 and 6, the closure trigger 112 is linked with the firing trigger 114 by means of a pin 119 which moves in a guided path along slot 117 away from the axis of rotation of the closure trigger 112. This pin 119, in turn, moves along a path within slot 117 of the firing trigger 114. As better seen in FIGS. 2b, 5, 6 and 7, the rotation of the closure trigger for approximately 35° results in rotation of the firing trigger for approximately 45°. The control of the pin 119 is accomplished by guide plates placed in the body 116 of handle portion 110. Now, closure trigger 112 is in place at the base 118 of handle 116. Firing trigger 114 needs to travel only 30°–60° to complete a full firing stroke. This arc is quite manageable for even the smallest human hands.

After its initial rotation, this guiding pin 119 no longer acts upon the firing trigger 114. That is, this guide pin 119 is no longer in contact with the firing trigger 114. This allows the firing trigger 114 to complete its rotation and fire staples without interaction of guide pin 119 or with the closure trigger 112. Thereby, the firing trigger 114 is connected to a spring 121 as seen in FIG. 1, which is in turn connected to the handle 110. This spring causes the firing trigger 114 to return to the 45° position so that triggers 112, 114 may be returned during opening of the instrument 100.

Figure 2B:
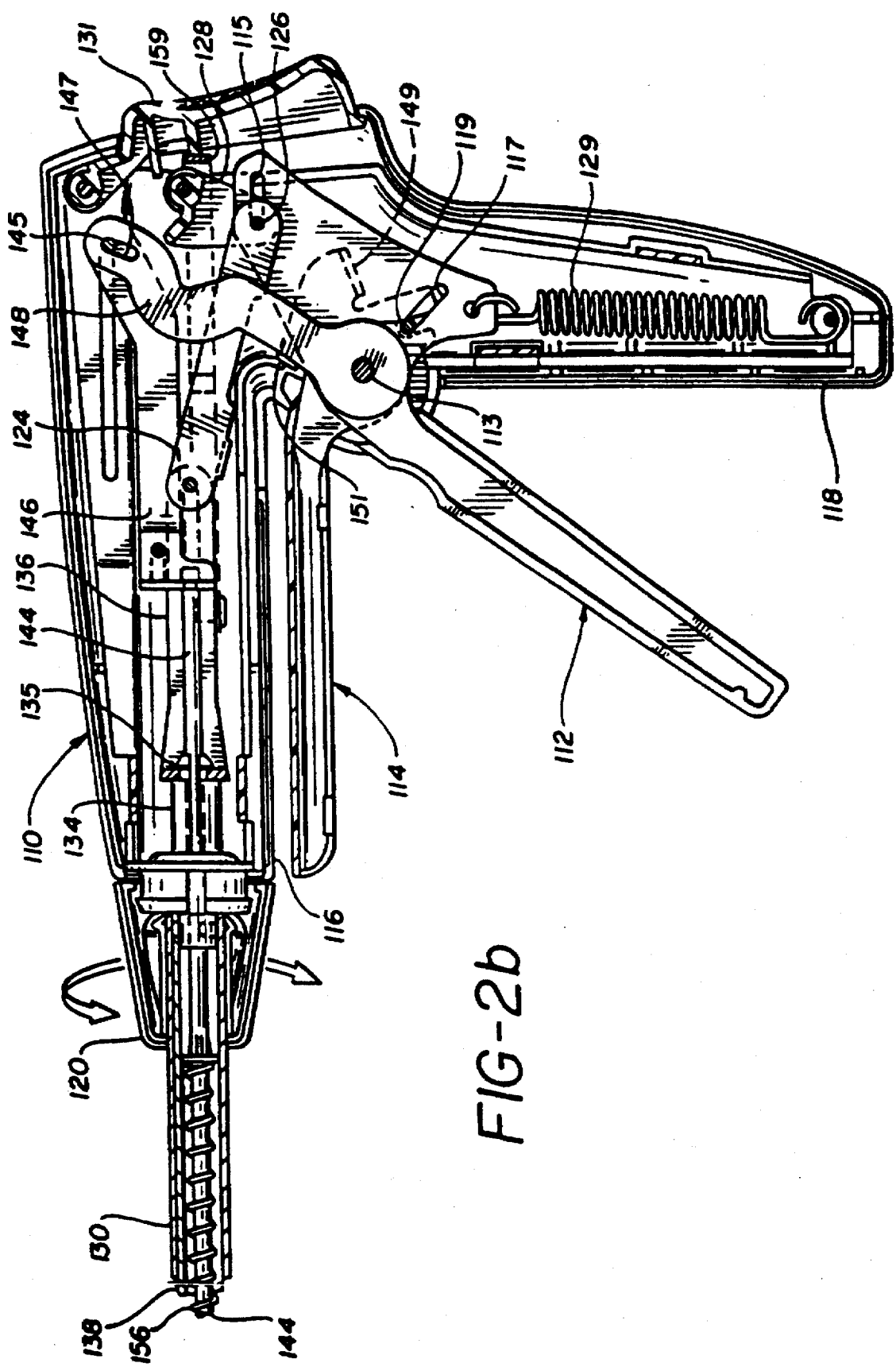
Figure 9:
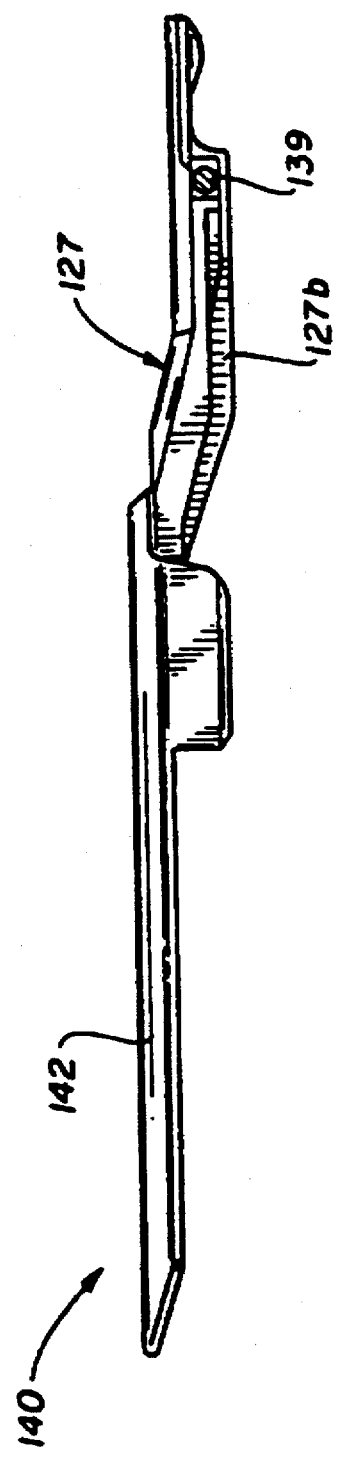
FIGS. 9 and 9a are side and bottom isolated views of the anvil of the invention.
Figure 9A:
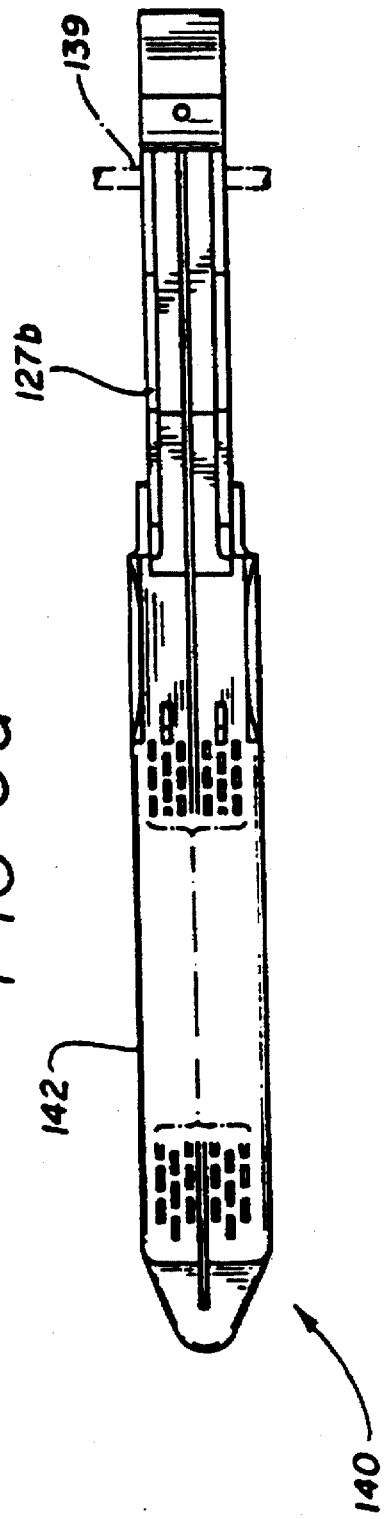

As can be seen in FIGS. 1, 1a and 2b, and especially in FIG. 4, there is contained a locking mechanism comprising button 131 which activates leaf spring involution 159a on leaf spring 159, in order to cause the closure trigger 112 to be locked once it reaches base 118 of the handle 116. The closure trigger 112 is locked in place by leaf spring 159 which seats under front closure link 124 thus immobilizing pin 126. This in turn restrains closure trigger 112. The safety button 131 is pivotally mounted to the proximal top of base 118 and rests upon leaf spring 159. As will later be explained, 30 thereafter, the firing trigger 114 is free to move alone.

As further can be seen from FIGS. 2b, 4 and 7, motion of closure trigger 112 causes motion of front and rear closure links 124, 128. These front and rear closure links 124, 128 cause motion in line with the shaft 130 of a closure sliding member 136. This closure sliding member 136 is attached in a rotatable fashion at joint 135. On the distal side of joint 135 is closure coupler 134, which attaches to the end of a closure channel 138. It is the closure channel 138 which is attached to the pin 139 in the shaft 130 that connects this mechanism to anvil 140.

Closure channel 138 causes closure of the anvil portion 140 into proximity and alignment with the cartridge assembly 150. This is accomplished in that the closure links 124, 128 first move parallel to the axis of the shaft 130, as in FIG. 7, from their original positions in FIG. 4. Closure channel 138 is caused to slide within shaft 130. The front top surface 138a of closure channel 138 pushes forward and down on the anvil. This causes anvil 140 to come parallel to cartridge assembly 150 so that there is alignment of cartridge 150 and anvil 140. The shaft 130 is formed from a stationary tube, so that the closure channel 138 moves within the stationary tube 131 of shaft 130 at the distal end of the instrument 100.

This double trigger mechanism 112, 114 has the following advantages. The firing trigger 112 cannot be actuated until the closure trigger 114 has been completely snapped into its final position, due to locking of the closure trigger 112 inside the handle 110. Therefore, one is certain that tissue has been clamped before the firing trigger 114 has been placed into motion. The firing trigger 114 can be actuated without repositioning the hand following closure of the instrument. That is, the hand stays stationary, and is once again gripped around the firing trigger 114, with closure trigger 112 maintained at the base 118 of the handle 110. This facilitates rapid completion of the firing sequence without requiring the surgeon's attention on the stapler away from the endoscopic video screen and thereby away from the operating arena. In addition, both the closure trigger 112 and the firing trigger 114 utilize a mechanism which is familiar to those who use surgical instruments, a pistol grip with a trigger type actuation.

As has earlier been explained, the closure trigger 112 pushes on the central pivot pin 126 of a toggle linkage 124, 128. Central pivot pin 126 rides in slot 115. This central pivot pin 126 results in relatively large amounts of motion in the closure channel 138 (see FIG. 4) which results in gross closure of the instrument 100. The mechanical advantage provided by the toggle linkage 124, 128 during this portion of closure is relatively small. This has the advantage of providing the user with high tactile feedback. That is, the user is readily able to tell whether the system is overloaded with tissue. Near the position wherein movement of the toggle linkage 124, 128, (FIG. 7) is nearly complete, the closure trigger 112 has moved into place at base 118, and front closure link 124 and rear closure link 128 have been made generally parallel to the shaft 130, relatively little motion of the linkage 124, 128 results from any given rotation of the trigger 112. Trigger 112 rotation at this point provides significantly higher closure force than during the first portion of its motion. This is critical in accomplishing preloading of anvil 140 during the final portion of closure, and is in theory only constrained by the structural limitations of the system.

As can be seen from FIGS. 2b, 5 and 6, firing is accomplished by a simple rotation of the firing trogger 114 acting as a lever arm about pivot 113. The firing trigger is linked to the firing or driver rod 144 and driver rod link 146 by means of firing links 148. These firing links are engaged with the firing triggers by means of a clutch. This clutch mechanism is better seen in the top view of the firing trigger as seen in FIG. 6.

This clutch mechanism does not engage the firing link 148 until the firing trigger 114 is in a "ready to fire" position, whereby hook 149 engages link 148. This eliminates the potential for firing the instrument prior to complete closure of the mechanism by closure trigger 112.

Once the clutch system has engaged the firing link 148, this causes the driver rod link 146 to be translated by pin 145, are moving with link 148 in slot 147, in a generally parallel position to the shaft 130 of the mechanism. This driver rod link 146 is connected to driver rod 144 which is rotatably connected in nozzle 120 to a pusher block 152 contained in the shaft 130. This pusher block is connected to firing wedges 122 and knife mechanism 160, as seen at the proximal edge of the shaft 130 which enters the cartridge assembly 150. The firing wedges 122 are able to transversely move staples loaded in the cartridge assembly 150 so that they are fired into the anvil portion 140, as best seen in FIGS. 2a, 8, 8a, 9 and 9a, and as well known in the art. The knife mechanism 160 is capable of cutting tissue between the completed pair of double or triple rows (or more) of staples, as also is well known in the art.

After firing has been completed, the firing mechanism returns by means of a compression spring 156 placed about driver rod 144 along shaft 130, so that spring 156 is stationary at base 157, which causes the driver rod 144 to be moved in a direction reverse from firing. Spring 156 itself has a sufficient strength to also cause driver rod 144 to move the firing link 148 via linkage 146 to return to its ready to fire position. This similarly causes the driver rod 144 to pull the wedges 122 and the knife 160 so that they are removed from the cartridge assembly 150. If the wedges 122 or the knife 160 do not return, that is if they are jammed, the firing mechanism comprising the firing trigger 114 contains a reverse clutch assembly which allows the firing trigger 114 to engage with the firing link 148 at hook 151 (FIG. 6) so that it is capable of causing this assembly to move in a reverse or rearward direction. This provides a backup to the system, in the event there is a failure in the driver return spring 156 or if the instrument has inadvertently been misassembled.

The system also contains a safety mechanism which locks the closure trigger 112 in its closed position. This safety mechanism is a leaf spring 159 which interacts with the safety button 131 on the rear of the instrument. Side plates on the portion of the toggle linkage assembly 124, 126 cause the leaf spring to remain in a tensioned position, and guide the leaf spring during its motion. When the front closure link 124 is in its straightened position, so that the rear closure link 128 is also rotated to be generally parallel with the shaft 130, the leaf spring 159 has been tensioned to restrain the toggle linkage 124, 128 in its parallel position. The safety button 131 on the rear of the instrument thereafter urges the leaf spring 159 in a forward direction, toward the cutting mechanism. This forward motion of the spring 159 causes the toggle linkages 124, 128 to be freed from the restraint of the spring 159. This motion allows freedom of movement for closure trigger 112.

As has been previously described, and as better seen in FIGS. 2a, 8, 9 and 9a–9d, the jaws 132, 142 of this instrument are closed by means of a cam surface 127 on the outer surface of the anvil 140. The anvil 140 pivots about pin 139 embedded in slot 141 of the closure channel 138 in shaft 130. Channel 138 is pushed forward with the actuation of the closure trigger 112. Closure channel surface 138a bears upon the cam surface 127 of the anvil 140, forcing it to pivot and move transversely within slot 153 contained in shaft 130. The location of the slot 153 as compared to the surface profile of the cam 127 determines motion of the anvil 140, such that the slot 153 and slot 141 combination forms a "fixed" pivot, which is fixed only with respect to the anvil 140. Therefore, anvil 140 is allowed to move transversely across the axis of a stationary tube 130. Shaft or stationary tube 130 forms the "ground" position for the pivot pin 139, so that its motion is only transverse compared to the shaft 130. As better seen in FIGS. 9b–9d, the motion of the anvil 140 follows a predetermined path. First, the anvil 140 is rotated to a position parallel to cartridge 150. Then, anvil 140 moves in a direction transverse to the axis of shaft 130, maintaining its parallel alignment with cartridge 150, until it is abutting pin 161 on cartridge 150.

This mechanism is also assisted by surface 127b on the opposite side of anvil 140. This is better seen in FIG. 9. This second cam surface 127b on the opposite portion of the proximal end of anvil 140 rides on buttons 139b held within the closure channel 138 during opening of the instrument. Second cam surface 127b similarly causes a reverse, opening motion of anvil 140 upon distal rotation of closure trigger 112 at the opening of the instrument.

The anvil 140 comes to rest on the gap spacing pin 161 which forms the distal end of the cartridge 150. The gap spacing pin 161 causes the anvil 140 to be held roughly parallel to the cartridge 150. This has an advantage in providing an evenly spaced tissue compression. It also has an advantage of retaining tissue between the anvil 140 and the cartridge assembly 150 and keeps the tissue from being "oozed" out of the distal end of the instrument 100. In this way, the anvil 140 acts as a simply supported beam with an evenly distributed load. As better seen in FIGS. 8 and 8a, there is provided a cartridge assembly containing six rows 190 of staples. These staples are arranged with two pairs of pusher blocks 192 near the outside of the cartridge 150. Then, one pair of pusher blocks 194 is placed within the interior of cartridge 150. Thus, four wedges 122 pass through this cartridge 150, as better seen in FIG. 8a. Of course, knife 160 also passes through the center of cartridge 150.

The firing force no form the staples provides an additional concentrated, yet moving, load on the cantilever beam which forms the anvil 140. The tissue compression load and the staple forming forces tend to deflect the anvil 140 from the cartridge 150. The anvil therefore is preloaded, so than uneven staple forming is avoided. This preload is placed on the gap spacing pin 161 at the end of the cartridge 150 so that a load roughly equivalent to that of tissue compression force and staple forming force is countered. This makes the anvil 140 acts simply supported beam, with loads at each end. This preload means that the anvil deflection caused by tissue compression and staple formation is compensated for by the reverse deflection caused by the gap spacing pin 161.

The disclosures of U.S. Pat. Nos. 4,633,861 and 4,633,874 (Chow, et al.) are incorporated by reference.

It can be seen in FIGS. 8, 11, 11a and 11b, that there is a unique lockout feature to this embodiment. As seen FIGS. 11a and 11b, the cartridge 150 contains a lockout member 170, having raised members 170a, which is better seen in FIG. 11. This lockout member 170 is provided within the cartridge so that is serves to lift the knife blade 160 over an obstructional block 172 placed within the stationary tube 130 of the mechanism. This causes the obstruction 172 to be cleared by the knife 160. Then, the knife 160 proceeds through the cartridge 150 for cutting. However, the knife has a notch 162 which engages the lockout member 170, and pushes it into opening 165 of cartridge 150. In this way, the lockout mechanism 170 operates at an even earlier time frame than previously disclosed locking mechanisms. It is important to realize that with the lockout mechanism described herein, the knife 160 is blocked even before entrance into cartridge 150.

As seen in FIG. 11b, after the knife 160 has been inserted into the cartridge 150, the raised members 170a of lockout member 170 have been caused to be captured below its cartridge retaining member 164 in opening 165, so that lockout member 170 becomes locked permanently within the cartridge 150. Therefore, after the knife 160 is retracted into the shaft 130, obstruction 172 now is level with the notch 166. In this way, there is no longer any clearance, between notch 166 and obstruction 172, as seen in FIG. 11b. In this way, if it is desired to refire this stapler, there is no possibility of knife hook 166 clearing the knife obstruction 172 in shaft 130. Therefore, refiring of this spent cartridge 150 is not possible.

If one were willing to accept any disadvantages which may be attendant, the stapler 100 may be modified as seen in FIG. 10a to allow cutting after the last staple has been fired. This is accomplished by removing member 166a adjacent to notch 166 using conventional methods, for example grinding or cutting. Or, knife 160 may be manufactured without notch 166 and member 166a.

Therefore, as seen from all the Figures previously listed above taken in conjunction with this Description, the following is a summary of the operation of the present invention. A fully loaded cartridge 150 is inserted into the stationary tube 130 at jaw 132. Thereafter, the instrument is inserted, closed, within a trocar and is opened, and gathers tissue between the anvil 140 and the cartridge assembly 150. The closure channel is operated by compressing the closure trigger 112. In this way, the closure trigger 112 causes all the closure mechanisms to rotate and move along an axis parallel to shaft 130. This causes the anvil 140 to encounter the gap setting pin 161 and capture tissue between the anvil 140 and cartridge 150. Thereafter, the anvil 140 is compressed onto the cartridge 150.

In the meantime, the clutch assembly of the firing trigger 114 has engaged the firing link 148, which is now operated. Tissue is stapled by rotation of the trigger 114. Also, simultaneously, the tissue is cut by the knife member 160. Once the firing stroke of the firing trigger 114 is completed, the rear safety button 131 must be released so that the mechanism can be reopened. The firing trigger 114 and closure trigger 112 are rotated to their original positions, and the lockout member 170 has caused the knife 160 to be obstructed from refiring. Thus the tissue is released, the mechanism retracted from the trocar tube, the cartridge 150 removed and a new cartridge inserted, and the stapler is again ready firing.

As seen in FIGS. 12 through 20a, there is described an alternative preferred embodiment of the present invention. There is seen a stapler which contains a handle portion 10, shaft portion 30, an anvil portion 40, cartridge assembly 50, rotational means 20, a first or closing trigger 12, a second or firing trigger 14, knife means 60, and firing wedges 54. The basic functions of all of these subassemblies are quite similar to those as described in the first preferred embodiment. However, there are certain aspects of the system which will now be more particularly described.

As seen in FIGS. 12 and 13, there is described a closure sheath 32 which is capable of camming the rear cam surface 43 of the anvil 40. This closure sheath 32 is operated by means of the closing trigger 12, attached thereto by means of a closure mechanism. The firing trigger 14 is similar to firing trigger 114 of the first embodiment, and is capable of activating the firing wedges 54 to expel staples from the stapling cartridge, while simultaneously activating knife means 60 to cut tissue between the two double rows of staples contained in cartridge assembly 50.

As will be better understood, there are certain aspects of the handle mechanism 10 which differ from the handle mechanism 110 of the first embodiment. As better seen in FIGS. 12a, 13, 14, 15 and 15a, the closing trigger 12 which operates the sheath 32 of the stapler is connected to firing trigger 14 by means of a two-piece linkage 34, 36. This linkage system 34, 36, is better seen in FIGS. 12a and 15a. Link 34 is connected by means of a pivot joint 45 to firing trigger 14 and is constrained to travel within an opening 45a in firing trigger 14. Link 34 is biased downward by spring means 33 connecting it to a boss in body plate 155. Link 36 is connected by means of a pivot joint 46 to closing trigger 12 and is constrained to travel within an opening 46a in trigger 12. Links 34 and 36 are constrained to move relative to each other due to link 36 nesting inside of a slot in link 34. The distance from pivot pin 13 to pivot joint 45 at which link 34 is connected to firing trigger 14 is proportionately smaller than that at which link 36 is connected to closing trigger 12. These differing distances or radii from pivot pin 13 cause the firing trigger 14 to rotate through a greater angle than that of the closing trigger 12 when the closing trigger mechanism is activated. This allows the firing trigger 14 to move from its initial position against the barrel position of the body to a position in which it can be easily activated for the firing operation. This occurs because link 36 is pulled upwards by the closing trigger 12 and, since it is nested in the slot 37 in link 36, link 34 pulls link 36 upward as well. The firing trigger 14 can be rotated into position against the grip portion of handle and continues to raise link 36. This additional travel of link 36 is accomplished since the slot in link longer than the body length of link 36 which is engaged in the slot 37. Spring means 33 connected to link 34 causes link 34 to remain in contact with link 36 as well as to help return both links 34 and 36 and the respective triggers 12 and 14 to their original positions.

As seen in FIGS. 13, 16 16a, 17 and 17a, rear toggle member 44 has an extended portion 47 which rotates into a 15 position so that in contacts the rear button release 31. The front toggle member 42, and rear toggle member 44 form the toggle linkage and are carried into an over-center position, thus locking sheath 32 into a position which cams anvil 40 against cartridge assembly 50. Pushing the rear button release 31 exerts force on the elongated part 47 of the rear toggle 44 and rotates the rear toggle 44 past its over-center point. This allows spring 150a in conjunction with spring 33 and the linkage 34, 36 to pull the firing trigger 14, and closing trigger 12 into the "ready" position. Of course, both links 34, 36 of the trigger return act respectively on the triggers 14, 12. In this way, the stapler 5 is reset for firing as seen in FIG. 13.

As also seen in FIGS. 12a and 13, there is contained in this mechanism a safety pawl. The safety pawl 22 is capable of preventing motion of the firing mechanism of this embodiment of stapler 5 until closing trigger 12 has been fully moved to its closed position against the instrument hand grip 18 of handle portion 10. Safety pawl 22 is biased into its blocking position by means of spring 160a. Safety pawl 22 is moved out of the way of the firing mechanism through contact of latch 42a with notch 5 22a. That is, the safety pawl 22 becomes disengaged from its blocking position against the firing rack 25 which ultimately is operated by the firing trigger 14. Once the safety panel 22 has been moved, firing can take place. As better seen in FIGS. 12, 13, 16, 16a, 17 and 17a, closure is initiated by moving the closing trigger 12 against the instrument handle grip 18. This rotates the toggle linkage to its locked and over-center point, that is generally parallel with stapler shaft 30. This further causes sheath 32 to move in place within the stationary channel 30a which forms the shaft portion 30 of the mechanism. Thus, the toggle linkage which comprises both the rear toggle 44 and the front toggle 42, operates so that it moves the closure sheath 32 (which may operate as a cramming collar) over the base 43 of the anvil 40. Thus, the closure mechanism now causes the anvil 40 and cartridge 50 to come in close proximity to each other.

At that point, the closure trigger 12 is held against the hand grip 18 and the firing trigger 14 is ready for actuation. The firing trigger 14 operates driver 89 connected to a belt 17, which is used to provide movement of firing rack 25 and driver rod 19. The belt 17 acts as a multiplier mechanism so that the firing trigger 14 pushes against the driver 89, seen in FIG. 13. Driver 89 thereafter causes the bottom portion 17c of belt 17 to move forward. Because one end of the belt 17a is fixed against the body of handle 18 of the stapler 5 and the other end of the belt 17b is attached to rack 25, this drives the knife means 60 and wedges 54 of the stapling mechanism forward. The motion of belt 17 causes motion of the driving rod 19 to be amplified as against the rotational motion of the firing trigger 14. Thus, this belt mechanism multiplies the firing distance travelled, so that stapling and cutting can take place.

The anvil portion 40 and cartridge assembly 50 operate very much as that of the first preferred embodiment. One difference, however, is that a preload is accomplished by tilting the anvil 40 and cartridge 50 toward each other at their distal ends to force distal closure to occur. As the proximal ends 40a of the anvil 40 and cartridge 50 are brought into a parallel position a preload is placed on 15 the gap pin 61. This is better seen in FIGS. 13 and 18. The cam mechanism 43 on the rear of the anvil 40 is designed with a multiple angle. In this way, the steeper proximal portion of the angle allows faster closing of the anvil 40 against the cartridge assembly 50. Then the distal or more shallow angle is contacted by the closing sheath 32 when the instrument is nearly closed and experiencing high tissue load and high preload on the gap setting pin 61 found in the forward most position of the cartridge 50. These compound angles are specifically designed to give higher mechanical advantage when needed and faster closure and wider opening when needed.

As better seen in FIGS. 18, 18a, 19, 19a, 20, 20a and 20b, the lockout mechanism of the second embodiment is 30 better seen when examining the cartridge 50 of the present system. There, it is seen as in FIG. 20, the lockout tab 71 is originally provided so that it is capable of lifting the knife means 60. In this way, the knife 60 moves forward and into the stapling cartridge 50. On the rearward motion of the knife, the forwardmost edge 63 of the knife mechanism 60 causes the lockout tab 71 to be rotated to become parallel with the stapling shaft 30. Thus, the knife 60 is made to move to a position lower in the stapling shaft 30. This causes the channel hook 59a which is contained in the stapling channel 59 to come into contact with the space 65 formed within the knife means 60. Thus, when it is now desired to move the knife mechanism forward, as will readily be appreciated, the hook 59 now catches on forward facing lip 66 of the knife means 60. Thus, the knife is incapable of moving forward and the stapler is now locked from firing through an already spent cartridge 50.

Of course, as seen in FIGS. 18 and 18a, there are disclosed four rows, that is two double rows 92 of staples in the cartridge 50. These rows 92 are actuated by pusher blocks 94 contacting wedges 54. Knife 60 passes through the center of rows 92.

In operation, the stapler of this second embodiment also performs similar functions. There is similar stapler safety, and clamping as that of the first preferred embodiment, and the firing and cutting of tissue 25 accomplished all in the same order. Stapler lockout is accomplished afterwards by retraction of the knife mechanism.

In a most highly preferred embodiment of the invention, a retractable knife is provided, eliminating the need for a spent cartridge lockout. Referring now to FIGS. 21–23, a housing, generally 200 contains one or more staple drivers generally 202 which form staples 204 substantially as previously described. The housing 200 also contains a wedge/knife sled subassembly, generally 201, comprising a knife or knife sled 206 and a wedge or wedge sled (containing multiple wedges) 208. The knife 206 is pivotally mounted to the wedge sled 208 via a pin 210, the pivot pin 210 riding within an inclined slot 212 in the knife 206. The pivot pin 210 also passes through an opening 214 in each of the wedges of the wedge sled 208. The wedge/knife sled subassembly 201 is retained within the housing or cartridge 200 by a driver retainer 216.

A pusher 218 emanating from the handle of the instrument urges the wedge/knife sled assembly, generally 201, in the direction $D_1$, when actuated by the operator of the instrument. As the wedges 208 are pushed in the direction $D_1$ by the pusher or driver rod 218, the front inclined edge 209 of the wedge contacts a complimentary inclined edge 203 of the staple driver(s) 202, forcing the staple driver(s) in the direction $D_2$, firing the staples through the tissue and forming them about an anvil (not shown) substantially as previously described. This staple firing sequence occurs following the clamping of the tissue between the cartridge 200 and the anvil as previously described.

Referring now to FIG. 21a, the sled assembly 201 is initially positioned at the rear 205 of the housing 200. As further illustrated in FIG. 21a, in this "start" position, the knife 206, by virtue of the pivot pin 210 and a slot 217 in the rear of driver retainer 216 (see also FIG. 23), is initially positioned with the tip of the knife 206 being below the exposed surface 207 of the cartridge 200. In this unexposed position, the knife 206 is incapable of inadvertently cutting the operator or patient.

During operation, at the initiation of a firing/cutting sequence, the pusher or driver rod 218 is advanced in the direction $D_1$, for example, by actuating a trigger mechanism at the handle of the instrument substantially as previously described. Alternatively, the pusher mechanism 218 could be manually advanced, although this would be a less preferred embodiment. The pusher 218 slides within a channel 219 within the cartridge 200 sized to permit such an operation. As the pusher 218 advances, it contacts (or may be fastened to) the trailing edge 220 of the wedge 208, forcing the wedge/knife sled assembly 201 in the direction $D_1$. During this initial motion, the knife 206 remains unexposed substantially as illustrated in FIG. 21a until the pivot pin 210 anchored in the wedge 208 contacts the front portion of the slot 212 in the knife 206, whereupon the knife 206 advances with the wedge and rotates upwardly through a cutting slot 222 in the cartridge 200 as illustrated in FIG. 22. At the moment that the pivot pin 210 contacts the front portion of the slot 212, the forward portion 224 in the slot 217 of the driver retainer base 216 causes the knife 206 to pivot upwardly, such that the cutting edge of the knife 206 is above the plane 207 of the cartridge 200, enabling the tissue to be cut, as illustrated in FIG. 23. This forward portion 224 of the slot 217 may be ramped or may simply comprise a vertical wall an the front of the slot 217.

As previously described, as the wedge/knife sled subassembly 201 moves in the direction $D_1$ the wedge 208 forces the staple drivers 203 in the direction $D_2$ to form the staples 204. The knife 206 follows closely behind and cuts the tissue as the staples form.

Upon reaching the end of travel, the cutting edge 206a of the knife 206 hits a stop 230 in the nose of the cartridge 200 (FIG. 22). The stop 230 is preferably the end of the cutting slot 222 in the cartridge 200 as illustrated in FIG. 22. At approximately the same time, the rear 206b of the knife reaches a forward slot 232 in the driver retainer base 216, causing the rear of the knife 206b to drop downward in the direction $D_4$ to a "parked" position, once again placing the knife 206 below the surface 207 of the cartridge 200 as illustrated in FIG. 21b. Alternatively, the knife 206 may achieve an unexposed position with respect to the surface 207 of the cartridge 200 by riding and/or pivoting down an inclined ramp 240 at the tip of the cartridge 200 (FIG. 21a).

Preferably, both of the slots 217, 232 in the driver retainer 216 are formed within a longitudinal groove or track 234 in the base 216 illustrated in FIG. 22. The cartridge 200 also preferably includes channels 236 for slideably receiving the wedge(s) 208.

Once the knife 206 has advanced to its "parked" position, for example, by being retained in an unexposed position within the forward slot 232 (FIG. 21b, 23) or the inclined ramp 240, the pusher 218 may be withdrawn, allowing the knife 206 to remain retracted in its "parked" position. At this point, the entire cartridge 200 may be discarded and replaced with a similar cartridge having a new knife 206, staples 204, wedge sled 208, and having the knife 206 "parked" in the rearward position, retracted below the surface 207 as illustrated in FIG. 21a.

Preferably, the stop 230 in the nose of the cartridge 200 comprises and inwardly tapering portion of the slot 222, whereby as the unexposed cutting edge 206A of the knife 206 advances, it wedges within the tapered end of the slot 222, providing frictional retention of the knife 206 in its unexposed position at the tip of the cartridge 200.

The knife 206 may be rigidly, pivotally, slidably, or releasably coupled to the wedge sled 208.

Most preferably, the knife 206 and wedge 208 are fastened to one another, either pivotally or rigidly, thereby comprising an integral wedge/knife assembly. This may be accomplished by providing a pivot pin passing through both the knife 206 and wedge 208, by fastening the two components to one another, e.g., by use of an adhesive, weldment, or by integrally forming the two components during fabrication. In this embodiment, as the knife/wedge assembly completes the cutting/stapling sequence, the entire assembly "parks" as illustrated in FIG. 21b, and only the pusher or driver 218 is withdrawn.

In a preferred embodiment of this device, illustrated in FIG. 24, the wedge sled 208 includes a channel 250 for slideably receiving the knife sled 206. The wedge sled 208 includes a stop 252 proximate to the rear of the channel 250 against which the rear end 206c of the knife sled 206 sits during a cutting sequence. The pusher rod 218 contacts or is fastened to the trailing edge 220 of the wedge 208, allowing the pusher rod 218 to advance the wedge 208 and knife sled 206 substantially as previously described. During the cutting sequence, the combination of inertial forces on the knife 206 and resistance from tissue on the cutting edge 206a will force the rear end 206c of the knife 206 into contact with the stop 252, enabling the wedge sled 208 to push the knife 206 toward the front end of the cartridge 200.

Because, in the embodiment of FIG. 24, the knife 206 is slideably received by the wedge sled 208, once the knife 206 reaches its "parked" position at the tip of the cartridge 200, it may remain in that position, allowing the wedge 208 to be retracted following the cutting sequence, as illustrated in FIG. 25.

As further illustrated in FIG. 24, the knife sled 206 preferably includes a guide block 254, which is sized to a fairly close tolerance to the dimensions of the channel 250, thereby allowing the knife 206 to remain relatively stable prior to and during the cutting sequence. For example, the guide block 254 helps maintain the knife 206 in an upright position, may help frictionally retain the knife 206 within the wedge 208 until after the cutting sequence is completed, and helps prevent "wavering" of the knife during the cutting operation. The guide block 254 preferably also includes a channel 256 for pivotally receiving the knife 206. This channel 256 allows the knife 206 to pivot downwardly, either from the front portion of the knife about a pivot 210a or, allows the rear of the knife to pivot downwardly about a pivot 210b as illustrated in FIG. 24. Note than the pivots 210a and 210b are alternative pivots, and would not be used together on the same instrument.

Once the knife decoupling assembly of FIG. 24 reaches the end of the cutting sequence, and the cutting edge 206a of the knife is retained in the tip of the cartridge 200, the wedge 208 is free to slide away from the knife 206, leaving the knife 206 in its "parked" position as illustrated in FIG. 25. In the case of a frictional tapered slot arrangement for wedging the cutting edge 206a of the knife in the tip of the cartridge 200, the frictional forces of the tapered slot 222 must obviously be greater than any frictional forces acting on the guide block 254 by virtue of the channel 250 in the wedge 208.

Another highly preferred embodiment of the invention is illustrated, in FIGS. 26-27, which will now be described. In this embodiment of the invention, an improved locking mechanism for an articulating surgical instrument is provided. The mechanism may be used with linear stapler cutters such as previously described, but may also be used with other articulating surgical instruments, such as open and endoscopic surgical stapling, cutting, applying, and grasping instruments.

In general, the mechanism operates to lock the articulatable head of a surgical instrument at an angle of articulation with respect to a rigid shaft to which the head is articulatably mounted. One such mechanism for performing the locking operation as illustrated in FIG. 26. In this device, the instrument, generally 300, includes a head, generally 302, articulatably mounted to a rigid shaft, generally 304, by an articulation joint 306, pivotally attaching the head 302 to the shaft 304.

The instrument 300 includes a device for transferring work from the proximal end of the instrument, which may include a handle/trigger mechanism substantially as previously described. This work transferring device allows the operator of the instrument 300 to control the articulation of the head 302 with respect to the shaft 304. In the embodiment of FIG. 26, an articulation band 308 is employed. Preferably, a pair of articulation bands 308 are used, one on either side of the instrument 300. In the embodiment of FIG. 26, the articulation band 308a on the right side of the instrument articulates the head 302 in a clockwise direction when the band 308a is pulled toward the proximal end of the instrument 300. Conversely, the band 308b on the left side of the instrument articulates the head 302 in a counterclockwise direction when pulled toward the proximal end of the instrument 300. The articulation bands 308a and 308b may comprise two sections of the same band, looped around a pulley or similar device at the proximal end of the instrument.

In a most highly preferred embodiment of the locking mechanism of the invention, the mechanism locks the head 302 at an angle of articulation at all times except when it is desired to articulate the head 302 with respect to the shaft 304. Upon actuation of the articulation device, for example by pulling the articulation band 308a toward the proximal end of the instrument 300, the locking mechanism of the invention releases, unlocking the head 302 and allowing articulation thereof. Discontinuation of the articulation step, for example, by stoppage of pulling forces on the articulation band 308a, causes the locking mechanism of the invention to reengage, locking the head 302 of the instrument 300 in its new angle of articulation.

The details of the preferred locking mechanisms of the present invention will now be described. It is to be understood that these details are described, for convenience, with respect to only one of the articulation bands 308a; however, in general, it is preferred than there be a complimentary locking mechanism operatively engaged with the other articulation band 208b substantially as shall now be described with respect to the articulation band 308a.

As illustrated in FIG. 26, the locking mechanism, generally 310, operatively engages the articulation band 308a. The articulation band 308a in effect provides a linkage connecting and allowing work to be transferred, from the proximal end of the instrument 300 to the distal end thereof. The linkage of FIG. 26 is longitudinally movable with respect to the shaft 304, and is fastened at the distal end of the instrument to the head 302 at a point spaced from the centerline C1 of the head 302, allowing the head 302 to be articulated about the pivot 306 when pulling (or, in the case of a stiff band, pushing) forces are exerted on the articulation band 308a.

Although the articulation band 308a of the embodiment of FIG. 26 appears as a flat band, which is preferably a flexible metal such as stainless steel, or a flexible polymeric material, it will now be readily understood by those of ordinary skill in the art that other linkage structures, such as rods, cables, wire, etc., of these and ocher materials could likewise be employed for articulation.

Referring again to FIG. 26, a preferred locking mechanism of the present invention includes a pawl 312 which engages a ratchet 314 at the proximal end of the head 302. The ratchet 314 is preferably circular or semi-circular in shape, and the pivot point 306 is preferably located at substantially the center of the circle defined by the ratchet 314. The pawl 312 is pivotally connected to the shaft 304 via a pivot pin 316. The pawl 312 is biased into locking engagement with the ratchet 314 by a biasing mechanism, such as a spring 318. In the embodiment of FIG. 26, the spring 318 is anchored to the shaft 304 by a pin 320.

The pawl 312 includes an engagement pin 322 which engages the articulation band 308a as illustrated. The articulation band 308a is either flexible along its entire length, or is at least flexible in the region 309 that passes around an the engagement pin 322. The entire locking mechanism 310 is supported by an upper support plate 324 which may include a complimentary lower support plate 326. The support plates 324, 326 may be housed within the tubular shaft 130 previously described.

The locking mechanism 310 operates as follows: when the articulation band 308a is tensioned, for example, by being pulled toward the proximal end of the instrument 300 by the operator thereof, the band 308a tends to straighten out in the flexed region 309 where the band 308a bends around and behind the engagement pin 322. As the flexed section 309 of the band 308a is pulled, it tends toward a linear orientation with respect to the remainder of the band 308a, causing the band 308a to act on and push the engagement pin 322 in the direction D5, compressing the spring 318, thus rotating the pawl 312 clockwise about the pivot 316, thereby releasing the pawl 312 from its locking engagement with the ratchet 314. The engagement pin 322 is free to slide in the direction D5 within a slot 323 in the upper support plate 324. The lower end of the engagement pin 322 may rest on the upper surface of the lower support plate 326 as illustrated.

Once the pawl 312 has been released from the ratchet 314 as described, the tensioning forces acting on the articulation band 308a cause the instrument head 302 to articulate about the articulation pivot 306.

As will, of course, be readily appreciated by those of ordinary skill in the art, although the articulation band 308a is described as providing articulation through a tensioning or pulling movement, it would be equally possible to induce articulation through the use of pushing forces, for example, by using a rod in place of the articulation band 308a having a flexible section 309 therein. Although the embodiment of FIG. 26 is shown with a flexible portion 309 in the articulation band 308a, it would, of course, also be possible to drive the engagement pin 322 in the direction D1 without using a flexible portion 309. Such a device could include, for example, a stiff rod in place of the band 308a having fastened thereto an outwardly tapering wedge forcing the engagement pin 322 in the direction D5 as the rod is pulled or pushed toward the proximal end of the instrument 300.

Returning now to FIG. 26, when tension on the articulation linkage 308a is relaxed, for example, following actuation of the articulation mechanism, the spring 318 is free to push the pawl 312 back into locking engagement with the ratchet 314, thus locking the head 302 at its new angle of articulation. In the embodiment of FIG. 26, the spring 318 is firmly grounded to the upper support plate 324, which is firmly attached to the support tube 130 of the instrument.

When the other articulation band 308b is tensioned, a mechanism similar to the locking mechanism 310 on the opposite side of the support plates functions as previously described. A similar pawl 312 is arranged to allow the head 302 to rotate counterclockwise with a minimum of resistance, but to lock when the head 302 is rotated clockwise. Thus, the locking and unlocking mechanism is symmetric, and functions for motion in either a clockwise or counterclockwise direction. In the embodiment of FIG. 26, the lower pawl 312 would engage a lower ratchet 315 on the head 302.

Another preferred embodiment of the articulation locking mechanism of the present invention is illustrated in FIG. 27. This embodiment includes a friction lock, which will now be described. In the device of FIG. 27, a pair of opposed articulation bands 408a and 408b pass through a shaft, generally 404, through an articulating coupling 406 to the head 402 of the instrument. The bands 408a and 408b are attached to the head 402 at points 402a and 402b, respectively, each spaced from the centerline C2 of the head 402.

Although the flexible coupling 406 of the embodiment of FIG. 27 is illustrated as a flexible neck, a pivot pin coupling similar to that disclosed in FIG. 26, or other articulation couplings known to those of ordinary skill in the art could also be employed.

In the embodiment of FIG. 27, a pair of biasing devices, such as springs 418a and 418b each bias an engagement pin 422a, 422b, respectively, against a flexed portion 409a, 409b, of the articulation bands 408a, 408b, respectively. Each pin 422a, 422b is attached to a locking cam 412a, 412b, respectively, and the locking cams 412a, 412b are pivotally mounted to the shaft 404 by pivot pins 416a, 416b, respectively. Each locking cam 412a, 412b includes a locking surface 413a, 413b, respectively, which frictionally engages, or otherwise locks the bands 408a, 408b, respectively, as illustrated. These locking surfaces 413a, 413b are forced into locking engagement with their respective bands by the biasing springs 418a, 418b, which pivot their respective cams about their respective pivot points.

Referring now, for convenience, to only one of the friction locking mechanisms, in operation, tension on the articulating band 408a causes the flexed portion 409a of the band to pull on the engagement pin 422a, causing the locking cam 412a to pivot about its pivot 416a, releasing the locking surface 413a of the locking cam 412a from its locking engagement with the other articulation band 408b. The release of the articulation band 408b by the locking cam 412a followed by continued tension on the articulating band 408a allows the head 402 to articulate in a counterclockwise direction about the articulation connection 406. Releasing tension on the band 408a allows the spring 418a to push the pin 422a, forcing the locking cam 412a back into locking engagement with the articulation band 408b, locking the head 402 in its new angle of articulation.

Alternative articulation locking mechanisms of the present invention are illustrated in FIGS. 28–31, which will now be described.

Referring now to FIGS. 28A and 28B, there is illustrated a locking mechanism comprising a ratchet 514 at the proximal end of the head, generally 502. The locking mechanism also includes a gear rack 512, which is capable of achieving locking engagement with the ratchet 514 by sliding the gear rack 512 distally toward the rack 514 in the direction D2 illustrated in FIG. 28B.

Preferably, the device of FIGS. 28A and 28B includes a biasing device, such as a spring, (not shown) which biases the gear rack 512 into locking engagement with the ratchet 514 prior to and following actuation by the articulation control mechanism of the instrument, the biasing device releasing the gear rack 512 upon actuation of the articulation mechanism, permitting articulation of the head 502 substantially as previously described. The rack 512 may be slideably positioned on the outside of the shaft 504 as illustrated in FIG. 28B, or it may be positioned internally thereof. The head 502 is articulatably mounted to the shaft, for example, at a pivot point 506 as illustrated.

Another preferred locking mechanism of the present invention is illustrated in FIG. 29. In this embodiment, the head, generally 602, includes at the proximal end thereof a detent device 614 having a plurality of detents 615 therein, and further includes a locking blade, generally 612, which may be biased into locking engagement with the detent 614, for example, by a spring, thereby locking the head 602 prior to and following articulation thereof by an articulation joy stick 650. In the embodiment of FIG. 29, the articulation band 608 is a one-piece flexible band attached to either side of the head 602 as illustrated, and passes around a pulley 652 attached to a shaft 654 driven by the joy stick 650. As illustrated in FIG. 29A, the locking blade 612 may be forced into locking engagement with the detent 614, either manually, or with a biasing spring or other automatic locking device such as previously described. The head 602 pivots about an articulation pivot 606 substantially as previously described. In the embodiment of FIG. 29, the locking blade 612 may be manually disengaged prior to articulation, for example, by simply sliding the bar 612 out of engagement with the detent 614 as illustrated in FIG. 29B. After articulation, the bar 612 may be slid back into locking relationship with the detent 614 as illustrated in FIG. 29C, locking the head 602 in its new angle of articulation.

Turning now no FIGS. 30–31, there is illustrated yen another preferred device for locking the head of an articulating surgical instrument. This device includes a head 702 articulatably mounted to a shaft 704 at a pivot 706, as illustrated in FIG. 30. The device further includes a fluid-filled bladder assembly, generally 714, for providing locking of the articulatable head 702. As best seen in FIG. 30A, the bladder assembly 714 preferably includes two interconnected bladders 714a and 714b connected by a connecting region 715. Fluid is free to flow between the bladders 714a and 714b through the connecting region 715 except when the bladder assembly 714 is acted upon by a pinch blade 712 which can be moved distally into a pinching orientation with the connecting region 715. As illustrated, the bladders 714a and 714b are each supported by a saddle 713a and 713b respectively. The saddles are sized to allow complete inflation of each bladder with the full compliment of fluid contained in both bladders 714a and 714b combined.

As used herein, the term "fluid" comprises liquids, gases, gels, microparticles, and any other material which can be made to flow between a pressure gradient.

In operation, the device of FIGS. 30–31 operates as follows: the pinch blade 712 is withdrawn, opening the connecting region 715 to fluid flow between the bladder 714a and 714b. This in effect opens a "valve" between the two bladders as schematically illustrated in FIG. 31A. The head 702 is then capable of being articulated by moving one or both of the articulation bands or straps 708a/708b. As illustrated in FIG. 31, if the head 702 is to be articulated in a clockwise direction, the band 708a is pulled proximally, rotating the head 702 about the pivot 706 in a clockwise direction as illustrated.

Referring again to FIG. 31, as the head 702 is articulated, in the direction shown, the bladder 714a is deflated, as the proximal end of the head 702 forces fluid through the opened connecting portion 715 into the other bladder 714b, enlarging that bladder as illustrated. Once the desired angle of articulation is achieved, the pinch blade 712 may again be forced into a closing/pinching relationship with respect to the connecting portion 715 of the bladder assembly 714 and the rear of the head 702, thereby precluding any further fluid flow from one bladder 714a/714b to the other, closing the "valve" as schematically illustrated in FIG. 31B. Once this is achieved, the head 705 is effectively locked in its articulated position. As illustrated in FIGS. 31a and 31b, the pinching blade 712 effectively acts as a valve, opening and shutting off fluid flow from one bladder to the other.

The pinch blade 712 may be manually operated, or may be attached to a biasing device in order to maintain the pinch blade in a biased position, closing off the connecting portion 715 until articulation is desired, at which point the pinch blade 712 may be removed from its biased position, opening the connecting portion 715.

Yet another preferred aspect of the present invention, an improved anvil closure mechanism, is illustrated in FIGS. 32–35. Referring now to FIGS. 32A, 32B, and 33, there is illustrated the distal portion of a surgical instrument including a shaft 830 with an anvil, generally 840, and a lower jaw 832, which holds a staple cartridge 850. The anvil 840 includes an upper jaw portion 842 which, as illustrated in FIGS. 32–33, is adapted to be opened and closed with respect to the lower jaw 832 for purposes of clamping and releasing tissue between the jaws 832/842.

The embodiments of FIGS. 32–35 may be beneficially employed with respect to any of the surgical instruments previously described, which instruments generally comprise a handle connected to a shaft to which the fastener applying or other surgical working assembly is attached at its distal end. The embodiments of FIGS. 32–35 may further advantageously be used with surgical instruments having a fastener applying assembly including a fastener holder, such as a cartridge 850 for holding one or more surgical fasteners, a driver for driving the surgical fasteners from the cartridge into the tissue, substantially as previously described, and a device such as the anvil 840 for forming the surgical fasteners about the tissue. The device of FIGS. 32–35 also preferably includes a closure mechanism for closing the anvil and the fastener holder 850 with respect to each other and for clamping tissue between the jaws 842 and 832. Preferably, the instrument also preferably includes a device for actuating the closure mechanism (subsequently described) and the handle preferably includes a device, such as a trigger mechanism for actuating the staple drivers and firing the surgical staples into the tissue, also substantially as previously described. It is preferred, of course, that the handle of these devices be mounted to the proximal end of the shaft 830.

Turning now to the specific features of the anvil closure mechanisms of FIGS. 32–35, and referring specifically to FIGS. 32–33, a preferred closure mechanism of the invention includes a closure tube, generally 838, rotatably mounted to the shaft 830. Preferably, the device also includes a knob or other mechanism 820 attached to the closure tube 838 for rotating the closure tube 838 with respect to the shaft 830. In a highly preferred embodiment of the invention, the closure tube 838 comprises a unitary part of the shaft 830, such that when the shaft 830 is rotated, the closure tube 838 necessarily rotates as well with respect to the anvil 840.

Referring now to FIGS. 32A and 32B, the preferred closure mechanism opens the jaws 832, 842, with respect to each other, when the closure tube 838 is rotated in a first direction R1, and closes the jaws 842, 832 with respect to each other when the closure tube 838 is rotated in the opposite direction R2 via the rotation knob 820. Preferably, the anvil 840 is pivotally mounted to the lower jaw 832 via a pivot point which may be a pin 839 embedded in a slot or hole in the lower jaw 832. Alternatively, if the shaft 830 and closure tube 838 are not integral, rather the shaft is fixed with respect to the anvil 840, it would be feasible for the pin 839 to be rotatably mounted within the shaft 830.

Referring now to FIG. 33, a preferred mechanism for allowing the closure tube 838 to open and close the anvil 840 with respect to the staple cartridge 850 includes a flange 860 proximate the distal end 838a of the closure tube 838. The flange 860 engages a beveled slot 862 formed in the heel 864 of the anvil 840. As the closure tube 838 is rotated in a first direction R1, the flange 860 rotates into the beveled slot 862, forcing the anvil 840 to pivot upwardly in the direction P1 about the pivot point 839.

As further illustrated in FIG. 33, the closure tube 383 includes a cutout portion 866 adjacent the flange 860. The cutout portion is sized to allow the anvil 840 to open to a fully opened position, by allowing the upper surface 827 of the heel 864 to pass outside of the cylinder defined by the closure tube 838, as the flange 860 is rotated into the beveled slot 862.

The closure tube 838 also preferably includes a projecting portion 868 proximate the cutout portion 866. The projecting portion 868 engages the upper surface 827 of the heel 864 of the anvil 840 as the closure tube 838 is rotated in a second direction R2 opposite from the first direction R1. This causes the anvil 840 to pivot about the pivot point 839 (FIG. 32B) to a closed or clamped position as schematically illustrated in FIG. 32A, allowing tissue to be clamped between the anvil 840 and the staple cartridge 850.

In another preferred embodiment of the invention, the closure tube 838, rather than including a flange 860, includes an inner thread or other surface having an inclined portion, which may comprise the inner wall of the closure tube 838, which inclined portion urges the anvil 840 closed with respect to the staple cartridge 850 as the closure tube is rotated in the second direction R2. In this embodiment, the inclined surface would act on the upper surface 827 of the heel 864 of the anvil 840, and would preferably act against a biasing device, such as a spring urging the anvil 840 open with respect to the staple cartridge 850.

Other embodiments for achieving opening and closure of the anvil 840 with respect to the staple cartridge 850 will now be readily apparent to those ordinarily skilled in the art, including elliptical closure tubes 838, and variations on the flange/inclined slot embodiment, including inclined tracks, threads, etc.

Another preferred anvil closure mechanism of the invention is illustrated in FIGS. 34A and 34B. In this embodiment, the closure mechanism includes a wedge 960 slideably received by an inclined slot 962 in the anvil 940. The wedge 960 of FIGS. 34A and 34B is pivotally connected to a rigid channel 932 which may comprise a lower jaw having a staple cartridge therein. The pivotal connection between the wedge 960 and channel 932 may be achieved by a pin 934 passing through one end of the wedge 960 and through the channel 932.

The wedge 960 of the embodiment FIGS. 34A and 34B is also pivotally connected by a pivot 936, at a point spaced from the pivot 934, to a drive shaft 938. This pivot 936 may also comprise a pin passing through both the drive shaft 938 and the wedge 960. The pivots 934 and 936 allow the driver 938 to drive the wedge 960 about the pivot 934. The driver 938 is preferably a rigid member, such as a rod slideably received by the shaft 930. Most preferably, the driver 938 includes a lever device, generally 920, for sliding the driver 938 distally and proximately with respect to the shaft 930. This device 920 may comprise, for example, a lever 922 which may be pivoted upwardly in a first direction L1, and pivoted downwardly in a second direction L2.

The lever 922 is pivotally fastened to the shaft 930 at a pivot point 934, which may be a pin passing through a flange 926 mounted to the shaft 930. The lever 922 is also pivotally connected at a pivot 928 to a linkage 927 which, in turn, is connected pivotally at a pivot 929 to a lever rod 925. The lever rod 925 is slideably supported by a second flange 923. The flange 923 is also fastened to the shaft 930. The lever rod 925, in turn, is fastened no a second linkage 921 which is slideably received by the driver 938 and captured by a pair of flanges 917 and 918.

In operation, the driver 938 is pulled rearwardly, for example, by pushing the lever 922 down in the direction L2, causing the linkage 921 to slide rearwardly on the driver 938, contacting the rear flange 918 and pulling the driver 938 rearwardly. This, in turn, causes the wedge 960 to pivot in a clockwise direction about the pivot 934, causing the anvil 940 to rotate about its pivot 939 to an open position as illustrated in FIG. 34A. The wedge 960 includes an upper surface 961 which contacts a rearward inclined surface 963 of the incline slot 962. As the wedge 960 rotates in a clockwise direction, the upper surface 961 rides against the rear inclined slot surface 963, causing the anvil 940 to pivot upwardly about the pivot 939.

When it is desired to close the anvil 940, the driver 938 is simply pushed forward, for example, by lifting the lever 922 in the direction L1 which, through the various pivots and link-ages of the lever mechanism 920, causes the linkage 921 to slide forwardly until it contacts the forward flange 917, pushing the driver 938 in the forward direction. This, in turn, causes the wedge 960 to rotate counter-clockwise about the pivot 934 as illustrated in FIG. 34B. The wedge 960 includes a lower surface 965 which contacts a forward inclined surface 967 of the incline slot 962 as the lever 960 is driven forward by the driver 938. This, in turn, causes the wedge 960 to drive the anvil down, about the pivot 939 into a closed orientation with respect to the channel 932 as illustrated in FIG. 34B.

In another preferred embodiment to the invention, the same or similar lever mechanism 920 is used, but with a different wedge system, as illustrated in FIG. 34C. In this embodiment, the wedge driver 1038 is rigidly connected to the wedge 1060 (i.e., without any pivots). The wedge 1060 comprises an inclined flange having a rear inclined surface 1061 and a forward inclined surface 1065. The flange 1060 is slideably received within an inclined slot 1062 in the anvil 1040. As illustrated, the inclined slot 1062 inclines upwardly in a direction from the distal end of the anvil 1040 to the proximal end thereof. In the embodiment of FIG. 34c, as the driver 1038 is pulled rearwardly in the direction D6, the rear surface 1061 of the inclined flange 1060 contacts the rear surface 1063 of the inclined slot 1062, drawing the anvil 1040 downwardly about the pivot 1039. The pulling force exerted on the driver 1038 can be increased, for example, by utilizing a lever mechanism similar to that of FIG. 34A, generally 920. The harder the pulling forces exerted on the driver rod 1038, the greater the clamping forces resulting from the anvil 1040 clamping against the lower jaw 1032.

To open the anvil 1040 of FIG. 34C, the driver 1038 is simply pushed in the opposite direction (toward the distal end of the instrument), which causes the forward surface of the inclined flange 1065 to slide against the forward inclined surface 1067 of the slot 1062, which in turn causes an anvil 1040 to ride upwardly about the pivot 1039.

Another highly preferred anvil closure mechanism of the present invention is illustrated in FIG. 35. In this embodiment, the anvil 1140 includes one or more pivot pins 1139 which ride in openings 1139a and the sides of the lower channel 1132, which contains a staple cartridge substantially as previously described. The rear end of the anvil 1140 also includes a tongue 1141 having a "nib" or other connecting point 1160 at the end thereof. This connecting point 1160 is spaced from the axis A1 of the anvil 1140 as illustrated. The tongue 1141 is preferably oriented substantially perpendicular with respect to the frontal portion 1140a of the anvil 1140. When mounted to the channel 1132, the anvil 1140 is able to pivot about the pivot point 1139 and about the axis A1.

The connection point 1160 is connected to an anvil driver 1138 which passes through the shaft 1130 to the handle of the instrument, which includes a mechanism such as a trigger, for actuating the driver 1138 proximately and distally with respect to the handle. When the driver 1158 is pulled rearwardly, a force F1 results, pulling on the connection point 1160 of the tongue 1141, creating a moment M1 about the axis A1, resulting in the clamping or closure of the anvil 1140 with respect to the channel 1132. Conversely, when an opposite force F2 is placed on the driver 1138, which is preferably a stiff member such as a rod, the driver 1138 drives the connection point 1160 of the tongue 1141 in the forward direction, creating a moment M2 about the axis A1, and pivoting the anvil 1140 open with respect to the channel 1132. It is preferred that the connection point 1160 not be rigidly fastened to the driver 1138, rather that there be some "play" between these two components, to allow the opening and closing action of the anvil 1140 to take place.

In the embodiment of FIG. 35, the connection nib 1160 is located substantially along the centerline CL of the tongue 1141 as illustrated in FIG. 35A. The connection point 1160 of FIG. 35A is also positioned "inboard" of the axis A1 with respect to the fastener holding channel 1132. This provides a fulcrum for leveraging the closure forces F1 as the anvil driver 1138 is drawn rearwardly. It is preferred that the distance L3 between the axis A1 and connection point 1160 be maximized within the confines of the instrument, thereby maximizing the clamping forces available.

The embodiment of FIG. 35 includes a joy stick for providing articulation of the channel 1132. The device is also shown with a knife 1106 for use in a linear cutter, substantially as previously described. A driver shaft for this knife or other surgical instrument may pass through a slot 1104 in the tongue 1141 as illustrated.

Yet another highly preferred embodiment of the present invention is illustrated in FIGS. 36–42. In this embodiment, a flexible neck or "flex-neck" mechanism is provided for allowing the articulation of the head assembly of a surgical instrument. One of the advantages of a flexible neck articulating attachment is the smoother "sweep" achieved by this method of articulation, which is preferred by some surgeons. Additionally, as seen in FIG. 36, a flexible neck provides for a relatively large bend radius "R," which allows a relatively smoother transmission of forces around the bend as will now be described.

Referring now to FIG. 36, there is illustrated a preferred flexible neck assembly, generally 1200, of the present invention. This assembly 1200 is beneficially used with respect to any articulatable surgical instrument, such as those having a handle connected to a shaft 1230 having a head assembly, generally 1240, including a surgical component, such as a linear stapler/cutter, associated therewith. The head assembly 1240 is articulatably mounted to the distal end of the shaft 1230 by a flexible neck member 1260 comprising a flexible material having at least one axial kerf 1262 therein.

As illustrated, the axial kerf(s) enable the flexible material of the flexible neck 1260 to bend along the kerf(s) along a bend radius "R" defined by the flexible neck 1260. This bend radius "R" allows for the smooth transmission of force around a bend with the use of flexible members, for example, for driving staple drivers, wedges, knives, etc. The articulatable surgical instrument also includes a mechanism for providing articulation to the head assembly, the mechanism being proximate the handle for providing remote articulation of the head assembly along the bend radius "R."

Most preferably, the flexible neck 1260 includes a plurality of kerfs 1262 separated by ribs 1269 as illustrated in FIG. 36. These kerfs 1262 and ribs 1269 are preferably equally spaced along the flexible neck 1260, thereby promoting a consistent bend radius "R" when the flexible neck 1260 is articulated. Of course, a flexible neck having multiple bend radii may be achieved by providing unequal spacing between the kerfs and the ribs, for example, spacing the ribs more closely at one end, such as the distal end of the flexible neck, and farther apart at the other end, such as the proximal end of the flexible neck, as illustrated in FIG. 36a. As will now be readily apparent to those of ordinary skill in the art, increasing the spacing of the kerfs and/or ribs reduces the bend radius of the section having increased spacing, more closely approximating a pivot point bend connection. Conversely, spacing the kerfs and/or ribs more closely results in a more gradual bend, having a larger bend radius.

In the embodiment illustrated in FIG. 36, the kerfs 1262 comprise annular grooves that extend at least partially around the perimeter of the flexible neck 1260. The kerfs 1262 preferably, however, comprise semi-annular grooves which are separated by a central longitudinal rib 1264 passing down the centerline C/L of the flexible neck 1260. This rib 1264 assists in providing stiffening to the flexible neck 1260, including sagging thereof, connects the ribs 1269, and provides a structure for receiving a slot 1266 therethrough for receiving surgical tools, such as a knife, a driver bar for pushing wedge blades for driving staples, or other surgical devices. This rib 1264 also allows transmission of force through the central, neutral, axial plane of the flexible neck, thus permitting the neck to be a means of pushing and pulling a tube distal to the neck, so that the jaw elements can be forcibly closed and opened. The longitudinal rib 1264 preferably runs the entire longitudinal length of the flexible neck 1260. The flexible neck 1260 also preferably includes a pair of side slots 1268 passing through each rib 1269. The ribs 1269 as illustrated in FIG. 37 preferably comprise disc-shaped portions which border each of the kerfs 1262 as illustrated in FIG. 36. Each of the discs 1269 includes at least one outboard slot 1270 spaced from the centerline C/L of the flexible neck by a distance D8 as illustrated in FIG. 37.

An alternative embodiment of the flexible neck is illustrated in FIGS. 39–41. In this embodiment, the kerfs 1262 comprise herringbone-shaped grooves in the flexible neck 1260 as illustrated. The herring bone-shaped grooves 1262 are preferably angled rearwardly (or forwardly) with respect to the axis A1 of the flexible neck 1260, preferably at an angle of about 30° with respect to the axis A1 when the flexible neck 1260 is in a linear orientation as illustrated. The herringbone kerfs 1262 provide for a smaller bend radius "R" than the embodiment of FIGS. 35–38. These grooves also allow the series of kerfs to interlock when the flexible neck is in the full, bent orientation, providing the flexible neck with increased torsional stiffness about the longitudinal axis. This increases the usefulness of the instrument for grasping and manipulating tissue. As illustrated in FIG. 40, the herring bone-shaped grooves are joined via a longitudinal rib 1264 which is offset from the axis A1 of the flexible neck 1260, and functions as a "backbone" for the herringbone-shaped ribs 1269. As illustrated in FIG. 41, the flexible neck 1260 of FIGS. 39–41 may include a central bore 1266 for receiving various surgical manipulating devices as previously discussed.

Each of the flexible necks of FIGS. 35–41 preferably includes a rear collar 1272 for securing the flexible neck within the shaft 1230 and a forward collar 1274 for securing the flexible neck to the head assembly 1240, for example, with a friction fit, crimp, fastener, or other fastening device.

The flexible material of the flexible neck 1260 may be of any suitable material, but preferably is a material which provides sufficient stiffness to transmit axial force and to allow the head assembly 1240 of the instrument to be inserted through a trocar or cannula, yet flexible enough to provide for the articulation described and illustrated herein. Examples of flexible materials which may be advantageously used with the flexible neck of the present invention include by way of example but not limitation, polycarbonates, nylon, high density polyethylene, rubber, neoprene, polyester, polytetrafluoroethylene (Teflon®), polypropylene, polyetherimide, and poly(vinyl chloride) [PVC].

Referring now to FIGS. 42 and 43, the flexible neck 1260 of the invention is preferably articulated by an actuation device, generally 1280, located proximate the handle at the distal end 1230a of the shaft 1230. In the embodiment of FIG. 42, the actuation assembly 1280 comprises a joy stick or lever 1282 rotatably received by a collar 1284 and having an axle 1286 fastened thereto. The collar 1284 further includes a knob 1288 which may be used for rotating the shaft 1230 and also rotating the head assembly 1240. The knob 1288 preferably provides a connection between the shaft 1230 and the handle of the device (not shown). The preferred embodiment of the invention also includes a mechanism for transferring force from the actuation means 1280 to the head assembly 1240. This force transfer mechanism may comprise a flexible member, such as a flexible band 1290 illustrated in FIG. 43. The flexible band 1290 is preferably connected at its distal end to the head assembly at a point spaced from the axis of the head assembly at the point 1290A illustrated in FIGS. 36 and 42. Although the flexible member 1290 is illustrated in FIG. 43 as a flexible ribbon, which may comprise stainless steel, it will now be readily appreciated by those of ordinary skill in the art that the flexible member 1290 may also comprise a rod, strap, band, cable, chain, or wire. The flexible member 1290 is preferably fastened at its proximal end 1290b to the axle 1286, for example, with a pin passing through a hole 1291 in the band 1290 and 1287 in the axle 1286. The flexible member 1290 is slidably received within the slots 1270 of the flexible member 1260 illustrated in FIG. 37. These slots 1270 are also spaced from the axis A1 and centerline C/L of the flexible member 1260.

Preferably, two flexible members 1290 are slidably received by two slots 1270 in the flexible member 1260. A first flexible member 1290 articulates the head assembly in a first direction and a second flexible member 1290 articulates the head assembly 1260 in a second direction opposite the first direction.

In the embodiment of FIG. 42, for example, one band 1290 would preferably be positioned on one side of the axle 1286 and a second band 1290 would be fastened to the other side of the axle 1286. Rotating the lever 1282 in a counterclockwise direction D9 would cause the band 1290 fastened to the front side of the axle 1286 to be pulled rearwardly, and would cause the band 1290 fastened to the rear side of the axle 1286 to be pushed forwardly, the net effect being the articulation of the head assembly 1240 in a counterclockwise direction D10. Similarly, if the control lever 1282 is rotated clockwise, the head assembly 1240 is articulated clockwise in the direction D11.

In a most highly preferred embodiment of the invention, the bands 1290 are fastened at their distal ends to the proximal end, of the head assembly 1240, substantially as previously described, but the bands 1290 are fastened at their proximal ends to a rigid pusher rod which, in turn, is fastened at its proximal end to the actuation axle 1286. In this way, the pushing forces acting on the flexible member 1260 can be more efficiently utilized. The pusher rods may be connected to the axle 1286, for example, with a loose-fitting pin or other fastening mechanism that allows the axle 1286 to push and pull the rod with respect to the shaft 1230 as the axle 1286 is rotated by the lever 1282. Other actuation mechanisms 1280 for providing remote articulation of the head assembly 1240 with respect to the shaft 1230 may be employed. Furthermore, articulation actuation devices such as a knob having a worm driving a worm gear, such as disclosed in co-pending application Ser. No. 08/219,846, incorporated by reference herein, may also be used with the articulation flexible neck 1260 of the present invention.

In another preferred embodiment of the invention, illustrated in FIG. 44, the flexible member includes a central slot 1266 which receives a band comprising a composite material, for example, a pair of stainless steel pins 1210, 1212, having a polymeric driver, such as Vectra® (manufactured and marketed by Hoescht) 1214 sandwiched therebetween. This composite driver may drive a knife/wedge fork 1216 such as illustrated in FIG. 44. The embodiment of FIG. 44 also includes a pair of channels 1218 therein, each of which receives a wire tension cable 1219 which is anchored to the head assembly 1240 at a point 1219a spaced from the axis A1 of the head assembly 1240 as illustrated. In this embodiment, articulation is achieved by pulling one of the wire tension cables 1219 rearwardly, which causes the head assembly 1240 to articulate in the direction of pull of the wire tension cable 1219. The embodiment of FIG. 44 also preferably includes a metal ring 1215 which presses to the collar 1274 of the flexible member 1216, providing hoop strength. This same ring 1215 may also comprise an anvil closure ring such as previously described.

Yet another preferred embodiment of the flexible neck of the invention is illustrated in FIGS. 45–49. In this embodiment, a device, generally 1300, for articulatably mounting a surgical component to a shaft is illustrated. The device 1300 comprises a flexible neck having a predetermined. These set as illustrated in FIG. 45. This may be achieved, for example, by injection molding the flexible neck 1360 in the preset arcuate bend as illustrated. The preset flexible neck 1360 also includes a plurality of teeth 1362 which mesh with corresponding kerfs 1364 as illustrated in FIGS. 45 and 46. Each of the teeth preferably has a beveled facing surface, 1396, 1398, as illustrated.

Preferably, the preset flexible neck 1360 comprises two separate sections, a top section 1366 and a bottom section 1368 in the embodiment of FIGS. 45–49, each of the two preset flexible neck sections 1366, 1368, is clamped together, for example, with a first spring 1370 at the proximal end and a second spring 1372 at the distal end. The flexible neck 1360 is preferably sheathed within a flexible outer tube or sleeve 1374, which allows the neck 1360 to achieve its predetermined arcuate set as illustrated in FIG. 45.

If the flexible neck 1360 is molded in a predetermined arcuate set, it is also necessary to include a sleeve or other mechanism for straightening the flexible neck 1360 as illustrated in FIG. 46. In this embodiment, a stiff outer tube 1376 could be used to slideably receive the flexible neck 1360, either by pushing the stiff tube 1376 over the neck 1360, or withdrawing the flexible neck 1360 into the stiff tube 1376.

In a most highly preferred embodiment of the invention, the flexible neck 1360 is molded in a straight orientation such as illustrated in FIG. 46, with the teeth 1362 and kerfs 1364 positioned out of alignment as illustrated. In this embodiment, there is no need for a stiffening tube 1376 for straightening, rather, a flexible tube 1374 is used to allow the flexible neck 1360 to assume its arcuate shape as the tube 1374 is passed over the neck 1360, applying axial pressure to each of the two sections 1366, 1368, as illustrated in FIG. 45. As the offset teeth 1362 engage their respective kerfs 1364 upon application of axial pressure to the top and bottom sections 1366, 1368, normal forces N act on the facing surfaces 1396, 1398, of the teeth of the top and bottom sections 1366, 1368, respectively, forcing the neck 1360 to bend as illustrated in FIG. 45 in order to allow the teeth 1362 of each section 1366, 1368, to achieve full engagement with the offset kerfs 1364 of the other section, 1368, 1366, respectively. The flexible sleeve 1374 must have a relatively high hoop tension to allow sufficient pressure to be applied to the flexible neck 1360 in order to achieve and maintain the arcuate bend of FIG. 45.

As illustrated in FIGS. 48–49, the flexible member 1360 includes an axial channel 1380 defined by a pair of slots 1380a, 1380b, in each section of the flexible neck, 1366, 1368, respectively. The axial channel 1380 is sized to permit the flexible neck 1360 to rotatably, slideably, threadably, or fixedly receive therethrough any of a number of surgical actuation devices, electrical wires, and driver or push/pull mechanisms, such as pusher rods, pulling cables, wires, bands, ribbons, rotative drill bit drivers, etc., for performing surgical functions at the head assembly of a surgical instrument such as clamping, cutting, stapling, grasping, cauterizing, drilling, etc.

The flexible neck 1360 also preferably includes a forward collar 1382 and a rear collar 1384. The forward collar 1382 comprises a unitary cylindrical member which may be fastened to a surgical head assembly, for example, with a pin placed through a hole 1383 in the collar 1382. The forward collar 1382 includes an annular flange 1385 against which the front portion 1366a of the top piece 1366 is placed. The rear collar 1384 comprises two halves which are clamped together, for example, with a pin or other fastening device passing through a shaft into which the rear collar 1384 is inserted, a pin or other fastener passing through a hole in the shaft and a hole 1387 in the rear collar 1384.

Referring now to FIGS. 49, 49A, and 49B, a preferred way in which the kerfs 1364 of the top portion 1366 may be offset from the teeth 1362 of the bottom portion 1368 is illustrated. In this embodiment, the kerfs 1364 of the top section 1366 are angled outwardly at an angle $theta_1$ which is greater than an angle $theta_2$ by which the kerfs 1364 of the lower portion 1368 of the flexible neck 1360 are angled outwardly. In a highly preferred embodiment, as illustrated in FIG. 49, these angles are 50° and 30°, respectively.

Referring now to FIG. 50, there is illustrated yet another preferred flexible neck mechanism of the present invention. In this embodiment, the flexible neck 1460 comprises two longitudinal sections 1466, 1468. One or both of the longitudinal sections include a slot 1470 therein which may be a keyhole slot having a "T" shape as illustrated. The slot 1470 receives a rigid straightening shaft having a cross-sectional area corresponding to that of the slot 1470. In the embodiment of FIG. 50, the flexible neck 1460 is preferably injection molded plastic having a pre-set arc, and is straightened by pushing the rigid straightener shaft through the flexible neck 1460. Other shapes, such as dovetails, "I-beam" shapes, etc. could be used for the slot 1470 and its corresponding rigid straightening shaft.

This invention has been described in connection with several particularly preferred embodiments. It is to be understood, however, that one may accomplish the invention in a number of substantially similar ways without departing from the scope and spirit of the invention. Accordingly, it is to be understood that the invention is to be better realized from the attached claims and their equivalents. Additionally, the present invention has been described above in terms of representative embodiments and figures which are intended to be illustrative and enabling to those of ordinary skill in the art, but not self-limiting. Furthermore, while many objects and advantages of the invention have been set forth, it is understood and intended that the invention is defined by the full scope of the following claims, and not by the objects and advantages.

What is claimed is:

1. Means for articulatably mounting a surgical component to a shaft, comprising flexible neck means, said flexible neck means comprising first and second longitudinal sections, each said longitudinal section having a plurality of teeth and kerfs therein, the teeth and kerfs of the first section being offset from the teeth and kerfs of the second section, whereby application of axial pressure to said sections resulting in forces acting in a direction normal to said longitudinal sections causing engagement of the teeth of the first longitudinal section with the kerfs of the second longitudinal section, thereby articulating said flexible neck means.

2. The means for articulatably mounting a surgical component of claim 1, wherein said means further comprises means for applying said axial pressure to said first and second longitudinal sections.

3. The means for articulatably mounting a surgical component to a shaft of claim 2, wherein said means for applying said axial pressure comprises a flexible tube slideably positioned about said flexible neck means.

4. The means for articulatably mounting a surgical component to a shaft of claim 3, wherein said offset teeth and kerfs are achieved by providing a first kerf angle to the teeth of the first longitudinal section and a second kerf angle to the teeth of the second longitudinal section, said first and second kerf angles being different from each other.

5. The means for articulatably mounting a surgical component to a shaft of claim 4, wherein said first kerf angle is about 30°, and wherein said second kerf angle is about 50°.

6. The means for articulatably mounting a surgical component to a shaft of claim 5, wherein said flexible neck means includes an axial channel therein for slideably receiving surgical actuation means therethrough.

* * * * *